(12) United States Patent
Biswas et al.

(10) Patent No.: US 9,718,808 B2
(45) Date of Patent: Aug. 1, 2017

(54) INHIBITORS OF THE RENAL OUTER MEDULLARY POTASSIUM CHANNEL

(71) Applicant: Merck Sharp & Dohme Corp., Rahway, NJ (US)

(72) Inventors: Dipshikha Biswas, Woodbridge, NJ (US); Fa-Xiang Ding, Staten Island, NY (US); Shuzhi Dong, Plainsboro, NJ (US); Xin Gu, Scotch Plains, NJ (US); Jinlong Jiang, Scotch Plains, NJ (US); Alexander Pasternak, Princeton, NJ (US); Takao Suzuki, Shanghai (CN); Joseph Vacca, Lansdale, PA (US); Shouning Xu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/106,847

(22) PCT Filed: Jan. 5, 2015

(86) PCT No.: PCT/US2015/010091
§ 371 (c)(1),
(2) Date: Jun. 21, 2016

(87) PCT Pub. No.: WO2015/105736
PCT Pub. Date: Jul. 16, 2015

(65) Prior Publication Data
US 2017/0037037 A1    Feb. 9, 2017

(30) Foreign Application Priority Data

Jan. 9, 2014  (WO) ............... PCT/CN2014/070384

(51) Int. Cl.
| | | |
|---|---|---|
| *A61K 31/501* | (2006.01) | |
| *A61K 31/403* | (2006.01) | |
| *A61K 31/4439* | (2006.01) | |
| *A61K 31/497* | (2006.01) | |
| *A61K 31/437* | (2006.01) | |
| *A61K 31/427* | (2006.01) | |
| *A61K 31/41* | (2006.01) | |
| *C07D 405/14* | (2006.01) | |
| *C07D 487/04* | (2006.01) | |
| *C07D 413/14* | (2006.01) | |
| *C07D 471/04* | (2006.01) | |
| *C07D 417/14* | (2006.01) | |
| *A61K 31/506* | (2006.01) | |
| *A61K 45/06* | (2006.01) | |

(52) U.S. Cl.
CPC .......... *C07D 405/14* (2013.01); *A61K 31/403* (2013.01); *A61K 31/41* (2013.01); *A61K 31/427* (2013.01); *A61K 31/437* (2013.01); *A61K 31/4439* (2013.01); *A61K 31/497* (2013.01); *A61K 31/501* (2013.01); *A61K 31/506* (2013.01); *A61K 45/06* (2013.01); *C07D 413/14* (2013.01); *C07D 417/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 4,216,221 A | 8/1980 | de Lannoy |
| 2010/0160255 A1 | 6/2010 | Kamata et al. |
| 2012/0238594 A1 | 9/2012 | Hunziker et al. |

FOREIGN PATENT DOCUMENTS

| | | |
|---|---|---|
| CL | WO2011045292 | 10/2010 |
| WO | 2010129379 A1 | 11/2010 |
| WO | WO2012130679 A1 | 10/2012 |
| WO | 2013028474 A1 | 2/2013 |
| WO | 2013066718 A2 | 5/2013 |
| WO | 2014018764 A1 | 1/2014 |

(Continued)

OTHER PUBLICATIONS

Bhave,G., Development of a selective small-molecule inhibitor Kir1.1, the renal outer medullary potassium channel, Mol. Pharmacol., 2011, 42-50, 79.

(Continued)

*Primary Examiner* — Alicia L Otton
(74) *Attorney, Agent, or Firm* — Baerbel R. Brown; Catherine D. Fitch

(57) ABSTRACT

The present invention provides compounds of Formula (I) and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

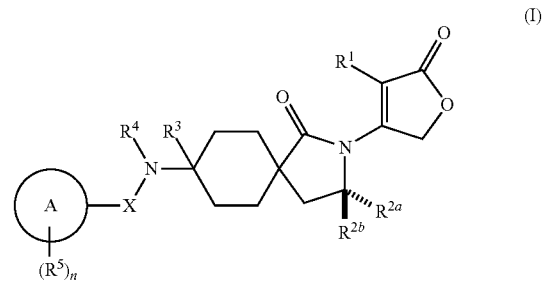

(I)

16 Claims, No Drawings

(56) References Cited

FOREIGN PATENT DOCUMENTS

| WO | 2014150132 A1 | 9/2014 |
| WO | WO2015103756 A1 | 7/2015 |

OTHER PUBLICATIONS

Boukouvalas, J. et al., Facile access to 4-(1-alkynyl)-2(5H)-furanones by Sonogashira coupling of terminal acetylenes with B-tetronic acid bromide: efficient synthesis of cleviolide, Tetrahedron Letters, 2007, p. 105-107, vol. 48.

Fringuelli, F. et al., A Simple Procedure for the Synthesis of Labile Aryl Oxiranes by Epdxidation, Organic Preparations and Procedures Int., 1989, p. 757-761, vol. 21, No. 6.

Hebert, S. C. et al., Molecular Diversity and Regulation of Renal Potassium Channels, Physiol Rev., 2005, p. 319-371, vol. 85.

Ho, K. et al., Cloning and expression of an inwardly rectifying ATP-regulated potassium channel, Nature, 1993, p. 31-38, vol. 362.

International Preliminary Report on Patentability for PCT/US2015/010091 mailed on Jul. 12, 2016, 5 pages.

International Search Report for PCT/CN2014/070384 mailed on Sep. 29, 2014, 15 pages.

International Search Report for PCT/US2015/010091 mailed on Apr. 3, 2015, 8 pages.

Ji, W. et al., Rare independent mutations in renal salt handling genes contribute to blood pressure variation, Nature Genetics, 2008, p. 592-599, vol. 40, No. 5.

Lewis, L. M., High-throughput screening reveals a small-molecule inhibitor of the Renal Outer Medullary Potassium Channel and Kir7.1, Mol. Phamcol., 2009, 1094-1103, 76.

Lifton, R. P. et al., Molecular Mechanisms of Human Hypertension, Cell, 2001, p. 545-556, vol. 104.

Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.

Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.

Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.

Molander, G. A. et al., Suzuki-Miyaura Cross-Coupling Reactions of Potassium Vinyltrifluoroborate with Aryl and Heteroaryl Electrophiles, J. Org. Chem, 2006, p. 9861-9686, vol. 71.

Nomura, Y. et al., Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.

Reinalter, S. C. et al., Pharmacotyping of hypokalaemic salt-losing tubular disorders, Acta Physiol Scand, 2004, p. 513-521, vol. 181.

Shuck, M. E. et al., Cloning and Characterization of Multiple Forms of the Human Kidney ROM-K Potassium Channel, The Journal of Biological Chemistry, 1994, p. 24261-24270, Vo. 269, No. 39.

Tobin, M. D. et al., Common Variants in Genes Underlying Monogenic Hypertension and Hypotension and Blood Pressure in the General Population, Hypertension, 2008, p. 1658-1664, vol. 51. No. 6.

Wang, W. et al., Renal potassium channesl: recent developments, Current Opinion in Nephrology and Hypertension, 2004, p. 549-555, vol. 13, No. 5.

Dong, Shuzhi, et al., Improvement of hERG-ROMK index of spirocyclic ROMK inhibitors through scaffold optimization and incorporation of novel pharmacophores, Bioorganic & Medicinal Chemistry Letters, 2017, p. 2559-2566, vol. 27.

International Search Report PCT/US 15/10091 dated Apr. 3, 2015, 8 pages.

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. §371 of PCT Application No. PCT/US15/010091, filed on Jan. 5, 2015, which claims priority from and the benefit of PCT Application No. PCT/CN14/070384, filed Jan. 9, 2014.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the Na$^+$/K$^+$/2Cl$^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia." Since then, numerous ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

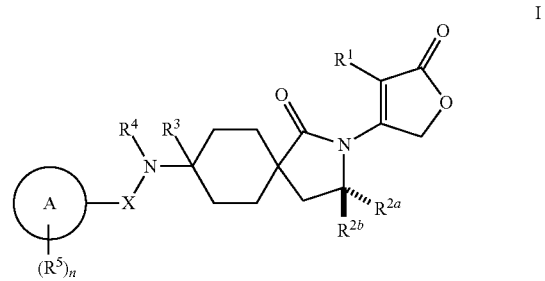

and pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

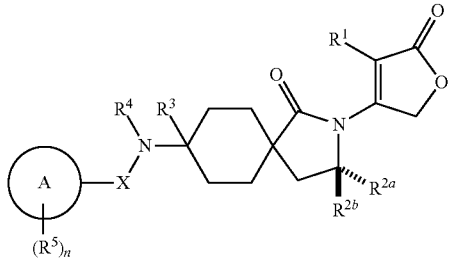

or a pharmaceutically acceptable salt thereof wherein:
ring A is
(1) aryl, wherein the aryl ring is unsubstituted or substituted by $R^6$,
(2) 5- or 6-membered heteroaryl, containing 1-3 heteroatoms independently selected from the group consisting of N, O, and S, wherein the heteroaryl ring is substituted by $R^6$, or
(3) fused tricyclic heteroaryl, containing 2-6 N heteroatoms;
$R^1$ is
(1) hydrogen, or
(2) $(C_{1-3})$alkyl;
$R^{2a}$ and $R^{2b}$ are independently
(1) hydrogen, or
(2) $(C_{1-3})$alkyl;
$R^3$ is
(1) hydrogen, or
(2) $(C_{1-3})$alkyl;
$R^4$ is
(1) hydrogen,
(2) $(C_{1-6})$alkyl,
(3) hydroxy$(C_{1-6})$alkyl,
(4) $(C_{1-3})$alkylC(O)N$(R^7)_2$, or
(5) $(C_{1-3})$alkyl-heteroaryl, wherein heteroaryl is 5- or 6-membered monocyclic ring and contains 1-3 heteroatoms independently selected from the group consisting of N, O, and S;
each $R^5$ is
(1) oxo,
(2) $(C_{1-3})$alkyl, or
(3) halo;
$R^6$ is a five-membered heteroaryl containing 1-4 heteroatoms independently selected from the group consisting of N, O, and S;
each $R^7$ is
(1) hydrogen, or
(2) $(C_{1-3})$alkyl;
X is —$(C_{1-3})$alkyl- optionally substituted by hydroxy; and n is 0, 1, 2, or 3.

In one embodiment, $R^1$ is hydrogen or methyl. In one embodiment, $R^1$ is hydrogen. In another embodiment, $R^1$ is $(C_{1-3})$alkyl. In one class of this embodiment, $R^1$ is methyl.

In one embodiment, $R^{2a}$ is hydrogen. In one class of this embodiment, $R^{2b}$ is $(C_{1-3})$alkyl. In a subclass of this class, $R^{2b}$ is methyl.

In one embodiment, $R^{2b}$ is hydrogen. In one class of this embodiment, $R^{2a}$ is $(C_{1-3})$alkyl. In a subclass of this class, $R^{2a}$ is methyl.

In one embodiment, $R^3$ is hydrogen. In one embodiment, $R^3$ is $(C_{1-3})$alkyl. In one class of this embodiment, $R^3$ is methyl.

In one embodiment, $R^3$ is hydrogen or methyl.

In one embodiment, $R^4$ is hydrogen. In one embodiment, $R^4$ is $(C_{1-6})$alkyl. In one embodiment, $R^4$ is $(C_{1-3})$alkyl. In one class of this embodiment, $R^4$ is methyl, ethyl, or propyl. In one subclass of this class, $R^4$ is methyl. In one subclass of this class, $R^4$ is ethyl. In one subclass of this class, $R^4$ is propyl.

In one embodiment, $R^4$ is hydroxy$(C_{1-6})$alkyl. In one class of this embodiment, $R^4$ is -ethyl-OH.

In one embodiment, $R^4$ is $(C_{1-3})$alkylC(O)N$(R^7)_2$. In one class of this embodiment, one $R^7$ is hydrogen and the other $R^7$ is $(C_{1-3})$alkyl. In one class of this embodiment, the two $R^7$ groups are each hydrogen. In one class of this embodiment, the two $R^7$ groups are each $(C_{1-3})$alkyl. In a subclass of this class, the two $R^7$ groups are each methyl.

In one embodiment, $R^4$ is $(C_{1-3})$alkyl-heteroaryl, containing 1-3 heteroatoms independently selected from the group consisting of N, O, and S. In one class of this embodiment, $R^4$ is $(C_{1-3})$alkyl-heteroaryl, containing 1-2 heteroatoms independently selected from the group consisting of N and O. In one class of this embodiment, $R^4$ is —$CH_2$-oxazolyl.

In one embodiment, $R^4$ is hydrogen or methyl.

In one embodiment, $R^5$ is oxo, methyl, or fluoro. In one class of this embodiment, n is 1. In one class of this embodiment, n is 2. In one class of this embodiment, n is 3.

In one embodiment $R^5$ is methyl.

In one embodiment, n is 0. In one embodiment, n is 1. In one embodiment, n is 2. In one embodiment, n is 3.

In one embodiment, ring A is aryl, wherein the aryl ring is unsubstituted or substituted by $R^6$. In one class of this embodiment, ring A is a fused aryl unsubstituted by $R^6$. In one subclass of this class, ring A is 1,3-dihydroisobenzofuran. In one class of this embodiment, ring A is phenyl substituted by $R^6$.

In one embodiment, ring A is 5- or 6-membered heteroaryl, containing 1-3 heteroatoms independently selected from the group consisting of N, O, and S, wherein the heteroaryl ring is substituted by $R^6$. In one class of this embodiment, ring A is pyridinyl, pyrazinyl, pyridazinyl, or thiazolyl, wherein each ring is substituted by $R^6$. In on subclass of this embodiment, ring A is pyridinyl substituted by $R^6$. In on subclass of this embodiment, ring A is pyrazinyl substituted by $R^6$. In on subclass of this embodiment, ring A is pyridazinyl substituted by $R^6$. In on subclass of this embodiment, ring A is thiazolyl substituted by $R^6$.

In one embodiment, ring A is a fused tricyclic heteroaryl, containing 2-6 N heteroatoms. In one class of this embodiment, ring A is a fused tricyclic heteroaryl, containing 4-5 N heteroatoms. In one class of this embodiment, ring A is 5H-tetrazolo[5,1-a]isoindole, 4,5-dihydrotetrazolo[1,5-a]quinolone, 8H-tetrazolo[1',5':1,2]pyrrolo[3,4-b]pyridine, or tetrazolo[1,5-a]quinoline.

In one embodiment,

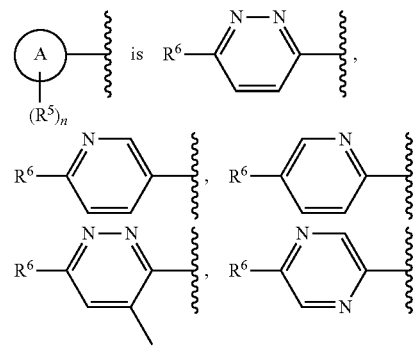

-continued

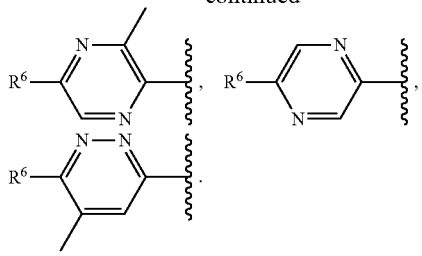

In one class of this embodiment, $R^6$ is tetrazolyl.

In one class of this embodiment, $R^1$ is methyl. In one subclass of this class, $R^3$ is methyl. In one sub-subclass of this subclass, $R^6$ is tetrazolyl. In one subclass of this class, $R^3$ is hydrogen. In one sub-subclass of this subclass, $R^6$ is tetrazolyl.

In one class of this embodiment, $R^1$ is hydrogen. In one subclass of this class, $R^3$ is methyl. In one sub-subclass of this subclass, $R^6$ is tetrazolyl. In one subclass of this class, $R^3$ is hydrogen. In one sub-subclass of this subclass, $R^6$ is tetrazolyl.

In one embodiment,

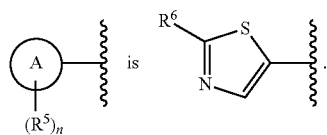

In one class of this embodiment, $R^6$ is tetrazolyl.

In one class of this embodiment, $R^1$ is methyl. In one subclass of this class, $R^3$ is methyl. In one sub-subclass of this subclass, $R^6$ is tetrazolyl. In one subclass of this class, $R^3$ is hydrogen. In one sub-subclass of this subclass, $R^6$ is tetrazolyl.

In one class of this embodiment, $R^1$ is hydrogen. In one subclass of this class, $R^3$ is methyl. In one sub-subclass of this subclass, $R^6$ is tetrazolyl. In one subclass of this class, $R^3$ is hydrogen. In one sub-subclass of this subclass, $R^6$ is tetrazolyl.

In one embodiment,

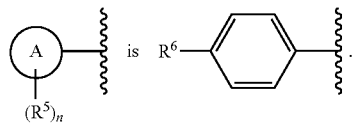

In one class of this embodiment, $R^6$ is tetrazolyl.

In one class of this embodiment, $R^1$ is methyl. In one subclass of this class, $R^3$ is methyl. In one sub-subclass of this subclass, $R^6$ is tetrazolyl. In one subclass of this class, $R^3$ is hydrogen. In one sub-subclass of this subclass, $R^6$ is tetrazolyl.

In one class of this embodiment, $R^1$ is hydrogen. In one subclass of this class, $R^3$ is methyl. In one sub-subclass of this subclass, $R^6$ is tetrazolyl. In one subclass of this class, $R^3$ is hydrogen. In one sub-subclass of this subclass, $R^6$ is tetrazolyl.

In one embodiment,

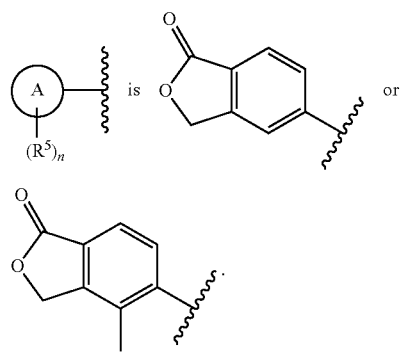

In one class of this embodiment, $R^1$ is methyl. In one subclass of this class, $R^3$ is methyl. In one subclass of this class, $R^3$ is hydrogen.

In one class of this embodiment, $R^1$ is hydrogen. In one subclass of this class, $R^3$ is methyl. In one subclass of this class, $R^3$ is hydrogen.

In one embodiment,

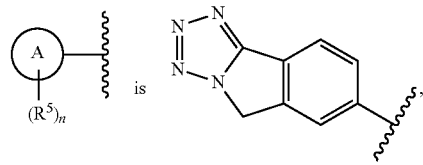

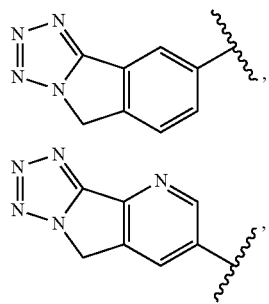

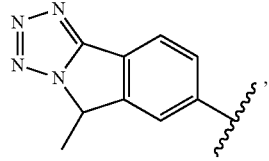

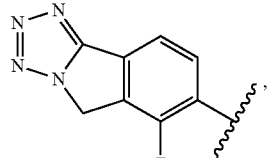

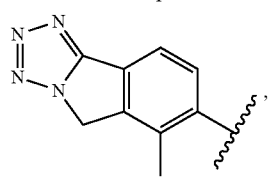

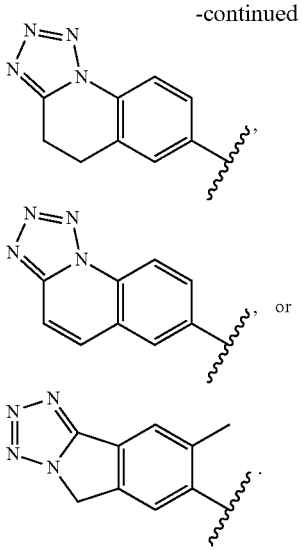

In one class of this embodiment, $R^1$ is methyl. In one subclass of this class, $R^3$ is methyl. In one subclass of this class, $R^3$ is hydrogen.

In one class of this embodiment, $R^1$ is hydrogen. In one subclass of this class, $R^3$ is methyl. In one subclass of this class, $R^3$ is hydrogen.

In one embodiment, $R^6$ is tetrazolyl. In one class of this embodiment, $R^6$ is

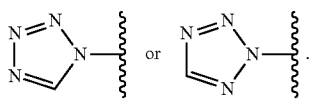 [SMILES: *n1cnnn1 ; *n1ncnn1]

In one subclass of this class, $R^6$ is

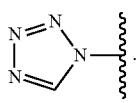

In one subclass of this class, $R^6$ is

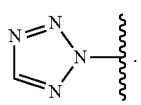

In one embodiment, X is

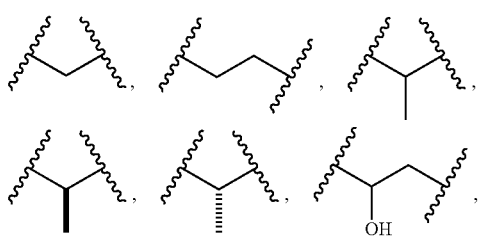

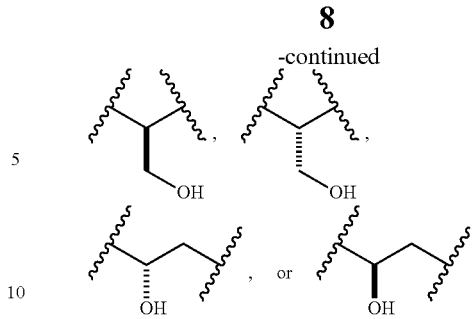

In one class of this embodiment, $R^1$ is methyl. In one subclass of this class, $R^3$ is methyl. In one sub-subclass of this subclass, $R^4$ is hydrogen. In one sub-subclass of this subclass, $R^4$ is methyl. In one subclass of this class, $R^3$ is hydrogen. In one sub-subclass of this subclass, $R^4$ is hydrogen. In one sub-subclass of this subclass, $R^4$ is methyl.

In one class of this embodiment, $R^1$ is hydrogen. In one subclass of this class, $R^3$ is methyl. In one sub-subclass of this subclass, $R^4$ is hydrogen. In one sub-subclass of this subclass, $R^4$ is methyl. In one subclass of this class, $R^3$ is hydrogen. In one sub-subclass of this subclass, $R^4$ is hydrogen. In one sub-subclass of this subclass, $R^4$ is methyl.

In one class of this embodiment, X is

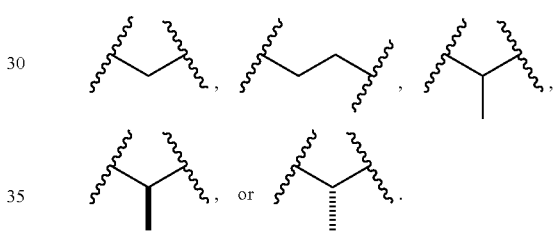

In one subclass of this class, $R^1$ is hydrogen. In one sub-subclass of this subclass, $R^3$ is hydrogen. In one sub-subclass of this subclass, $R^3$ is methyl. In one subclass of this class, $R^1$ is methyl. In one sub-subclass of this subclass, $R^3$ is hydrogen. In one sub-subclass of this subclass, $R^3$ is methyl.

In one class of this embodiment, X is

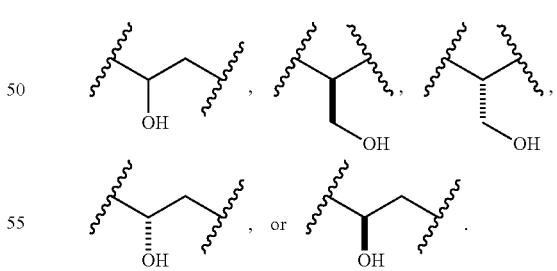

In one subclass of this class, $R^1$ is hydrogen. In one sub-subclass of this subclass, $R^3$ is hydrogen. In one sub-subclass of this subclass, $R^3$ is methyl. In one subclass of this class, $R^1$ is methyl. In one sub-subclass of this subclass, $R^3$ is hydrogen. In one sub-subclass of this subclass, $R^3$ is methyl.

In one embodiment, $R^1$ is hydrogen or methyl; $R^{2a}$ and $R^{2b}$ is independently hydrogen, or methyl; $R^3$ is hydrogen or methyl; $R^4$ is hydrogen or methyl; $R^5$ is methyl; X is

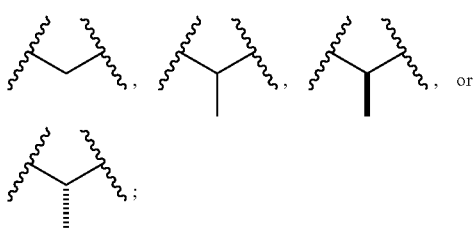

and n is 0, 1, or 2. In one class of this embodiment, $R^6$ is tetrazolyl.

In one embodiment, the present invention is directed to compounds of Formula I-a:

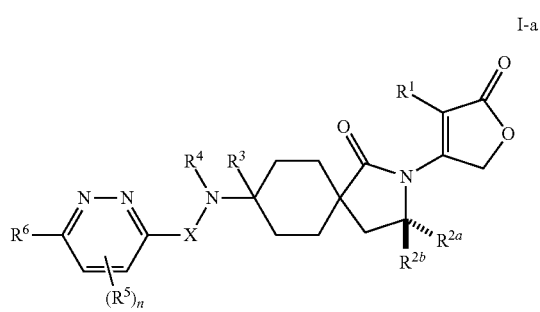

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-b:

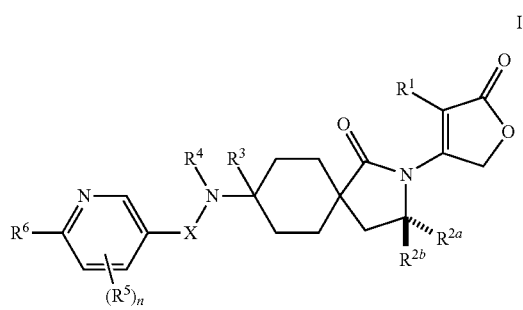

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-c:

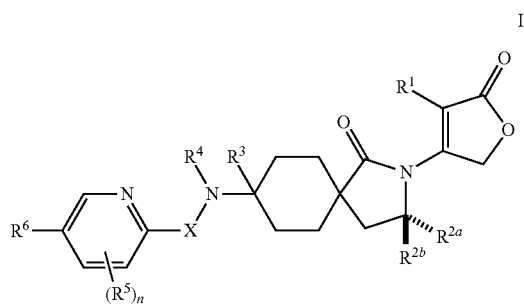

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-d:

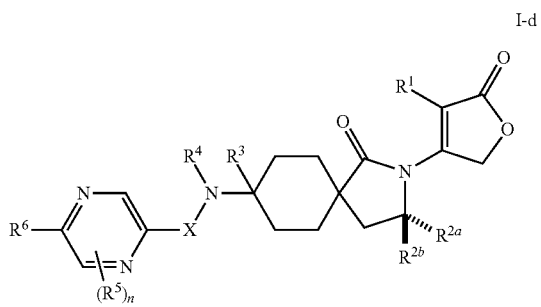

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-e:

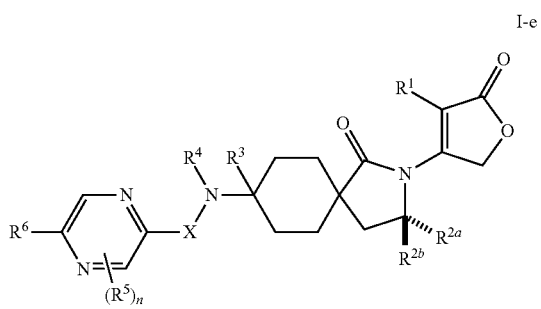

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-f:

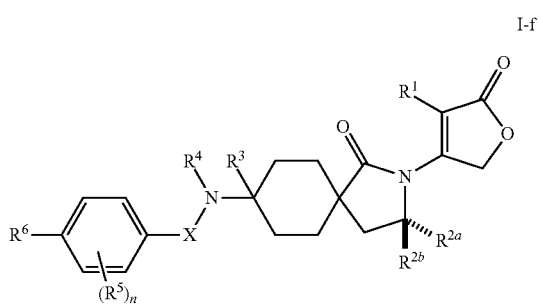

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-g:

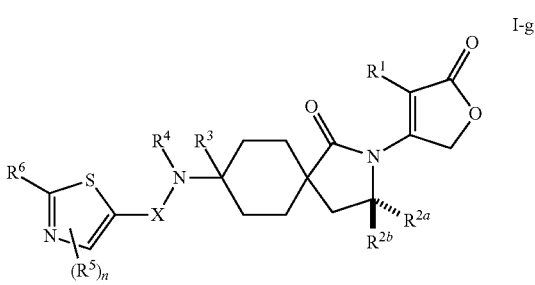

or a pharmaceutically acceptable salt thereof, wherein $R^1$, $R^{2a}$, $R^{2b}$, $R^3$, $R^4$, $R^5$, $R^6$, $R^7$, X, and n are as previously defined.

In one embodiment, the present invention is directed to compounds of Formula I-h:

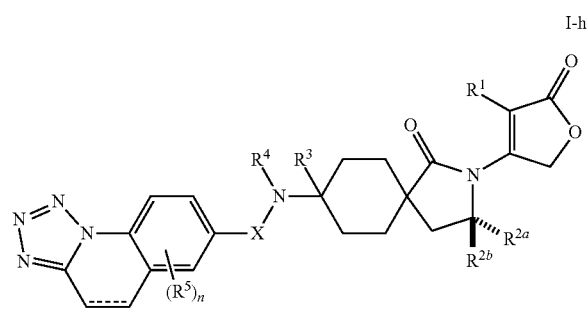

or a pharmaceutically acceptable salt thereof, wherein $R^1$, $R^{2a}$, $R^{2b}$, $R^3$, $R^4$, $R^5$, $R^7$, X, and n are as previously defined.

In one embodiment, the present invention is directed to compounds of Formula I-i

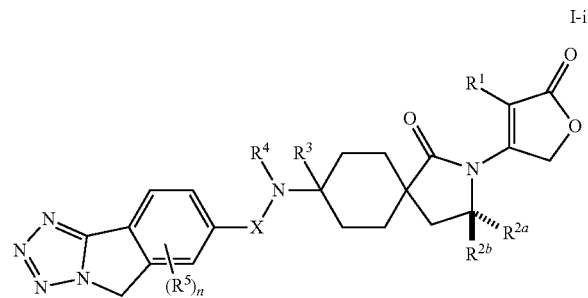

or a pharmaceutically acceptable salt thereof, wherein $R^1$, $R^{2a}$, $R^{2b}$, $R^3$, $R^4$, $R^5$, $R^7$, X, and n are as previously defined.

All structural Formulas, embodiments and classes thereof described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). In specific embodiments, alkyl is $C_{1-6}$alkyl or $C_{1-3}$alkyl. "Cycloalkyl" is a cyclized alkyl ring having the indicated number of carbon atoms. Examples of cycloalkyl include cyclopropyl, cyclobutyl, cyclopentyl and cyclohexyl. In specific embodiments, cycloalkyl is $C_{3-8}$cycloalkyl, $C_{3-6}$cycloalkyl, or cyclopropyl. When an "alkyl" group is a linking group between two other moieties, then it may also be a straight or branched chain; examples include, but are not limited to —$CH_2$—, —$CH_2CH_2$—, —$CH_2CH(CH_3)CH_2$—, —$CH_2CH(CH_2CH_3)CH_2$—.

"Halo" or "halogen" means —F, —Cl, —Br, or —I. Fluoro or chloro are preferred.

"Aryl" is commonly used to refer to carbocyclic aromatic structures. The most common aryl groups are phenyl and naphthyl. Phenyl is generally the most preferred aryl group. Aryl can be fused with other groups such as cycloalkyl and heterocyloalkyl. An example of a fused aryl is 1,3-dihydroisobenzofuran. The fusion may be bridged or spiro. If aryl is fused with a heteroaryl group, it will be defined as a heteroaryl group.

"Heteroaryl" means a heteroaromatic ring containing at least one ring heteroatom selected from N, O and S (including SO and $SO_2$), as defined more specifically herein. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, indazolyl, benzofuranyl, benzothiophene (including S-oxide and dioxide), furo(2,3-b)pyridyl, quinolyl, indolyl, isoquinolyl, quinazolinyl, dibenzofuranyl, and the like. The heteroaryl group may be fused one or more times with other groups such as cycloalkyl, cycloalkenyl, heterocycloalkyl, aryl or other heteroaryl groups. An example of a fused heteroaryl is 7-(oxiran-2-yl)tetrazolo[1,5-a]quinolone. The fusions may form bridges and spiro groups.

Unless expressly depicted or described otherwise, variables depicted in a structural formula with a "floating" bond, such as $R^5$, are permitted on any available carbon atom in the ring to which the variable is attached.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configurations. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out as an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formulas I-a to I-i and all embodiments and classes thereof. Reference to the compounds of this invention as those of a specific formula or embodiment, e.g., Formula I or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups, the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to, sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diuresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of body weight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI@), candesartan, e.g., candesartan cilexetil (ATACAND@), eprosartan, e.g., eprosartan mesylate (TEVETAN@), irbesartan (AVAPRO@), losartan, e.g., losartan potassium (COZAAR@), olmesartan, e.g, olmesartan medoximil (BENICAR@), telmisartan (MICARDIS@), valsartan (DIOVAN@), and any of these drugs used in combination with a thiazide-like diuretic such as hydrochlorothiazide (e.g., HYZAAR@, DIO VAN HCT@, ATACAND HCT@), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tripeptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloroderivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIAC®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the the steps of reaction schemes may be varied to facilitate the reaction or to avoid unwanted reaction products. The substituents in the Schemes generally correspond to the substituents defined in Formula I at the same positions on the structures. The ring

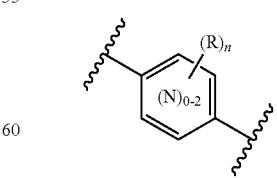

is intended to represent A as defined in Formulas I and I-a through I-f encompasses the six-carbon phen-di-yl ring or the ring having one or two nitrogens replacing one or two of the carbons.

Compounds of formulas 1.4 and 1.6 can be prepared by sequence shown in Scheme 1. Aldehydes or ketones (1.2 and 1.5) may be used in reductive alkylation reactions of spirocyclic amines 1.3 to afford ROMK inhibitors of the formulas 1.4 and 1.6 by using various reductive amination conditions (for example using sodium cyanoborohydride, sodium triacetoxy borohydride, or titanium tetra-isopropoxide, followed by sodium borohydride or sodium cyanoborohydride). Spirocyclic amines may be free bases, or they may be salts, in which case a base such as triethylamine or N;N-diisopropylethylamine may be added. When enantiomerically pure chiral amine and a ketone are used, the column separation may be applied to separate two diastereomers. Chiral HPLC separation of enantiomers or diastereomers of 1.4 and 1.6 may be performed to provide single enantiomers or diastereomers when a non-enantiomerically pure amine 1.3 is used. N-methyl analogs 1.1 and 1.7 may be synthesized from the NH analogs 1.4 and 1.6, respectively, by reductive amination with formaldehyde, aldehydes, sodium acetate and sodium cyanoborohydride at room temperature.

SCHEME 1

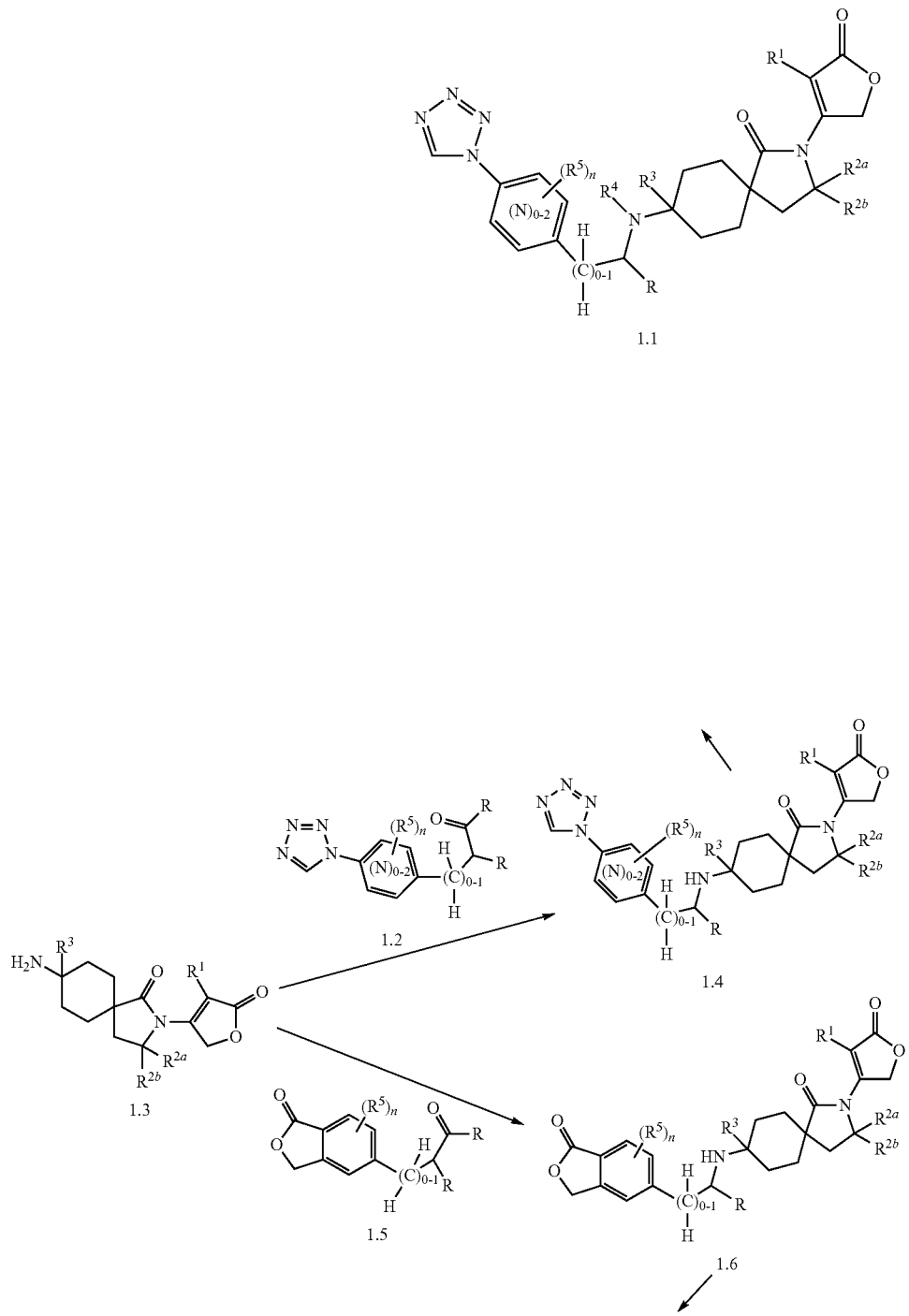

-continued

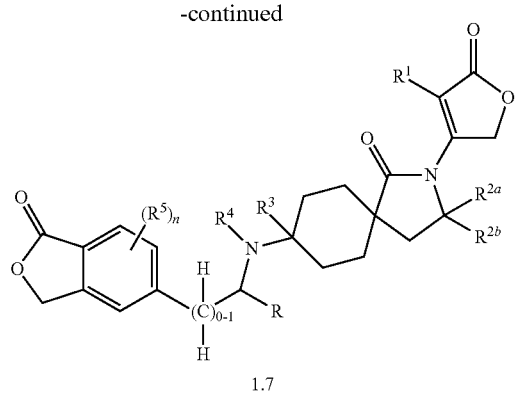

1.7

Compounds of formulas 2.1, 2.3, 2.5 and 2.6, which are substituted with an OH group, can be prepared following the sequence detailed in Scheme 2. Coupling of epoxides 2.2 and 2.4 to spirocyclic amines 1.1 at elevated temperatures leads to the formation of alcohols 2.3 and 2.5 (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol, 2-propanol and toluene. Spirocyclic amines may be free bases, or they may be salts, in which case a base such as triethylamine or N,N-diisopropylethylamine may be added. Note that when enantiopure chiral epoxides of types 2.2 and 2.4 are employed epoxide opening occurs with retention of stereochemistry in the benzylic position and individual isomer 2.3 or 2.5 may be obtained (and if the (S)-epoxide is employed the alcohol produced will have the opposite stereochemistry to that shown). Alternatively, chiral HPLC separation of enantiomers or diastereomers of 2.3 and 2.5 may be performed to provide single enantiomers or diastereomers. N-methyl analogs with formula 2.1 and 2.6 may be synthesized from the NH analogs 2.3 and 2.5, respectively, by reductive amination with formaldehyde, aldehydes, sodium acetate and sodium cynoborohydride at room temperature.

SCHEME 2

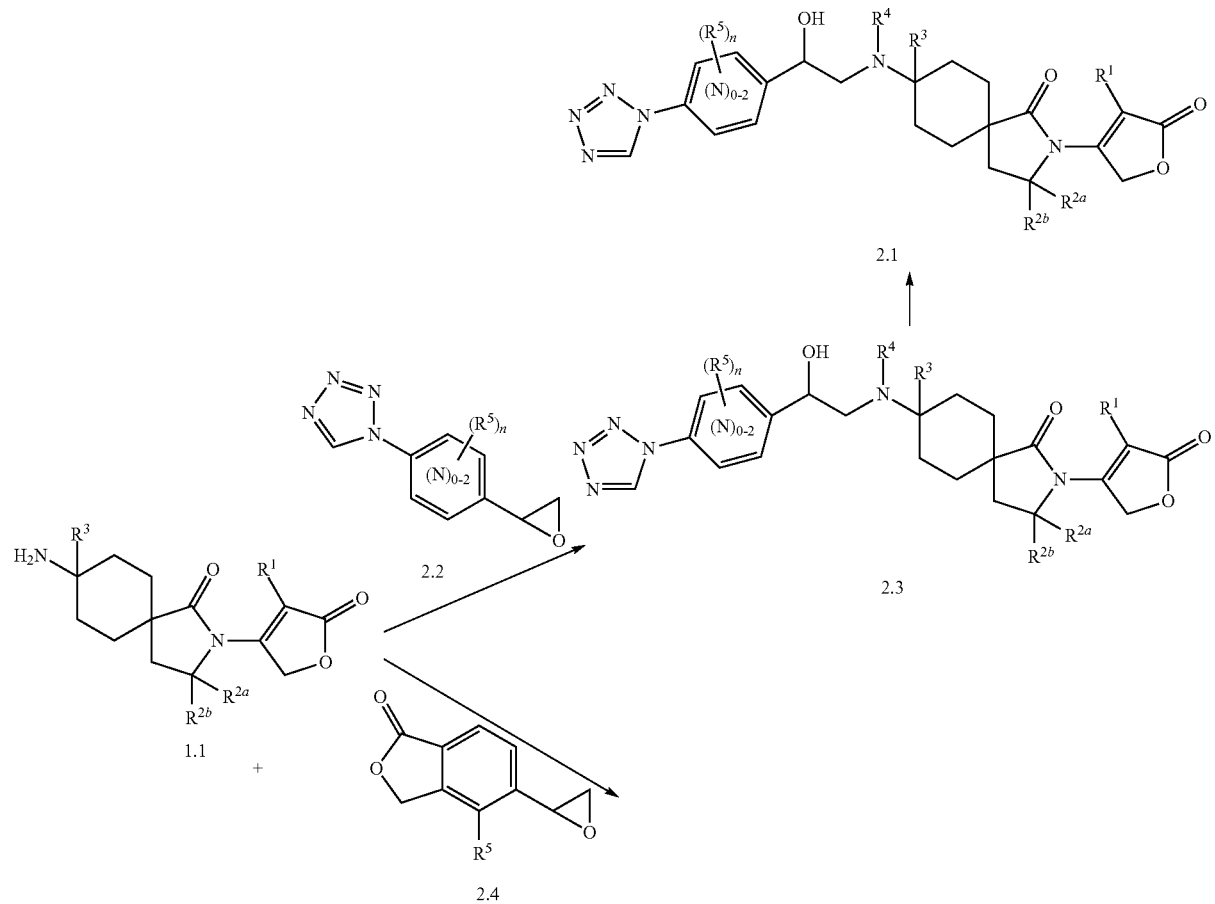

-continued

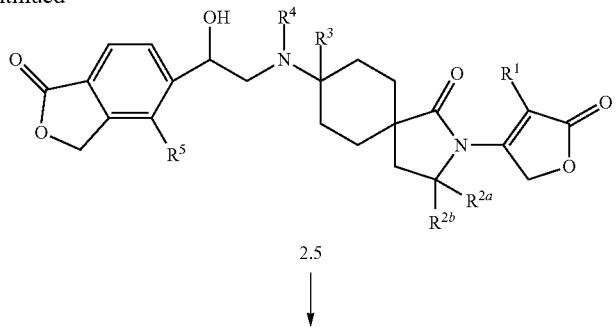

2.5

↓

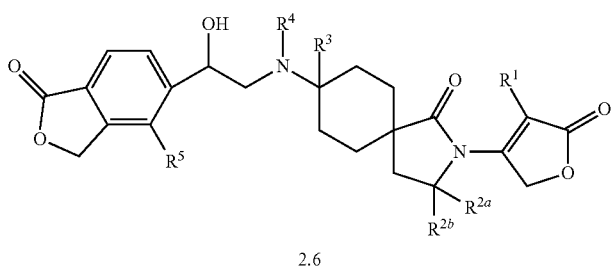

2.6

Preparation of tetrazole-aldehyde intermediates of type 3.5 may start from halo-substituted aniline 3.1 (Scheme 3, X=halo, OTf). Thus, formation of the tetrazole ring can be accomplished by stirring $CF_3CO_2TMS$, $N_3TMS$ and $CH(OEt)_3$ in ethyl acetate or $NaN_3$ and $CH(OEt)_3$ in acetic acid at room temperature. This is followed by treatment of tetrazole intermediate 3.2 (where X is chloride, bromide, iodide, OTf) with potassium vinyl trifluoroborate (Molander, G.; Luciana, A. Journal of Organic Chemistry, 2005, 70(10), 3950-3956) under palladium catalyzed coupling conditions. The styrene 3.4 can be directly converted into aldehydes 3.5 by oxidation, for example with $NaIO_4$/$OsO_{4cat}$. The styrene 3.4 can also be transformed to aldehydes of formula 3.5 by epoxidation for example with NBS/NaOH or mCPBA. Ring opening of epoxides of type 3.7 by water followed by oxidation for example with $NaIO_4$ to afford aldehyds of formula 3.5.

SCHEME 3

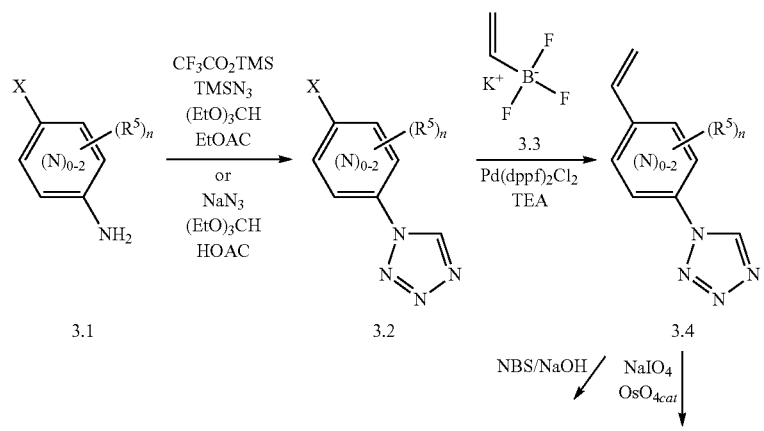

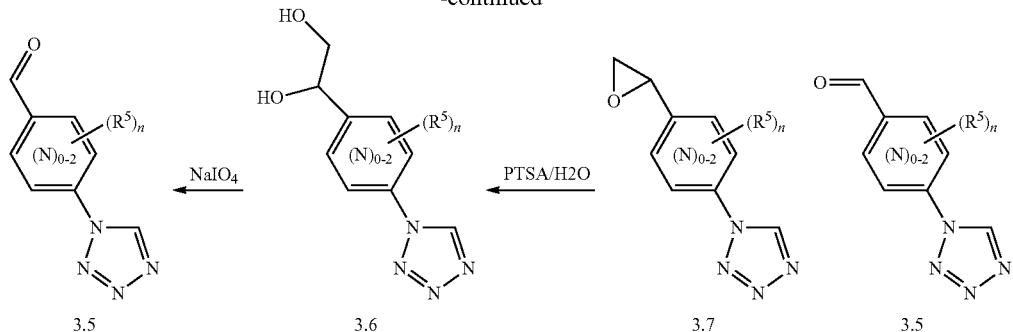

Tetrazole ketone can be prepared as shown in Scheme 4. Treatment of 4.1 (where X is bromide or iodide or OTf) with commercially available alkenyl butylether 4.2 under palladium catalyzed conditions with a suitable ligand (for example Pd(OAc)$_2$, DPPP) can provide the enol ether 4.3. Enol ethers may also be prepared using other methods known in the art. Hydrolysis of 4.3 in acidic aqueous gives the desired compounds of type 4.4.

SCHEME 4

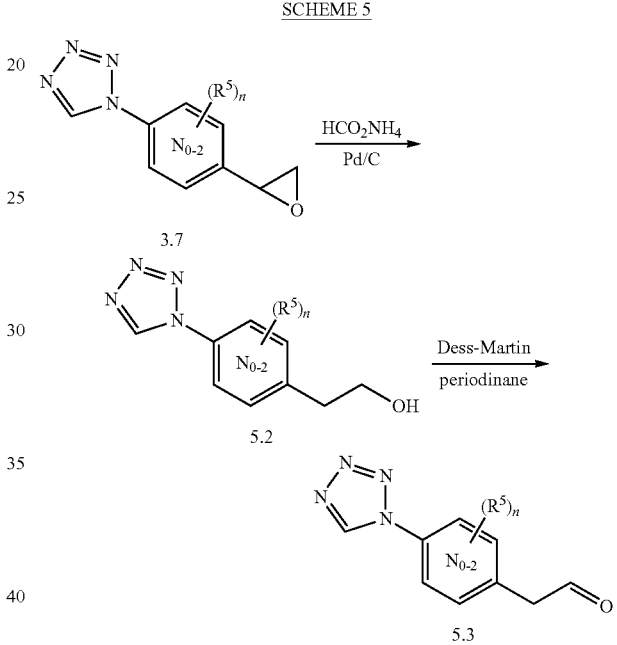

Aldehydes of type 5.3 can be prepared in numerous ways. Scheme 5 describes a method from epoxide 3.7 (Scheme 3) that can be converted to aldehyde 5.3 by reduction of epoxides 3.7 for example with HCO$_2$NH$_4$/Pd/C or hydrogenation followed by oxidation for example with Dess-Martin periodinane.

Epoxides 6.3 (and single enantiomers (R)-6.5 and (S)-6.6) can be prepared following the method detailed in Scheme 6. Treatment of 6.1 (where X is chloride, bromide, iodide, or trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 6.2 (Molander, G.; Brown, A. Journal of Organic Chemistry, 2006, 71(26), 9681-9686). Alternatively, other methods may be employed, for example, using vinylstannane reagents and palladium catalysis. The resulting styrenes 6.2 can be converted to the corresponding epoxides 6.3 under various epoxidation conditions, for example, with m-CPBA (Fringuelli, F. et al. Organic Preparations and Procedures International, 1989, 21(6), 757-761). The racemic epoxide 6.3 can be resolved under chiral HPLC chromatography conditions to afford its enantiomers 6.5 and 6.6, which can be used in place of 6.3 according to Scheme 1. Styrene 6.2 can also be converted to aldehyde 6.4 by oxidation (for example, NaIO4-OsO4).

SCHEME 6

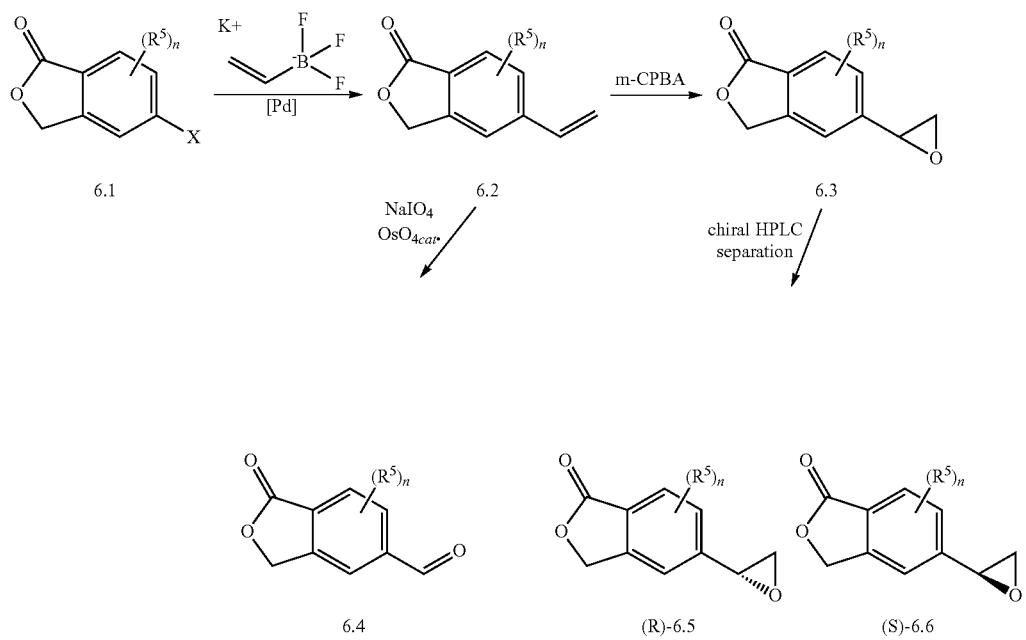

Aldehydes 7.3 may be prepared in many ways, with two approaches described in Scheme 7. Treatment of 6.4 (where X is bromide, iodide, or trifluoromethane sulfonate) with bromo(1,3-dioxolan-2-ylmethyl)zinc in the presence of an appropriate palladium catalyst and ligand, such as palladium (II) acetate and tri-t-butylphosphine-BF4 complex, provides the corresponding aryl 1,3-dioxolan-2-ylmethyl derivative 7.2. Then the aldehyde 7.3 may be obtained by treatment with HCl in the presence of water and an organic solvent. Alternatively, reaction of 6.4 (where X is bromide, iodide, or trifluoromethane sulfonate) with allyltributylstannane in the presence of palladium catalyst affords the allyl product 7.4. Oxidation, for example with ozone, followed by dimethyl sulfide, provides aldehydes 7.3.

Aldehydes of type 8.6 can be synthesized from bromides of type 8.1. Bromination on the benzylic position of starting material 8.1 (where X is chloride, bromide, iodide, or trifluoromethane sulfonate) followed by nucleophilic substitution reaction of the formed bromide with sodium azide to afford azide 8.3. Ring closure of 8.3 can be accomplished by stirring in TFA to give tricycles of type 8.4. Treatment of 8.4 with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 8.5 (Molander, G.; Brown, A. Journal of Organic Chemistry, 2006, 71(26), 9681-9686).

SCHEME 7

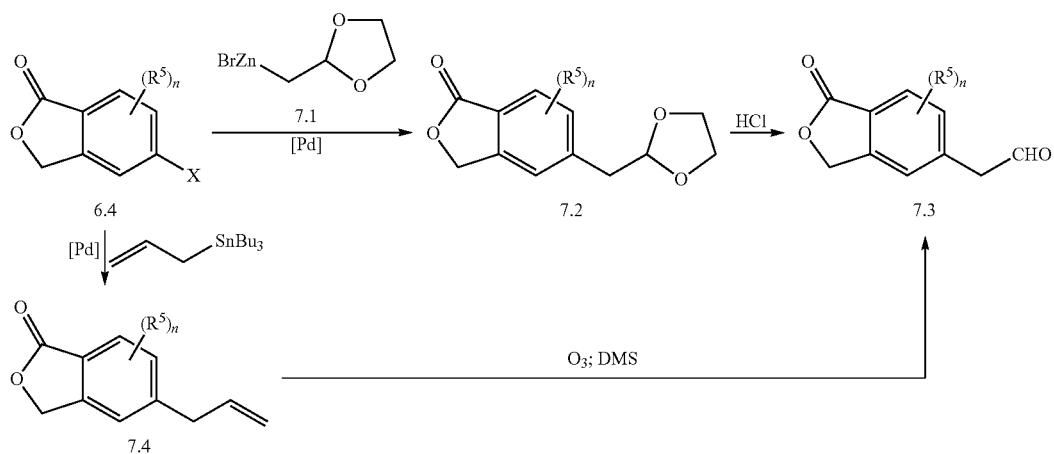

X = Br, OTf

Oxidative cleavage, employing, for example, osmium tetroxide and sodium periodate provides aldehydes of type 8.6.

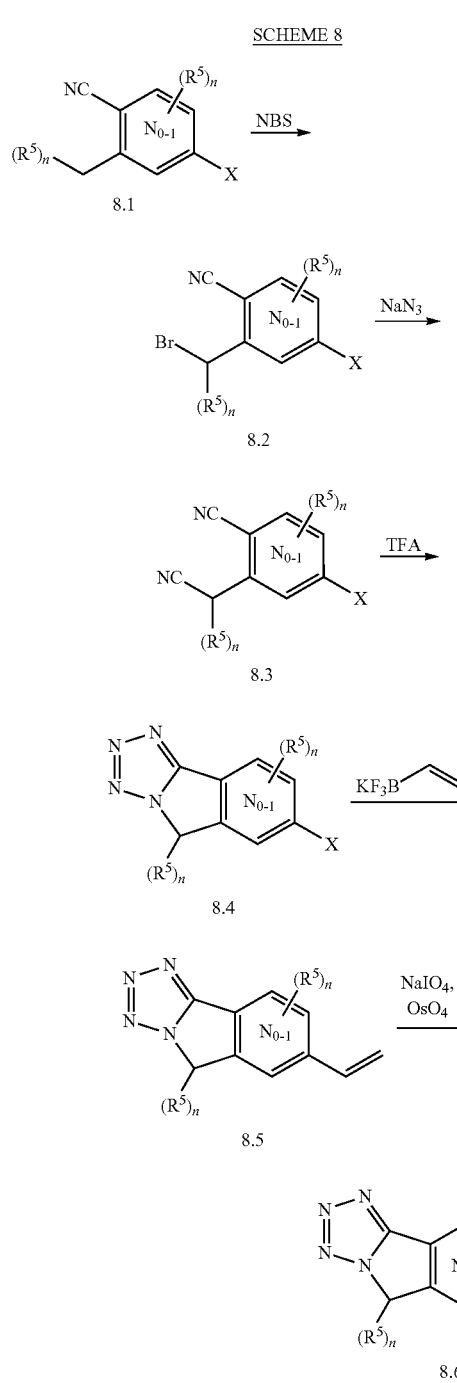

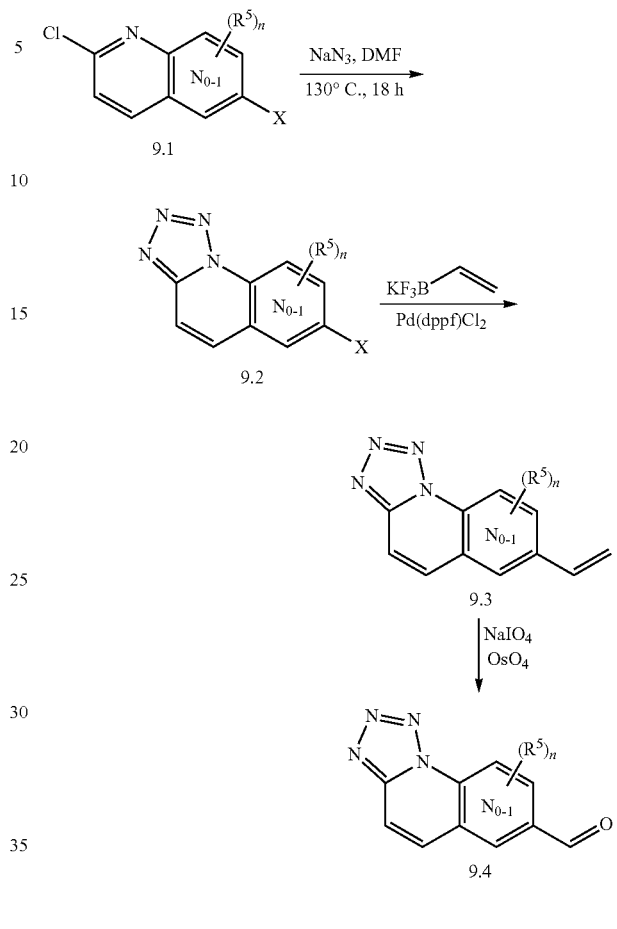

Aldehydes of type 9.4 can be synthesized from quinolines of type 9.1 (where X is chloride, bromide, iodide, or trifluoromethane sulfonate). Condensation of quinoline 9.1 with sodium azide in DMF at 130° C. produces tetrazoles of type 9.2. Treatment of 9.2 with commercially available potassium vinyl trifluoroborate under palladium catalyzed coupling conditions with an appropriate phosphine ligand gives rise to styrene 9.3. Oxidative cleavage, employing, for example, osmium tetroxide and sodium periodate provides aldehydes of kind 9.4.

Scheme 10 describes synthesis of aldehydes of type 10.4. Tetrahydroquinolone 10.1 (where X is chloride, bromide, iodide, or trifluoromethane sulfonate) was reacted with DPPA in the presence of DIAD and (2-pyridyl)PPh$_2$ to give tetrazoles of 10.2. Treatment of 10.2 with commercially available potassium vinyl trifluoroborate under palladium catalyzed coupling conditions with an appropriate phosphine ligand gives rise to styrene 10.3. Oxidative cleavage, employing, for example, osmium tetroxide and sodium periodate provides aldehydes of type 10.4.

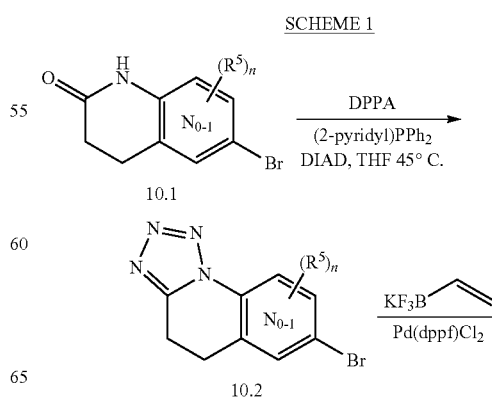

-continued

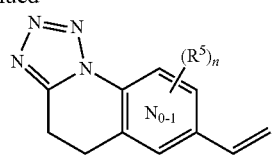

10.3

↓ NaIO₄
  OsO₄

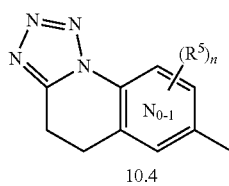

10.4

The iso-tetrazole aldehydes of type 11.3 can be prepared from commercially available iso-tetrazoles of type 11.1 (where X is chloride, bromide, iodide, OTf) using the same procedure as shown in Scheme 3. The tetrazole amines of type 11.6 can be prepared from chlorides of type 11.4 with nitrile substituent. Treatment of chlorides of 11.4 with tetrazole and a base such as $Cs_2CO_3$ afford tetrazoles of type 11.5 as the major isomer. Reduction of the nitrile with, for example, hydrogenation over Reney Ni produces the desired amines of type 11.6.

SCHEME 11

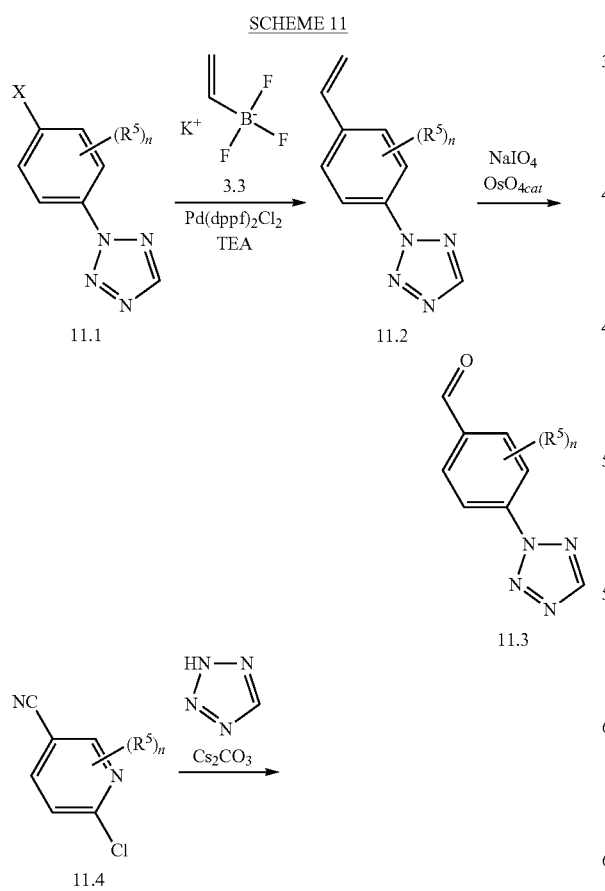

-continued

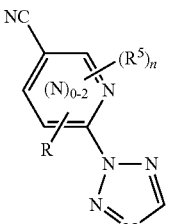

11.5

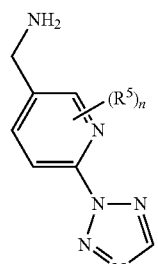

11.6

Spirocyclic lactams of type 12.4, can be prepared in numerous ways, including those described in Scheme 12. Commercially available ketoesters 12.1 can be protected as ketals (12.2), then alkylated with bromoacetonitrile using a base such as lithium diisopropylamide to afford nitrile intermediates of type 12.3. Reduction, for example using Reney Ni or platinum oxide and hydrogen, affords lactams of type 12.4.

SCHEME 12

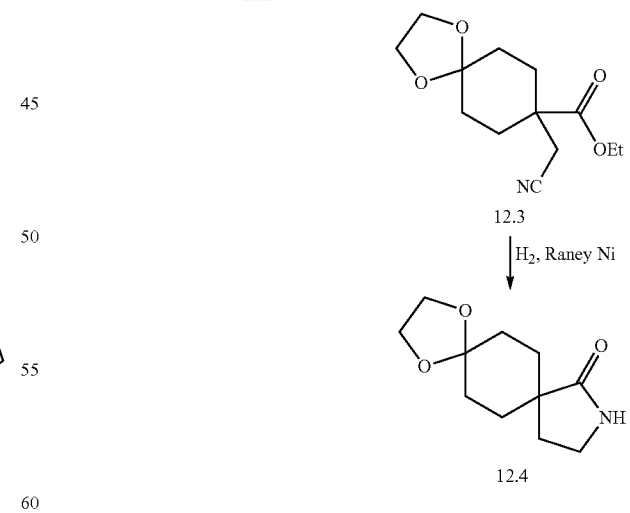

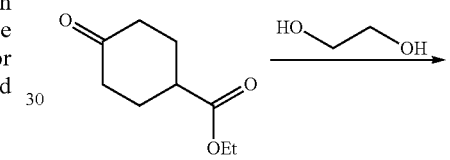

Alternatively, ketal-esters may be alkylated with allylic halides 13.2 using a base such as lithium diisopropylamide to furnish allyl intermediates 13.3. Oxidative cleavage, employing, for example, osmium tetroxide and sodium periodate provides ketones or aldehydes 13.4. Reductive amination of the ketone or aldehyde by, for example, ammonium acetate and sodium cynoborohydride or hydoxyamine followed by hydrogenation over palladium gives lactams of type 13.6.

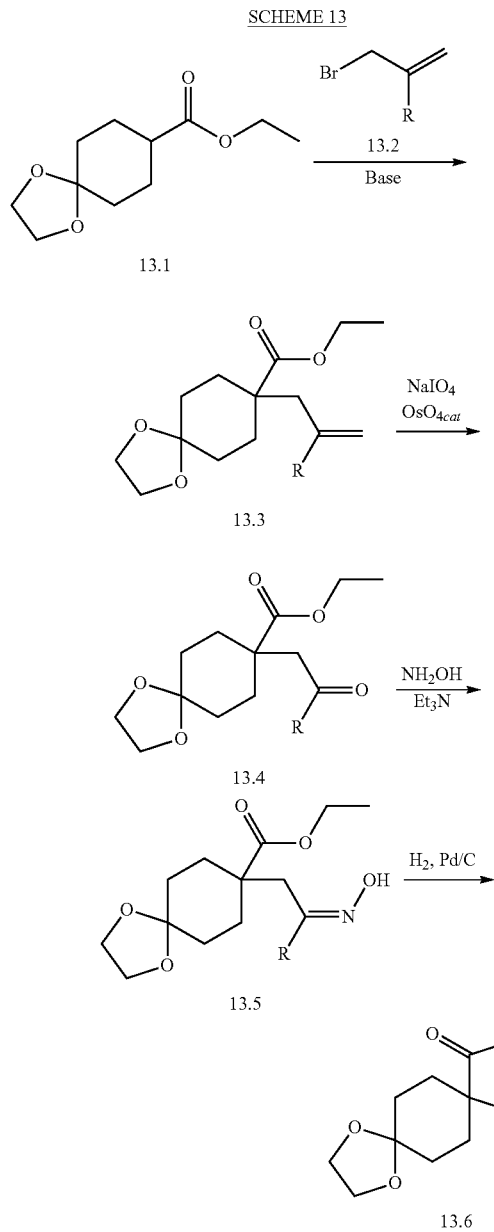

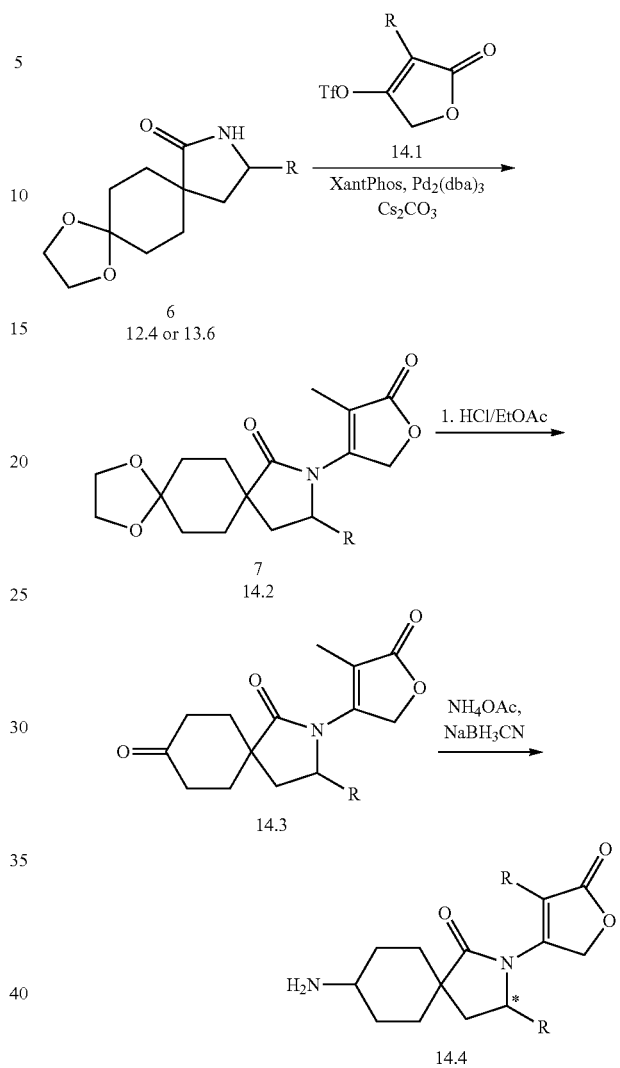

Spirocyclic aminofuranones 14.4 can be prepared as described in Scheme 14. Spirocyclic lactams 12.4 or 13.6, can be coupled to furanone triflates or bromides 14.1 using a palladium catalyst and ligand, for example palladium acetate and 4,5-Bis(diphenylphosphino)-9,9-dimethylxanthene to give Intermediates of type 14.2. Intermediates 14.2 with R group may be separated by chiral HPLC, then are converted to spirocyclic aminofuranones 14.4 by removal of the protective group followed by reductive amination with ammonium acetate and sodium cynoborohydride. The mixture of two isomers can be separated by chiral HPLC. The enantiomerically pure isomers of 14.4 can also be made by enzyme catalyzed reductive amination.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated.

Reactions sensitive to moisture or air were performed under nitrogen or argon using anhydrous solvents and reagents. The progress of reactions was determined by either analytical thin layer chromatography (TLC) usually performed with E. Merck™ pre-coated TLC plates, silica gel 60E-254, layer thickness 0.25 mm or liquid chromatography-mass spectrometry (LC-MS).

Typically the analytical LC-MS system used consisted of a Waters ZQ platform with electrospray ionization in positive ion detection mode with an AGILENT 1100 series HPLC with autosampler. The column was usually a Water XTERRA MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters SUNFIRE C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a BIOTAGE (Uppsala, Sweden) Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as AN internal reference in $CD_3OD$ solutions. Coupling constants (J) were reported in hertz (Hz).

Chiral analytical chromatography was usually performed on one of CHIRALPAK AS, CHIRALPAK AD, CHIRALCEL OD, CHIRALCEL IA, or CHIRALCEL OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of CHIRALPAK AS, CHIRALPAK AD, CHIRALCEL OD, Ciralcel IA, or CHIRALCEL OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was by supercritical fluid (SFC) conditions using one of CHIRALPAK AS, CHIRALPAK AD-H, CHIRALCEL OD-H, CHIRALPAK IC, or CHIRALCEL OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used. Concentration of solutions was generally carried out on a rotary evaporator under reduced pressure Abbreviations and acronyms that may be used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); benzyl (Bn); t-butyloxycarbonyl (Boc or BOC); di-t-butyl dicarbonate ((BOC)$_2$O, Boc$_2$O); benzyloxycarbonyl (Cbz); Cyclopentyl methyl ether (CPME); Carbonyldiimidazole (CDI); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); diethyl amine (DEA); dimethoxyethane (DME); Diisopropylazodicarboxylate (DIAD); Diisobutylaluminium hydride (DIBAL-H); N,N-diisopropylethylamine (DIEA, DIPEA, Hunig's base); dioxine is 1,4-dioxane; di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3(1H)-one); dimethylsulfide (DMS); dimethylsulfoxide (DMSO); N,N-dimethylformamide (DMF); 4-dimethylaminopyridine (DMAP); dimethylacetamide (DMA; DMAC); 1,3-Bis(diphenylphosphino)propane (DPPP); (Oxydi-2,1-phenylene)bis(diphenylphosphine) (DPEPhos); Diphenylphosphoryl azide (DPPA); ethyl acetate (EtOAc or EA); diethyl ether (ether or Et$_2$O); 1-ethyl-3-(3-dimethylaminopropyl)carbodiimide (EDC, EDAC or EDCI); 2-(7-Aza-1H-benzotriazole-1-yl)-1,1,3,3-tetramethyluronium hexafluorophosphate (HATU); hexane (Hex); hexamethylphosphoramide (HMPA); 1-Hydroxybenzotriazole hydrate (HOBt); isopropanol (IPA); isopropyl acetate (IPAc); Potassium bis(trimethylsilyl)amide (KHMDS); lithium aluminum hydride (LAH); lithium diisopropylamide (LDA); 3-chloroperoxybenzoic acid (mCPBA); methanol (MeOH); $CH_3SO_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hexamethyldisilazide (NaHMDS); sodium triacetoxyborohydride (NaBH(OAc)$_3$); Pyridinium chlorochromate (PCC); phenyl (Ph); petroleum ether (PE or petrol ether); tetrakis(triphenylphosphine)palladium (Pd(PPh$_3$)$_4$); tris(dibenzylideneacetone)dipalladium (Pd$_2$(dba)$_3$); Pd(dppf)Cl$_2$ or PdCl$_2$(dppf) is 1,1'-Bis(diphenylphosphino)ferrocene]dichloropalladium(II) which may be complexed with CH$_2$Cl$_2$; Pyridoxyl phosphate (PLP); tetra-n-butylammonium fluoride (TBAF); tert-butyldimethylsilyl chloride (TBS-Cl); triethylamine (TEA); trifluoroacetic acid (TFA); —SO$_2$CF$_3$ (Tf); trifluoromethanesulfonic acid (triflic acid, TfOH); trifluoromethanesulfonic anhydride (triflic anhydride, (Tf)$_2$O); 2-tetrahydrofuran (THF); N,N,N',N'-Tetramethylethylenediamine (TMEDA); p-toluenesulfonic acid (TsOH or PTSA); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: racemic or racemate (rac.); starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t.

or RT); hour(s) (h or hr); minute(s) (min); retention time (R$_t$); gram(s) (g); milligram(s) (mg); milliliter(s) (mL); microliter(s) (μL); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or stereoconfigurations, or as a mixture of both. In many of the examples for intermediate compounds and final compounds, such compounds having a chiral center were separated into single stereoisomers, for example, referred to as isomer A (or enantiomer A or the like), which refers to the observed faster eluting isomer, and isomer B (or enantiomer B or the like), which referes to the observed slower eluting isomer, and each such isomer may also be noted in the example as either the fast or slow eluting isomer. For illustration, in the example titled "Intermediate 2," the racemic parent title compound would be referred to as Intermediate 2 (or I-2), and the separated stereoisomers are noted as Intermediates 2A and 2B (or I-2A and I-2B). Any intermediates described below may be referred to herein by their number preceded by "I-"; for example, Intermediate 2A is shortened to I-2A. In some examples, compounds having a chiral center were derived synthetically from a single isomer intermediate; e.g., Example 2 was made using stereoisomer I-1B. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

Intermediate 1

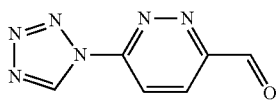

6-(1H-tetrazol-1-yl)pyridazine-3-carbaldehyde

Step A: 3-bromo-6-(1H-tetrazol-1-yl)pyridazine

To a solution of 6-bromopyridazin-3-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min, and this was followed by addition of azidotrimethylsilane (12.09 ml, 92 mmol). Stirring continued at rt for 2 days, and the mixture was concentrated under reduced pressure. Recrystallization of the residue from ethyl acetate afforded 3-bromo-6-(1H-tetrazol-1-yl)pyridazine. LCMS [M+2+1]$^+$=228.9.

Step B: 3-(1H-tetrazol-1-yl)-6-vinylpyridazine

A solution of 3-bromo-6-(1H-tetrazol-1-yl)pyridazine (11.2 g, 49.3 mmol), potassium vinyltrifluoroborate (13.22 g, 99.0 mmol), 1,1'-bis(diphenylphosphino)ferrocene-palladium(ii)dichloride dichloromethane complex (2.01 g, 2.47 mmol), and TEA (13.75 ml, 99.0 mmol) in ethanol (150 ml) was heated at reflux at 82° C. for 4 h. The reaction mixture was cooled to rt, and the precipitate was filtered off. The filtrate was concentrated, and the residue was purified by flash chromatography (BIOTAGE (Uppsala, Sweden), Si, ethyl acetate in hexane) affording 3-(1H-tetrazol-1-yl)-6-vinylpyridazine LCMS [M+H]$^+$=175.10. The filter cake was stirred in DCM (50 mL), and the solid was filtered off. The filtrate was concentrated to afford more 3-(1H-tetrazol-1-yl)-6-vinylpyridazine Method A: Step C
6-(1H-tetrazol-1-yl)pyridazine-3-carbaldehyde To a solution of 3-Vinyl-6-(1H-tetrazol-1-yl)pyridazine (94 mg, 0.54 mmol) in MeOH (20 mL) and H$_2$O (10 mL) were added NaIO$_4$ (462 mg, 2.2 mmol) and OsO$_4$(4 mg, 0.016 mmol). The reaction mixture was stirred at room temperature for 3 hr, and poured into ice water (20 mL). The aqueous extracted with EtOAc (50 mL×2). The combined organic layers were washed with brine (100 mL), dried over anhydrous sodium sulfate, filtered and concentrated. The residue was purified by preparative TLC (petroleum ether: ethyl acetate=1:5) to give the title compound.

Method B: Step C: 3-(oxiran-2-yl)-6-(1H-tetrazol-1-yl)pyridazine

To a suspension of 3-vinyl-6-(1H-tetrazol-1-yl)pyridazine (6.7 g, 38.5 mmol) in a mixture solvent of t-BuOH and water (96 ml: 190 ml) was added N-bromosuccinimide (7.53 g, 42.3 mmol) in portions at rt. The mixture was heated at 50° C. for 1 h, and cooled to 0° C. in an ice bath. NaOH (4.61 g in 30 mL water, 115 mmol) was added dropwise, and the resulting mixture was stirred at the same temperature for 20 min. The product was collected by filtration, washed with water, dried under vacuum to give 3-(oxiran-2-yl)-6-(1H-tetrazol-1-yl)pyridazine LCMS [M+H]$^+$=191.07.

Step D:
6-(1H-tetrazol-1-yl)pyridazine-3-carbaldehyde

To a solution of 3-(oxiran-2-yl)-6-(1H-tetrazol-1-yl) pyridazine (200 mg, 1.05 mmol) in 5 mL of THF and H$_2$O (3:1) was added TsOH.H$_2$O (20 mg, 0.1 mmol). The resulting mixture was heated under reflux overnight, and poured into water. The aqueous layer was washed with EtOAc twice. NaIO$_4$ (205 mg, 0.96 mmol) and acetone (1 mL) were added to the above aqueous solution. The resulting mixture was stirred at room temperature for 4 h, then extracted with EtOAc. The organic layer was washed with brine, dried over anhydrous Na$_2$SO$_4$, filtered and concentrated. The residue was purified by preparative TLC (petroleum ether: EtOAc=1:1) to afford the title compound. $^1$H-NMR (400 MHz, CDCl$_3$) δ ppm 10.43 (s, 1H), 9.86 (s, 1H), 8.51 (d, J=8.8 Hz, 1H), 8.37 (d, J=8.8 Hz, 1H).

The following aldehyde intermediates in Table 1 were prepared employing a synthetic method similar to that described for Intermediate 1.

TABLE 1

Aldehydes prepared using either method A or method B.

| Int # | Starting material and method | Structure and Name | LC-MS [M + H]+ |
|---|---|---|---|
| 2 | (Br-pyridine-NH2) Method B | 6-(1H-tetrazol-1-yl)nicotinaldehyde | 176 |
| 3 | (NH2-pyridine-Br) Method A | 5-(1H-tetrazol-1-yl)picolinaldehyde | 176 |
| 4 | (Br-pyrazine-NH2) Method B | 5-(1H-tetrazol-1-yl)pyrazine-2-carbaldehyde | 177 |
| 5 | (Cl-methylpyridazine-NH2) Method A | 4-methyl-6-(1H-tetrazol-1-yl)pyridazine-2-carbaldehyde | 191 |
| 6 | (Br-methylpyrazine-NH2) Method A | 3-methyl-5-(1H-tetrazol-1-yl)pyridazine-2-carbaldehyde | 191 |
| 7 | (Br-methylpyridazine-NH2) Method A | 5-methyl-6-(1H-tetrazol-1-yl)pyridazine-3-carbaldehyde | 191 |
| 8 | (NH2-phenyl-Br) Method A | 4-(1H-tetrazol-1-yl)benzaldehyde | 175 |
| 9 | (NH2-thiazole-Br) Method A | 2-(1H-tetrazol-1-yl)thiazole-5-carbaldehyde | 182 |

Intermediate 10

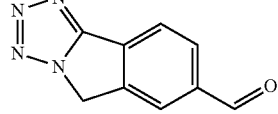

5H-tetrazolo[5,1-a]isoindole-7-carbaldehyde

Step A: 4-bromo-2-(bromomethyl)benzonitrile

A mixture of 4-bromo-2-methylbenzonitrile (15.00 g, 74.2 mmol), NBS (13.87 g, 77.9 mmol) and benzoyl peroxide (0.63 g, 2.60 mmol) in CCl₄ (250 ml) was heated at 80° C. for 6 hr. The suspension was filtered and concentrated. The residue was purified by flash chromatography (EtOAc in petroleum ether: 0 to 10%) to afford the title compound.

Step B: 2-(azidomethyl)-4-bromobenzonitrile

A mixture of 4-bromo-2-(bromomethyl)benzonitrile (17.00 g, 61.83 mmol) and NaN₃ (4.42 g, 68.01 mmol) in DMF (120 mL) was stirred at 25° C. for 16 hr. The mixture was diluted with H₂O (120 mL), extracted with EtOAc (100 mL×3). The combined organic layers were washed with brine (80 mL×5), dried over Na₂SO₄, filtered and concentrated to afford the title compound.

Step C: 7-bromo-5H-tetrazolo[5,1-a]isoindole

A mixture of 2-(azidomethyl)-4-bromobenzonitrile (14.50 g, 61.1 mmol) in TFA (100 mL) was stirred at 18° C. for 2 hr. The mixture was diluted with MeOH (100 mL), filtered and dried (Na₂SO₄) to afford the title compound.

Step D: 7-vinyl-5H-tetrazolo[5,1-a]isoindole

A mixture of 7-bromo-5H-tetrazolo[5,1-a]isoindole (2.00 g, 8.44 mmol), potassium vinyltrifluoroborate (1.36 g, 10.1 mmol), Pd(dppf)Cl$_2$ (614 mg, 0.84 mmol) and triethylamine (1.75 mL, 12.6 mmol) in anhydrous EtOH (60 mL) was heated at reflux for 6 hr under N$_2$. The mixture was concentrated and the residue was purified by flash chromatography (EtOAc in petroleum ether: 0 to 35%) to afford the title compound.

Step E: 5H-tetrazolo[5,1-a]isoindole-7-carbaldehyde

To a solution of 7-vinyl-5H-tetrazolo[5,1-a]isoindole (100 mg, 0.54 mmol) in MeOH (20 mL) and H$_2$O (10 mL) were added NaIO$_4$ (466 mg, 2.2 mmol) and OsO$_4$ (2 mg, 0.008 mmol). The reaction mixture was stirred at room temperature for 3 hr. The reaction mixture was poured into ice water (20 mL) and extracted with EtOAc (50 mL×2). The combined organic layers were washed with brine (100 mL), dried over anhydrous sodium sulfate and filtered. The filtrate was concentrated, and the residue was purified by flash chromatography (0-30% ethyl acetate in petroleum ether) to afford the title compound. $^1$H-NMR (400 MHz, MeOD) δ ppm 10.12 (s, 1H), 8.00 (d, J=7.8 Hz, 1H), 7.87 (s, 1H), 7.75 (d, J=7.8 Hz, 1H), 5.63 (s, 2H), 5.52 (s, 2H). LCMS [M+H]$^+$=187.

The following aldehyde intermediates in Table 2 were prepared employing a synthetic method similar to that described for Int. 10.

TABLE 2

| Int. # | SM | Structure and Name | LC-MS [M + H]$^+$ |
|---|---|---|---|
| 11 | | 6-methyl-5H-tetrazolo[5,1-a]isoindole-7-carbaldehyde | 201 |
| 12 | | 6-fluoro-5H-tetrazolo[5,1-a]isoindole-7-carbaldehyde | 205 |
| 13 | | 8-methyl-5H-tetrazolo[5,1-a]isoindole-7-carbaldehyde | 201 |
| 14 | | 4-methyl-1-oxo-1,3-dihydroisobenzofuran-5-carbaldehyde | 177 |
| 15 | | 5H-tetrazolo[5,1-a]isoindole-8-carbaldehyde | 187 |

Intermediate 16

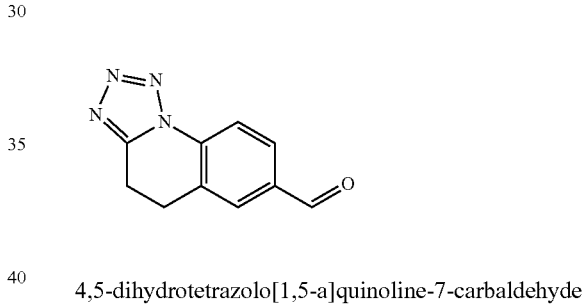

4,5-dihydrotetrazolo[1,5-a]quinoline-7-carbaldehyde

Step A: 7-bromo-4,5-dihydrotetrazolo[1,5-a]quinoline

To a solution of 6-bromo-3,4-dihydroquinolin-2(1H)-one (550 mg, 2.43 mmol) in THF (30 mL) was added triphenylphosphine (2.55 g, 9.73 mmol) and DPPA (2.41 g, 8.85 mmol), DIAD (1.78 g, 8.85 mmol). The mixture was stirred at 45° C. for 18 hr, and concentrated. The residue was purified by flash column chromatography (0-30% EtOAc in petroleum ether) to afford the title compound. $^1$H-NMR (400 MHz, CDCl$_3$) δ ppm 7.89 (d, J=8.2 Hz, 1H), 7.65-7.51 (m, 2H), 3.44-3.30 (m, 2H), 3.23-3.10 (m, 2H).

Step B: 7-vinyl-4,5-dihydrotetrazolo[1,5-a]quinoline

To a solution of 7-bromo-4,5-dihydrotetrazolo[1,5-a]quinoline (530 mg, 2.11 mmol) in EtOH (5 mL) were added potassium vinyltrifluoroborate (340 mg, 2.53 mmol), Pd(dppf)Cl$_2$ (58 mg), and triethylamine (320 mg, 3.17 mmol). The mixture was heated at reflux for 16 hr under N$_2$, cooled down to room temperature, and filtered. The filtrate was concentrated to dryness. The crude material was purified by flash column chromatography (0-20% ethyl acetate in petroleum ether) to afford the title compound. $^1$H-NMR (400 MHz, CDCl$_3$) δ ppm 7.89 (d, J=8.2 Hz, 1H), 7.49-7.31 (m, 2H), 6.66 (dd, J=18 Hz, 11 Hz, 1H), 5.75 (d, J=18 Hz, 1H), 5.30 (d, J=11 Hz, 1H), 3.36-3.21 (m, 2H), 3.17-3.02 (m, 2H).

Step C: 4,5-dihydrotetrazolo[1,5-a]quinoline-7-carbaldehyde

To a solution of 7-vinyl-4,5-dihydrotetrazolo[1,5-a]quinoline (350 mg, 1.77 mmol) in dioxane (12 mL) and H$_2$O (4 mL) were added NaIO$_4$ (1.51 g, 7.06 mmol), and OsO$_4$ (45 mg, 0.18 mmol). The mixture was stirred at room temperature for 5 hr, and extracted with ethyl acetate. The combined organic layers were concentrated. The residue was purified by flash column chromatography (0-20% ethyl acetate in DCM) to afford the title compound. $^1$H-NMR (400 MHz, CDCl$_3$) δ ppm 10.06 (s, 1H), 8.21 (d, J=7.8 Hz, 1H), 8.09-7.92 (m, 2H), 3.51-3.38 (m, 2H), 3.33-3.19 (m, 2H). LCMS [M+H]$^+$=201.

Intermediate 17

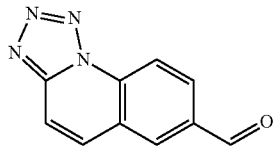 [SMILES: O=Cc1ccc2c(ccc3nnnn32)c1]

tetrazolo[1,5-a]quinoline-7-carbaldehyde

Step A: 7-bromotetrazolo[1,5-a]quinoline

A solution of 6-bromo-2-chloroquinoline (Baston, et al., Eur. J. Med. Chem. 2000, 35, 931-940) (4.00 g, 16.6 mmol) and sodium azide (2.16 g, 3.32 mmol) in 20 mL DMF was stirred at 130° C. for 18 h. The solution was poured into cold water (100 mL) and stirred for 30 min. The solid was collected by filtration, washed with cold water (200 mL), and dried to afford the title compound. MS [M+1]$^+$=248.9.

Step B: 7-vinyltetrazolo[1,5-a]quinoline

To a mixture of 7-bromotetrazolo[1,5-a]quinoline (3.35 g, 13.4 mmol), potassium vinyltrifluoroborate (3.62 g, 8.0 mmol) and Pd(dppf)Cl$_2$ (335 mg, 0.44 mmol) in EtOH (100 mL) was added Et$_3$N (1.31 g, 13.2 mmol). The mixture was heated at 80° C. for 2 hrs, cooled to room temperature and filtered. The solid was rinsed with EtOH. The filtrate was concentrated, and the residue was purified by silica gel chromatography (petroleum ether/EtOAc from 5/1 to 1/1) to afford the title compound. MS [M+1]$^+$=197.1.

Step C: 7-(oxiran-2-yl)tetrazolo[1,5-a]quinoline

A mixture of 7-vinyltetrazolo[1,5-a]quinoline (1.64 g, 8.32 mmol) and N-bromosuccinamide (1.62 g, 9.15 mmol) in a mixture solvent of t-butanol (27.3 mL) and water (54.6 mL) was heated at 40° C. for 2 hrs. A solution of NaOH (998 mg, 25.0 mmol) in water (11 mL) was added slowly at 0° C. The resultant mixture was stirred at the same temperature for 1 hr, concentrated, and purified by silica gel chromatograph (petroleum ether/EtOAc=1/1) to afford the title compound. MS [M+1]$^+$=213.1.

Step D: 1-(tetrazolo[1,5-a]quinolin-7-yl)ethane-1,2-diol

To a solution of 7-(oxiran-2-yl)tetrazolo[1,5-a]quinoline (500 mg, 2.36 mmol) in THF (20 mL) was added 4-methylbenzenesulfonic acid (122 mg, 0.7 mmol) and H$_2$O (63 mg, 3.4 mmol). The mixture was stirred at 60° C. for 20 hr. The reaction was evaporated to dryness to afford the title compound.

Step E: tetrazolo[1,5-a]quinoline-7-carbaldehyde

To a solution of 1-(tetrazolo[1,5-a]quinolin-7-yl)ethane-1,2-diol (470 mg, 2.1 mmol) in acetone (3 mL) and H$_2$O (1 mL) was added NaIO$_4$ (660 mg, 3.1 mmol). The mixture was stirred at room temperature for 16 hr. The reaction was filtered and the filtrate was evaporated. The residue was purified by flash column chromatography (0-30% EtOAc in petroleum ether) to afford the title compound. MS [M+H]$^+$=199.

Intermediate 18

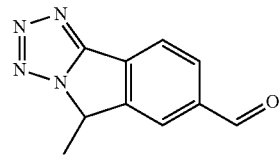

5-methyl-5H-tetrazolo[5,1-a]isoindole-7-carbaldehyde

Step A: 4-bromo-2-ethylbenzonitrile

To a solution of 4-bromo-2-methylbenzonitrile (4.00 g, 20.4 mmol) in THF (40 mL) was added dropwise lithium diisopropylamide (2 M in THF, 16 mL, 32 mmol) in THF (10 mL) over a period of 20 min at −78° C. under nitrogen atmosphere. After stirring 2 hr at the same temperature, iodomethane (3.48 g, 24.5 mmol) was added dropwise over a period of 20 min. The mixture was warmed to room temperature, stirred for 3 h, re-cooled to 0° C. and acidified with 1 N hydrochloric acid. The aqueous layer was extracted with ethyl acetate three times. The combined organic layers were washed with brine, dried over anhydrous sodium sulfate, filtered and concentrated. The residue was purified by flash chromatography (0-10% ethyl acetate in petroleum ether) to afford the title compound. LCMS [M+H]$^+$=210.

Step B: 4-bromo-2-(1-bromoethyl)benzonitrile

A mixture of 4-bromo-2-ethylbenzonitrile (3.50 g, 16.7 mmol) and benzoic peroxyanhydride (0.81 g, 3.33 mmol) in CCl$_4$ (60 mL) was stirred in air at room temperature for 5 minutes. NBS (3.56 g, 20.0 mmol) was added to the above solution. The mixture was stirred at 60° C. for 16 h, cooled to room temperature, and concentrated The residue was purified by flash chromatography (0 to 50% ethyl acetate in petroleum ether) to afford the title compound. MS [M+H]$^+$=288.

Step C: 2-(1-azidoethyl)-4-bromobenzonitrile

To a solution of 4-bromo-2-(1-bromoethyl)benzonitrile (3.20 g, 11.1 mmol) in 10 mL of DMF was added NaN$_3$ (1.44 g, 22.2 mmol). The resulting mixture was stirred at room temperature for 12 hr, poured into water, extracted with EtOAc. The organic layer was dried over $Na_2SO_4$, filtered and concentrated to afford the title compound. MS $[M+H]^+=$ 251.

Step D: 7-bromo-5-methyl-5H-tetrazolo[5,1-c]isoindole

A solution of 2-(1-azidoethyl)-4-bromobenzonitrile (2.60 g, 10.4 mmol) in 15 mL of TFA was stirred at room temperature for 2 hr, and poured into water. The aqueous was extracted with DCM, dried ($Na_2SO_4$), filtered and concentrated. The residue was purified by flash chromatography (0-60% ethyl acetate in petroleum ether) to afford the title compound. $[M+H]^+=251$.

Step E: 5-methyl-7-vinyl-5H-tetrazolo[5,1-a]isoindole

To a solution of 7-bromo-5-methyl-5H-tetrazolo[5,1-a] isoindole (310 mg, 1.23 mmol) in EtOH (5 mL) were added potassium vinyltrifluoroborate (198 mg, 1.48 mmol), Pd(dppf)$Cl_2$ (34 mg), and triethylamine (164 mg, 1.61 mmol). The reaction mixture was heated at reflux for 16 hr under $N_2$, and filtered. The filtrate was concentrated. The residue was purified by flash column chromatography (0-20% ethyl acetate in petroleum ether) to afford the title compound. MS $[M+H]^+=199$.

Step F: 5-methyl-5H-tetrazolo[5,1-a]isoindole-7-carbaldehyde

To a solution of 5-methyl-7-vinyl-5H-tetrazolo[5,1-a] isoindole (200 mg, 1.01 mmol) in dioxane (12 mL) and $H_2O$ (4 mL) were added $NaIO_4$ (863 mg, 4.04 mmol) and $OsO_4$ (26 mg, 0.1 mmol). The mixture was stirred at room temperature for 5 hr, and extracted with ethyl acetate. The organic layer was dried ($MgSO_4$), and concentrated under vacuum. The residue was purified by flash column chromatography (0-40% ethyl acetate in petroleum ether) to afford the title compound as a solid. MS $[M+H]^+=201$.

Intermediate 19

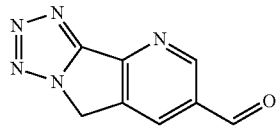 [SMILES: O=Cc1cnc2c(c1)Cn1nnnc1-2]

8H-tetrazolo[1',5':1,2]pyrrolo[3,4-b]pyridine-6-carbaldehyde

Step A: 5-bromo-3-methylpicolinonitrile

A mixture of 2,5-dibromo-3-methylpyridine (20.00 g, 79.7 mmol), CuCN (7.50 g, 83.7 mmol) in 120 mL of DMF was heated at 150° C. for 25 min, cooled down to room temperature, and filtered. The filtrate was diluted by adding $H_2O$ (240 mL) and extracted by EtOAc (80 mL×3). The combined organic layers were concentrated and purified by flash chromatography (0 to 10% EtOAc in petroleum ether) to afford the title compound. MS $[M+H]^+=197$.

Step B: 5-bromo-3-(bromomethyl)picolinonitrile

To a solution of 5-bromo-3-methylpicolinonitrile (2.20 g, 11.2 mmol) and benzoic peroxyanhydride (541 mg, 2.23 mmol) in $CCl_4$ (30 mL) was added NBS (1.87 g, 10.6 mmol). The resulting mixture was heated at 90° C. overnight, and concentrated. The residue was purified by flash chromatography (petroleum ether: EtOAc=5:1) to afford the title compound. MS $[M+H]^+=275$.

Step C: 3-(azidomethyl)-5-bromopicolinonitrile

To a solution of 5-bromo-3-(bromomethyl)picolinonitrile (2.40 g, 8.7 mmol) in DMF (12 mL) was added $NaN_3$ (848 mg, 13.0 mmol). The mixture was stirred at room temperature overnight, and directly used in the next step. MS $[M+H]^+=238$.

Step D: 6-bromo-8H-tetrazolo[1',5':1,2]pyrrolo[3,4-b]pyridine

To a solution of 3-(azidomethyl)-5-bromopicolinonitrile from step C was added TFA (50 mL), The mixture was stirred at room temperature for 3 days, and diluted with MeOH. The precipitate was collected by filtration to afford the title compound. MS $[M+H]^+=238$.

Step E: 6-vinyl-8H-tetrazolo[1',5':1,2]pyrrolo[3,4-b]pyridine

To a solution of 6-bromo-8H-tetrazolo[1',5':1,2]pyrrolo [3,4-b]pyridine (1.00 g, 4.2 mmol) in a mixture solvent of EtOH (20 mL), THF (30 mL) and dioxane (30 mL) were added potassium vinyltrifluoroborate (1.13 g, 8.4 mmol), TEA (851 mg, 8.4 mmol) and Pd(dppf)$Cl_2$ (350 mg). The resulting mixture was heated at 80° C. for 7 hr, concentrated and purified by flash chromatography (0 to 50% DCM in EtOAc) to afford the title compound. MS $[M+H]^+=186$.

Step F: 8H-tetrazolo[1',5':1,2]pyrrolo[3,4-b]pyridine-6-carbaldehyde

To a solution of 6-vinyl-8H-tetrazolo[1',5':1,2]pyrrolo[3, 4-b]pyridine (100 mg, 0.54 mmol) in MeOH (20 mL) and $H_2O$ (10 mL) were added $NaIO_4$ (462 mg, 2.2 mmol) and $OsO_4$(4 mg, 0.016 mmol). The reaction mixture was stirred at room temperature for 3 hr, poured into ice water (20 mL) and extracted with EtOAc (50 mL×2). The combined organic layers were washed with brine (100 mL), dried over anhydrous sodium sulfate, filtered and concentrated. The residue was purified by preparative TLC (petroleum ether: ethyl acetate=1:5) to give the title compound. MS $[M+H]^+=$ 188.

Intermediate 20

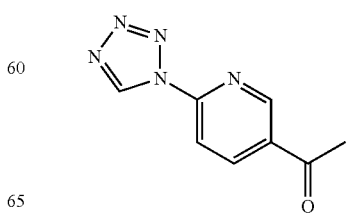

49

1-(6-(1H-tetrazol-1-yl)pyridin-3-yl)ethanone

Step A: 3-bromo-6-(1H-tetrazol-1-yl)pyridine

To a solution of 6-bromopyridin-3-amine (10.75 g, 57.5 mmol) in ethyl acetate (150 ml) was added trimethylsilyl 2,2,2-trifluoroacetate (16.88 ml, 98 mmol). After the mixture was stirred for 5 min at room temperature, triethoxymethane (17.21 ml, 103 mmol) was added. The resulting mixture was stirred for another five min, then azidotrimethylsilane (12.09 ml, 92 mmol) was added. Stirring continued at room temperature for 2 days, and the mixture was concentrated under reduced pressure. Recrystallization of the residue from ethyl acetate afforded the title compound.

Step B: 1-(6-(1H-tetrazol-1-yl)pyridin-3-yl)ethanone

To a solution of 3-bromo-6-(1H-tetrazol-1-yl)pyridine (2.00 g, 8.85 mmol), and Pd(PPh$_3$)$_2$Cl$_2$ (621 mg, 0.88 mmol) in 50 mL of dioxane was added tributyl(1-ethoxyvinyl) stannane (4.80 g, 13.3 mmol). The resulting mixture was heated under reflux overnight, and concentrated. The residue was stirred with HCl/THF (50 mL) at room temperature for 4 hr, and concentrated to afford the title compound. LCMS [M+H]$^+$=190.

TABLE 3

Ketones prepared using the method described for Int. 20.

| Int. # | SM | Structure and Name | LC-MS [M + H]$^+$ |
|---|---|---|---|
| 21 | 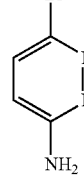 | 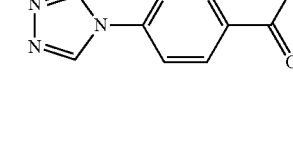 | 191 |
| 22 | 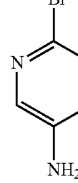 | 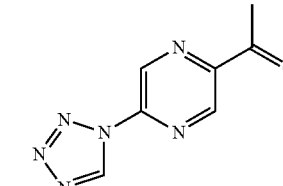 | 191 |
| 23 | 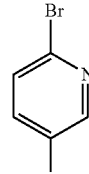 | 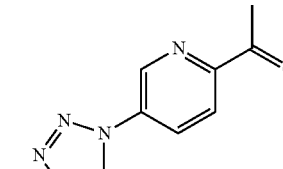 | 190 |
| 24 | 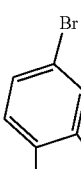 | 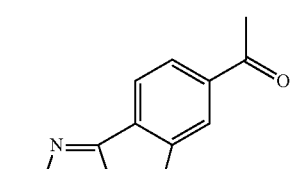 | 201 |
| 25 | 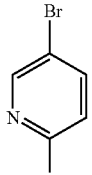 | 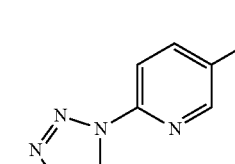 | 190 |
| 26 | 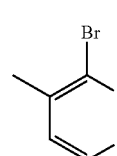 | 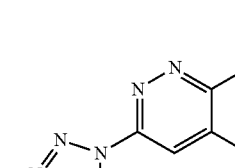 | 205 |
| 27 | 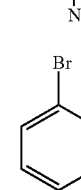 | 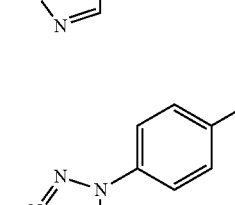 | 189 |
| 28 | 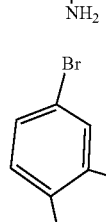 | 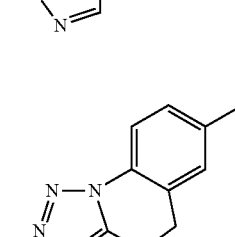 | 215 |

Intermediate 29A

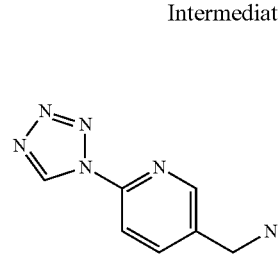

(S)-2-(6-(1H-tetrazol-1-yl)pyridin-3-yl)-2-amino ethanol

Step A: 5-bromo-2-(1H-tetrazol-1-yl)pyridine

To a solution of 6-bromopyridin-3-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min. This was followed by addition of azidotrimethylsilane (12.09 ml, 92 mmol). Stirring continued at rt for 2 days. The mixture was concentrated under reduced pressure. Recrystallization of the residue from ethyl acetate afforded the title compound. MS [M+2+1]$^+$=227.9.

Step B: 2-(1H-tetrazol-1-yl)-5-vinylpyridine

A solution of 5-bromo-2-(1H-tetrazol-1-yl)pyridine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) was heated at reflux at 82° C. for 4 h. The reaction mixture was cooled to room temperature, and the precipitate was filtered off. The filtrate was concentrated. The residue was purified by flash chromatography (BIOTAGE (Uppsala, Sweden), Si, ethyl acetate in hexane: 35 to 45%) affording the title compound MS [M+H]$^+$=176.10

Step C: (R)-5-(oxiran-2-yl)-2-(1H-tetrazol-1-yl) pyridine

To a suspension of 2-(1H-tetrazol-1-yl)-5-vinylpyridine (6.7 g, 38.5 mmol) in a mixture solvent of t-BuOH and water (96 ml: 190 ml) was added N-bromosuccinimide (7.53 g, 42.3 mmol) in portions at rt. The mixture was heated at 50° C. for 1 hr, and cooled to 0° C. in an ice bath. NaOH (4.61 g in 30 mL water, 115 mmol) was added dropwise. The resulting mixture was stirred at the same temperature for 20 min. The product was collected by filtration, washed with water, dried under vacuum to give (R)-5-(oxiran-2-yl)-2-(1H-tetrazol-1-yl)pyridine. LCMS [M+H]$^+$=190.07. The mixture was separated by chiral HPLC to give the title compound.

Step D: (S)-2-(6-(1H-tetrazol-1-yl)pyridin-3-yl)-2-azidoethanol

To a solution of (R)-5-(oxiran-2-yl)-2-(1H-tetrazol-1-yl)pyridine (3.00 g, 15.9 mmol) and LiClO$_4$ (24.90 g, 0.234 mol) in acetonitrile (200 mL) was added sodium azide (4.10 g, 63.1 mmol). The mixture was stirred at 60° C. for 16 hr. The suspension was filtered through a pad of CELITE, partitioned between water and ethyl acetate. The organic layer was separated, washed with brine (200 mL), concentrated. The residue was purified by flash chromatography (0-50% EtOAc in petroleum ether) to afford the title compound. MS [M+H]$^+$=233.

Step E: (S)-2-(6-(1H-tetrazol-1-yl)pyridin-3-yl)-2-aminoethanol

To a solution of (S)-2-(6-(1H-tetrazol-1-yl)pyridin-3-yl)-2-aminoethanol (3.00 g, 12.9 mmol) in methanol (100 mL) and ammonia (2 mL) was added Pd/C (300 mg) under nitrogen atmosphere. The suspension was degassed and purged with hydrogen three times. The reaction mixture was stirred under hydrogen (45 psi) at 30° C. for 18 hr. The suspension was filtered through a pad of CELITE, and the filtered cake was washed with methanol several times. The combined filtrate was concentrated in vacuo to afford the title compound. MS [M+H]$^+$=207.

Intermediate 29B

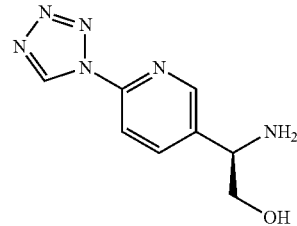 [SMILES: N[C@@H](CO)c1ccc(-n2cnnn2)nc1]

(R)-2-(6-(1H-tetrazol-1-yl)pyridin-3-yl)-2-aminoethanol (R)-2-(6-(1H-tetrazol-1-yl)pyridin-3-yl)-2-aminoethanol was synthesized from (S)-5-(oxiran-2-yl)-2-(1H-tetrazol-1-yl) (intermediate of step C for Int 29A) following the same procedure for Int 29A.

Intermediate 30

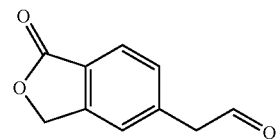 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo (1,3-dioxolan-2-ylmethyl)zinc solution (1.03 L, 516 mmol) was added via cannula and the mixture was again degassed three times. The mixture was then heated at 85° C. for 5 hr. Analysis by HPLC-MS indicated the reaction was not complete. The mixture was stirred at 85° C. for 5 more h. The mixture was then cooled to return to room temperature for overnight. 2-MethylTHF (2 L) and brine were added, and the mixture was stirred for 5 min. The layers were separated and the aqueous layer was extracted again with 2-methylTHF. The organic layers were combined, washed three times with brine (4 L each), dried over MgSO$_4$, filtered, and concentrated. The crude product was purified by flash chromatography (1.5 kg silica cartridge), eluting with 0-20% ethyl acetate in dichloromethane to afford the title compound. MS [M+H]$^+$=221.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 hr. Then the mixture was stirred overnight at room temperature. The mixture was extracted three times with 2 L of ethyl acetate. The combined organic layers were concentrated to give the title compound. MS [M+H]$^+$=177.

Intermediate 31

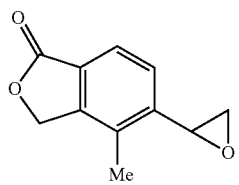 [SMILES: Cc1c(C2CO2)ccc2c1COC2=O]

4-methyl-5-oxiran-2-yl-2-benzofuran-1(3H)-one

Step A: (3-bromo-2-methylphenyl)methanol

To a solution of 3-bromo-2-methyl benzoic acid (35 g, 163 mmol) in THF (200 mL) was added borane THF complex (1.0 M, 212 mL, 212 mmol). The mixture was stirred for 24 hr. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford the title compound. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hr. To this solution was added ethyl acetate to precipitate the salts. The black solution was filtered through a CELITE pad, washed with EtOAc, adsorbed onto silica and purified by silica gel chromatography to afford the title compound. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Step C: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmol), PdCl$_2$(dppf)-CH$_2$Cl$_2$Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield the title compound. MS [M+H]$^+$=175.

Step D: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C., mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield the title compound. MS [M+H]$^+$=191.

Intermediates 31A

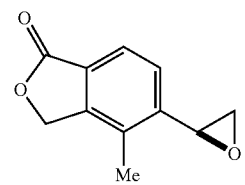 [SMILES: Cc1c([C@H]2CO2)ccc2c1COC2=O]

4-methyl-5-[(2S)-oxiran-2-yl]-2-benzofuran-1(3H)-one

Intermediate 31B

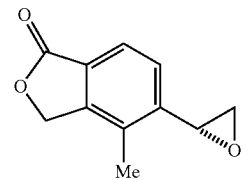 [SMILES: Cc1c([C@@H]2CO2)ccc2c1COC2=O]

4-methyl-5-[(2R)-oxiran-2-yl]-2-benzofuran-1(3H)-one

Racemic 4-methyl-5-oxiran-2-yl-2-benzofuran-1(3H)-one was resolved on a CHIRALPAK® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 ul Injections were spaced every 2.12 mins. (4-methyl-5-[(2R)-oxiran-2-yl]-2-benzofuran-1(3H)-one, 31B) eluted first, and (4-methyl-5-[(2S)-oxiran-2-yl]-2-benzofuran-1(3H)-one, 31A) eluted second.

Alternatively, the resolution could also be achieved using a mobile phase of 8% MeOH/98% CO$_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 31B and by Mosher ester and Trost ester ¹H NMR analysis of esters made starting from 31B. Both epoxide isomers find utility in the present invention.

Intermediate 32

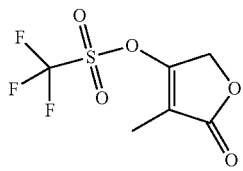

4-Methyl-5-oxo-2,5-dihydrofuran-3-yl trifluoromethanesulfonate

Step A: Ethyl 4-bromo-2-methyl-3-oxobutanoate

To a solution of ethyl 2-methyl-3-oxobutanoate (5.05 g, 35.0 mmol) in water (10 mL) at 0° C. was added bromine (1.805 mL, 35.0 mmol) dropwise over 2 h. The resulting mixture was stirred at room temperature for 16 h, and extracted with ethyl acetate. The organic layer was separated, dried over sodium sulfate, and concentrated in vacuo to give the title compound. ¹H NMR (500 MHz, CDCl₃), δ 4.32-4.27 (m, 2H), 2.455 (s, 2H), 1.99 (s, 3H), 1.337-1.31 (t, 3H).

Step B: 4-Hydroxy-3-methylfuran-2(5H)-one

A mixture of ethyl 4-bromo-2-methyl-3-oxobutanoate (7.81 g, 35 mmol) and hydrogen bromide (0.040 mL, 48%, 0.35 mmol) was heated at 100° C. for 6 h. The precipitate was collected by filtration, and washed with ethyl acetate to give the title compound. ¹H NMR (500 MHz, CDCl₃), δ 4.60 (s, 2H), 3.31 (s, 1H), 1.69 (s, 3H).

Step C: 4-Methyl-5-oxo-2,5-dihydrofuran-3-yl trifluoromethanesulfonate

To a solution of 4-hydroxy-3-methylfuran-2(5H)-one (400 mg, 3.51 mmol) in DCM (10 mL) at −78° C. was added 2,6-lutidine (0.612 mL, 5.26 mmol) and trifluoromethanesulfonic anhydride (0.711 mL, 4.21 mmol) dropwise. The reaction mixture was stirred at −78° C. for 0.5 hr, and at rt for 1 hr. The mixture was diluted with DCM (100 mL), washed with 1 N hydrogen chloride (3×100 mL) and saturated aqueous sodium bicarbonate, dried over sodium sulfate, and concentrated under reduced pressure to give the title compound. LCMS [M+H]⁺=247.0.

Intermediate 33

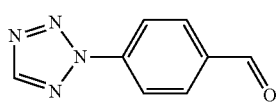

4-(2H-tetrazol-2-yl)benzaldehyde

Step A: 4-(2H-tetrazol-2-yl)phenyl trifluoromethanesulfonate

To the solution of 4-(2H-tetrazol-2-yl)phenol (2.5 g, 15.42 mmol) in DCM (80 ml) was added N-ethyl-N-isopropylpropan-2-amine (4.04 ml, 23.13 mmol) and cooled to −5° C. To the above solution was added trifluoromethanesulfonic anhydride (3.13 ml, 18.50 mmol) dropwise. The resulting solution was stirred at −5° C. for 20 min, then at 0° C. for 1 hr. The reaction was quenched with sat. NaHCO₃. The mixture was partitioned between DCM and sat. NaHCO₃. The organic layer was separated, and the aqueous layer was extracted with DCM four times. The combined organic layers were dried over Na₂SO₄, concentrated to give the title compound. MS [M+H]⁺=295.13.

Step B: 2-(4-vinylphenyl)-2H-tetrazole

A solution of potassium vinyltrifluoroborate (3.23 g, 24.13 mmol) and 4-(2H-tetrazol-2-yl)phenyl trifluoromethanesulfonate (3.55 g, 12.07 mmol) in ethanol (60 ml) was flushed with N₂ for 30 min followed by addition of PdCl₂(dppf)-CH₂Cl₂adduct (0.493 g, 0.603 mmol) and triethylamine (3.36 ml, 24.13 mmol). The resulting mixture was heated at reflux for 4.5 hr under N₂, and filtered. The filtrate was concentrated, and the residue was purified on silica gel column using 20-70% EtOAc/hexane as eluting solvents to give the title compound. LCMS [M+H]⁺=173.2.

Step C: 4-(2H-tetrazol-2-yl)benzaldehyde

To a solution of 2-(4-vinylphenyl)-2H-tetrazole (1.3 g, 7.55 mmol) in dioxane (40 ml) and water (20 ml) was added sodium periodate (3.23 g, 15.10 mmol) and osmium tetroxide (0.047 ml, 0.151 mmol). The resulting mixture was stirred at room temperature under N₂ overnight, quenched with saturated sodium thiosulfate (50 mL), and stirred at rt for 1 hr. The solid was filtered off through CELITE, and the filtrate was concentrated. The residue was partitioned between water and DCM. The organic layer was separated, and the aqueous was extracted with DCM. The combined organic layers were dried over Na₂SO₄, and concentrated to give the title compound. LCMS [M+H]⁺=174.91.

Intermediate 34

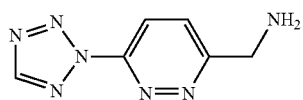 [SMILES: NCc1ccc(-n2ncnn2)nn1]

(6-(2H-tetrazol-2-yl)pyridazin-3-yl)methanamine

Step A: 6-(2H-tetrazol-2-yl)pyridazine-3-carbonitrile

To a solution of 2H-tetrazole (1.831 g, 26.1 mmol) in DMF (30 ml) was added Cs₂CO₃ (8.52 g, 26.1 mmol) at 0° C. The resulting solution was stirred at 0° C. for 15 min followed by addition of 6-chloropyridazine-3-carbonitrile (Liu, et al., *J. Med. Chem.* 2007, 50, 3086-3100) (3.04 g, 21.79 mmol). The resulting solution was stirred at rt for 30 min, then heated at 90° C. for 30 min. The mixture was cooled to rt, and partitioned between EtOAc and sat. NaHCO₃. The organic layer was washed with sat.NaHCO₃ three times, dried over Na₂SO₄, and concentrated. The residue was stirred with DCM. The solid was collected by filtration to give the title compound.

Step B: tert-butyl ((6-(2H-tetrazol-2-yl)pyridazin-3-yl)methyl)carbamate

To a solution of 6-(2H-tetrazol-2-yl)pyridazine-3-carbonitrile (1 g, 5.78 mmol) in MeOH (40 ml) were added (BOC)₂O (1.609 ml, 6.93 mmol) and nickel (0.339 g, 5.78 mmol). The resulting mixture was subjected to hydrogenation at 38 psi for 24 hr. The catalyst was filtered off through CELITE under N₂. The filtrate was concentrated, and the residue was purified on silica gel column using EtOAc/hexane as eluting solvents to give tert-butyl ((6-(2H-tetrazol-2-yl)pyridazin-3-yl)methyl)carbamate. LCMS [M+H]⁺ =278.34.

Step C: (6-(2H-tetrazol-2-yl)pyridazin-3-yl)methanamine

To a solution of tert-butyl ((6-(2H-tetrazol-2-yl)pyridazin-3-yl)methyl)carbamate (0.84 g, 3.03 mmol) in CH₂Cl₂ (6 ml) was added thioanisole (2.150 ml, 18.18 mmol) and TFA (4.67 ml, 60.6 mmol) at 0° C. The resulting solution was stirred at 0° C. for 2 hr, then rt for 2 hr, and concentrated. The residue was loaded into ion-exchange column eluting with MeOH followed by 1 N NH₃/MeOH to give the title compound.

Intermediate 35

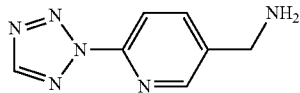

(6-(2H-tetrazol-2-yl)pyridin-3-yl)methanamine (6-(2H-tetrazol-2-yl)pyridin-3-yl)methanamine was synthesized from 6-chloropyridine-3-carbonitrile and 2H-tetrazole following the same procedure for Int. 34.

Intermediate 36

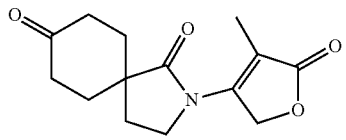 [SMILES: CC1=C(N2CCC3(CCC(=O)CC3)C2=O)COC1=O]

2-(4-methyl-5-oxo-2,5-dihydrofuran-3-yl)-2-azaspiro[4.5]decane-1,8-dione

Step A: Ethyl 1,4-dioxaspiro[4.5]decane-8-carboxylate

A mixture of ethyl 4-oxocyclohexanecarboxylate (54.80 g, 0.322 mol), ethane-1,2-diol (21.30 g, 0.354 mol), and 4-methylbenzenesulfonic acid (0.61 g, 3.20 mmol) in toluene (240 mL) was heated under reflux for 20 hr with azeotropic removal of water. After cooling to room temperature, the mixture was poured into ice water and basified with 1 M sodium hydroxide solution to pH=9. The aqueous layer was extracted with ethyl acetate twice. The organic layers were collected and washed with brine, dried over anhydrous sodium sulfate, filtered and concentrated. The residue was purified by flash chromatography (0-5% ethyl acetate in petroleum ether) to afford the title compound. MS [M+H]⁺ =215.

Step B: Ethyl 8-(cyanomethyl)-1,4-dioxaspiro[4.5]decane-8-carboxylate

To a solution of ethyl 1,4-dioxaspiro[4.5]decane-8-carboxylate (39.00 g, 0.182 mol) in THF (100 mL) was added dropwise lithium diisopropylamide (2 M in THF, 184 mL, 0.364 mol) in THF (200 mL) over a period of 45 min at −78° C. under nitrogen atmosphere. The mixture was stirred for 2 hr at the same temperature. 2-Bromoacetonitrile (34.6 mL, 0.445 mol) was added to the above solution dropwise over a period of 30 min at −78° C. The reaction mixture was warmed to room temperature, stirred at rt for another 18 hr, and acidified with 1 M hydrochloric acid to pH=1 at 0° C. EtOAc (60 ml) was added, and the organic layer was separated. The aqueous layer was extracted with ethyl acetate three times. The combined organic layers were washed with brine, dried over anhydrous sodium sulfate, filtered and concentrated. The residue was purified by flash chromatography (0-10% ethyl acetate in petroleum ether) to afford the title compound. MS [M+H]⁺=254.

Step C: 2-Azaspiro[4.5]decane-1,8-dione

To a solution of ethyl 8-(cyanomethyl)-1,4-dioxaspiro [4.5]decane-8-carboxylate (10.00 g, 39.5 mmol) in methanol (150 mL) and ammonia (10 mL) was added Raney Ni (2.00 g) under nitrogen atmosphere. The suspension was degassed and purged with hydrogen several times. The reaction mixture was stirred under hydrogen (3 atms) at 80° C. for 18 hr. The suspension was filtered through a pad of CELITE, and the filtered cake was washed with methanol several times. The filtrate was concentrated in vacuo. The residue was diluted with hydrochloric ethyl acetate (4 M, 50 mL) and stirred at room temperature for 2 hr. Removal of the solvent afforded the crude product, which was purified by flash chromatography (0-25% ethyl acetate in petroleum ether) to afford the title compound. MS [M+H]⁺=168.

Step D: 2-(4-Methyl-5-oxo-2,5-dihydrofuran-3-yl)-2-azaspiro[4.5]decane-1,8-dione A 250-mL round bottom flask was charged with 2-azaspiro[4.5]decane-1,8-dione (1.00 g, 5.99 mmol), cesium carbonate (3.00 g, 8.99 mmol), tris(dibenzylideneacetone) dipalladium (120 mg, 0.15 mmol) and Xantphos (260 mg, 0.449 mmol). The flask was degassed and purged with nitrogen. Then dioxane (100 mL) and 4-methyl-5-oxo-2,5-dihydrofuran-3-yltrifluoromethanesulfonate (Intermediate 32, 1.40 g, 5.99 mmol) were added under nitrogen atmosphere. The flask was degassed and refilled with nitrogen several times. The mixture was stirred at 100° C. for 17 hr. The solid was filtered off, and the filtrate was concentrated and purified by flash chromatography (0-100% ethyl acetate in petroleum ether) to afford the title compound as a solid. LCMS [M+H]⁺=264.

Intermediate 37

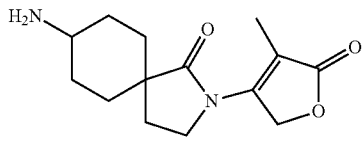 [SMILES: CC1=C(N2CCC3(CCC(N)CC3)C2=O)COC1=O]

8-amino-2-(4-methyl-5-oxo-2,5-dihydrofuran-3-yl)-2-azaspiro[4.5]decan-1-one

Step E: 8-Amino-2-(4-methyl-5-oxo-2,5-dihydrofuran-3-yl)-2-azaspiro[4.5]decan-1-one 2-(4-Methyl-5-oxo-2,5-dihydrofuran-3-yl)-2-azaspiro[4.5]decane-1,8-dione (Intermediate 36, 50 mg, 0.19 mmol) in 5 mL of dry MeOH were added ammonium acetate (29 mg, 0.38 mmol) and sodium cyanoborohydride (30 mg, 0.47 mmol). The resulting mixture was stirred at room temperature overnight. The mixture was concentrated, and the residue was purified by preparative TLC (EtOAc: MeOH=5:1) to afford the title compound as a solid. LCMS [M+H]$^+$= 265.

Intermediate 37A

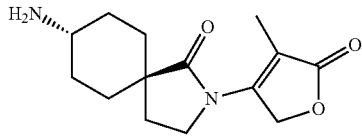 [SMILES: CC1=C(N2CC[C@]3(CC[C@@H](N)CC3)C2=O)COC1=O]

(5r,8r)-8-amino-2-(4-methyl-5-oxo-2,5-dihydrofuran-3-yl)-2-azaspiro[4.5]decan-1-one To a solution of i-PrNH$_2$ (100 mL) in a 0.2 M boric acid solution (200 mL) was adjusted to pH=8.5 with hydrochloric acid. Then a 0.2 M borate buffer (pH 8.5, 1150 mL) was added. Codexis Transaminase panel enzyme P1G5 (available from Codexis, Inc., 200 Penobscot Drive, Redwood City, Calif. 94063, www.codexis.com, tel. 1-650-421-8100) (42.3 g) and PLP (1.35 g) was added to the solution and stirred for 2 h at room temperature. 2-(4-Methyl-5-oxo-2,5-dihydrofuran-3-yl)-2-azaspiro[4.5]decane-1,8-dione (Intermediate 36, 35 g, 0.13 mol) in DMSO (290 mL) was sonicated for 15 min and added drop wise to the enzyme solution at room temperature. The mixture was stirred at 35° C. under N$_2$ steam for 16 hr. The mixture was cooled to room temperature, quenched with CH$_3$CN (1600 mL), and filtered. The filter cake was washed with CH$_3$CN (1600 ml) and water (800 mL) sequentially. The filtrate was charged with K$_2$CO$_3$ (700 g) and the solution was separated. The organic layer was concentrated and the residue was purified by column chromatography to give the title compound. $^1$H NMR: DMSO 400 MHz δ: 7.83 (s, 2H), 5.18 (s, 2H), 4.09 (t, J=7.2 Hz, 2H), 3.00 (m, 1H), 2.02 (t, J=7.2 Hz, 2H), 1.93-1.91 (m, 5H), 1.60-1.49 (m, 6H).

Intermediate 38A

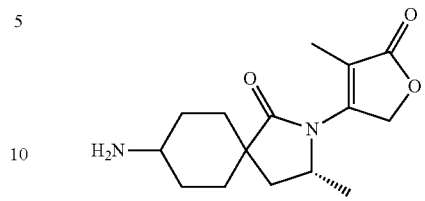

(R)-8-amino-3-methyl-2-(4-methyl-5-oxo-2,5-dihydrofuran-3-yl)-2-azaspiro[4.5]decan-1-one

Intermediate 38B

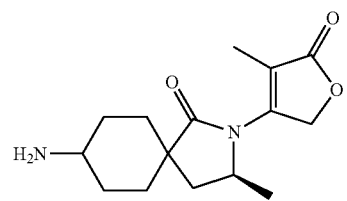 [SMILES: CC1=C(N2C(=O)C3(CCC(N)CC3)C[C@@H]2C)COC1=O]

(S)-8-amino-3-methyl-2-(4-methyl-5-oxo-2,5-dihydrofuran-3-yl)-2-azaspiro[4.5]decan-1-one

Step A: ethyl 1,4-dioxaspiro[4.5]decane-8-carboxylate

A mixture of ethyl 4-oxocyclohexanecarboxylate (67.00 g, 0.393 mol), ethane-1,2-diol (26.88 g, 0.433 mol), 4-methylbenzenesulfonic acid (0.68 g, 3.94 mmol) in toluene (200 mL) was heated under reflux for 20 h with azeotropic removal of water. After cooling to room temperature, the mixture was poured into ice water and basified to pH 9 with 1 M aqueous sodium hydroxide solution. The aqueous layer was extracted with ethyl acetate twice. The organic layers were collected and washed with brine, dried over anhydrous sodium sulfate, filtered and concentrated. The residue was purified by flash chromatography (0-5% ethyl acetate in petroleum ether) to afford the title compound. LCMS [M+H]$^+$=215.

Step B: ethyl 8-allyl-1,4-dioxaspiro[4.5]decane-8-carboxylate

To a solution of ethyl 1,4-dioxaspiro[4.5]decane-8-carboxylate (65.00 g, 0.303 mol) in THF (100 mL) was added dropwise lithium diisopropylamide (2 M in THF, 272 mL, 0.455 mol) in THF (200 mL) over a period of 45 min at −78° C. under nitrogen atmosphere. The mixture was stirred at −78° C. for 2 hr. 2-Bromoacetonitrile (36.5 mL, 0.364 mol) was added dropwise over a period of 30 min at the same temperature. The reaction mixture was warmed to room temperature, stirred for 3 hr at rt, and acidified to pH=1 with 1 M hydrochloric acid at 0° C. The aqueous layer was extracted with ethyl acetate three times. The combined organic layers were washed with brine, dried over anhydrous sodium sulfate, filtered and concentrated. The residue was purified by flash chromatography (0-10% ethyl acetate in petroleum ether) to afford the title compound. LCMS [M+H]+=254.

Step C: ethyl 8-(2-oxopropyl)-1,4-dioxaspiro[4.5]decane-8-carboxylate

A mixture of diacetoxycopper (25.71 g, 0.142 mol) and palladium(II) chloride (5.23 g, 29.49 mmol) in N,N-dimethylacetamide (200 mL) and water (30 mL) was stirred in air for 3 hr. A solution of ethyl 8-allyl-1,4-dioxaspiro[4.5]decane-8-carboxylate (30.00 g, 0.118 mol) in N,N-dimethylacetamide (40 mL) was added to the above solution. The mixture was stirred at room temperature for 20 hr in air, diluted with water and extracted with ethyl acetate (80 mL×3). The organic layers were washed with water, brine, dried (MgSO$_4$), filtered and concentrated in vacuo to afford the title compound. MS [M+H]+=271.

Step D: ethyl 8-(2-(hydroxyimino)propyl)-1,4-dioxaspiro[4.5]decane-8-carboxylate To a solution of ethyl 8-(2-oxopropyl)-1,4-dioxaspiro[4.5]decane-8-carboxylate (23.00 g, 85.08 mmol) in 150 mL of MeOH was added Et$_3$N (25.83 g, 0.255 mol). The reaction was stirred at room temperature for 5 min. Hydroxylamine hydrochloric salt (11.83 g, 0.170 mol) was added to the above mixture. The resulting mixture was heated at 70° C. for 16 hr, cooled to room temperature and concentrated. The residue was purified by flash chromatography (0 to 50% EtOAc in Petroleum Ether) to afford the title compound. MS [M+H]+=286.

Step E: 8,8-ethylenedioxo-3-methyl-2-azaspiro[4.5]decan-1-one

To a solution of ethyl 8-(2-(hydroxyimino)propyl)-1,4-dioxaspiro[4.5]decane-8-carboxylate (13.50 g, 47.31 mmol) in 100 mL of MeOH was added 10% Pd/C (2.80 g). The reaction mixture was stirred at 80° C. for 30 hr under 45 psi of H$_2$, cooled to room temperature, filtered and concentrated. The residue was purified by flash chromatography (0 to 10% MeOH in DCM) to afford the title compound. $^1$H-NMR (400 MHz, MeOD) δ ppm 3.93 (s, 4H), 3.71 (qd, J=13 Hz, 6.7 Hz, 1H), 2.38 (dd, J=13 Hz, 6.7 Hz, 1H), 2.06 (dt, J=13 Hz, 3.7 Hz, 1H), 1.87-1.73 (m, 3H), 1.69-1.43 (m, 5H), 1.22 (d, J=5.9 Hz, 3H).

Step F: 8,8-ethylenedioxo-3-methyl-2-(4-methyl-5-oxo-2,5-dihydrofuran-3-yl)-2-azaspiro[4.5]decan-1-one A 250-mL round bottom flask was charged with 4-methyl-5-oxo-2,5-dihydrofuran-3-yl trifluoromethanesulfonate (Intermediate 32, 2.10 g, 8.52 mmol), cesium carbonate (3.47 g, 10.65 mmol), tris(dibenzylideneacetone) dipalladium (163 mg, 0.18 mmol) and XANTPHOS (308 mg, 0.53 mmol). The flask was degassed and purged with nitrogen. Then dioxane (100 mL) and compound 8,8-ethylenedioxo-3-methyl-2-azaspiro[4.5]decan-1-one (1.60 g, 7.10 mmol) was added under nitrogen atmosphere. The flask was degassed and re-filled with nitrogen several times. The mixture was stirred at 100° C. for 17 hr. The solid was filtered off and the filtrate was concentrated, purified by flash chromatography (0-100% ethyl acetate in petroleum ether) to afford racemic 8,8-ethylenedioxo-3-methyl-2-(4-methyl-5-oxo-2,5-dihydrofuran-3-yl)-2-azaspiro[4.5]decan-1-one as a solid, which separated by SFC to give (R)-8,8-ethylenedioxo-3-methyl-2-(4-methyl-5-oxo-2,5-dihydrofuran-3-yl)-2-azaspiro[4.5]decan-1-one (fast eluted) and (S)-8,8-ethylenedioxo-3-methyl-2-(4-methyl-5-oxo-2,5-dihydrofuran-3-yl)-2-azaspiro[4.5]decan-1-one (slow eluted). CHIRALPAK AD-H 250*4.6 mm I.D., 5 um; Mobile phase: 40% ethanol (0.05% DEA) in CO$_2$; Flow rate: 2.35 mL/min; Wavelength: 220 nm. MS [M+H]+=322.

Step G: (R)-8-amino-3-methyl-2-(4-methyl-5-oxo-2,5-dihydrofuran-3-yl)-2-azaspiro[4.5]decan-1-one (38A)

(R)-8,8-ethylenedioxo-3-methyl-2-(4-methyl-5-oxo-2,5-dihydrofuran-3-yl)-2-azaspiro[4.5]decan-1-one (fast eluting fraction in SFC, 500 mg, 1.56 mmol) was treated with HCl/EtOAc (4 M, 20 mL) by stirring at room temperature for 2 days. The solution was concentrated to obtain the crude product. Then crude ketone compound was dissolved in 20 mL of MeOH followed by addition of NH$_4$OAc (556 mg, 7.21 mmol) and NaBH$_3$CN (181 mg, 2.89 mmol). The reaction mixture was stirred at room temperature overnight, concentrated and the residue was purified by flash chromatography (0 to 13% MeOH in DCM) to afford the title compound. (S)-8-amino-3-methyl-2-(4-methyl-5-oxo-2,5-dihydrofuran-3-yl)-2-azaspiro[4.5]decan-1-one (38B) was afforded from (S)-8,8-ethylenedioxo-3-methyl-2-(4-methyl-5-oxo-2,5-dihydrofuran-3-yl)-2-azaspiro[4.5]decan-1-one using same procedure. MS [M+H]+=278.

Intermediate 39A

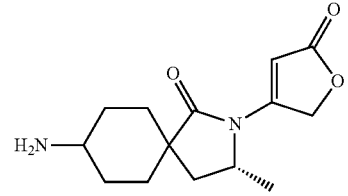 [SMILES: C[C@@H]1CC2(CCC(N)CC2)C(=O)N1C1=CC(=O)OC1]

(R)-8-amino-3-methyl-2-(5-oxo-2,5-dihydrofuran-3-yl)-2-azaspiro[4.5]decan-1-one

Intermediate 39B

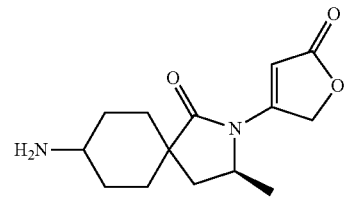 [SMILES: C[C@H]1CC2(CCC(N)CC2)C(=O)N1C1=CC(=O)OC1]

(S)-8-amino-3-methyl-2-(5-oxo-2,5-dihydrofuran-3-yl)-2-azaspiro[4.5]decan-1-one Int. 39A and Int. 39B were prepared following procedure for Int. 38A and Int. 38B, Step F using 4-bromofuran-2(5H)-one (Boukouvalas, et al., *Tetrahedron Lett.* 2007, 48, 105-107).

Intermediate 40A

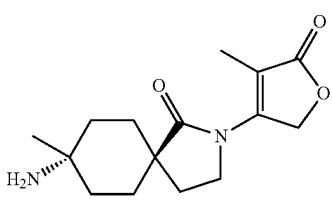 [SMILES: CC1=C(N2CC[C@]3(CC[C@@](C)(N)CC3)C2=O)COC1=O]

(5r,8r)-8-amino-8-methyl-2-(4-methyl-5-oxo-2,5-dihydrofuran-3-yl)-2-azaspiro[4.5]decan-1-one

Intermediate 40B

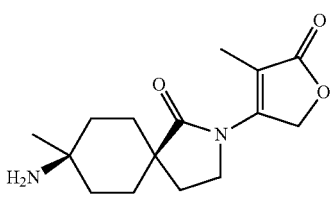 [SMILES: CC1=C(N2CC[C@]3(CC[C@](C)(N)CC3)C2=O)COC1=O]

(5s,8s)-8-amino-8-methyl-2-(4-methyl-5-oxo-2,5-dihydrofuran-3-yl)-2-azaspiro[4.5]decan-1-one Step A: 8-hydroxy-8-methyl-2-(4-methyl-5-oxo-2,5-dihydrofuran-3-yl)-2-azaspiro[4.5]decan-1-one To a solution of 2-(4-methyl-5-oxo-2,5-dihydrofuran-3-yl)-2-azaspiro[4.5]decane-1,8-dione (Intermediate 36, 0.5 g, 1.899 mmol) in THF (9.50 ml) in a dry flask, was added lanthanum trichloride lithium chloride complex in THF (3.17 ml, 1.899 mmol) and stirred for 1 hr at room temperature. The reaction mixture was cooled to 0° C. after 1 hr stirring at room temperature. Methylmagnesium bromide in 2-methyl THF (0.653 ml, 2.089 mmol) was added. The resulting mixture was stirred at room temperature for 2:15 hr. The reaction mixture was quenched with sat. NH$_4$Cl solution and extracted 2 times with EtOAc (few drops of MeOH was added to improve solubility in EtOAc). Combined organic layers were dried over anhydrous MgSO$_4$, filtered, and concentrated. The residue was purified by silica gel column chromatography using (0-10)% MeOH/EtOAc as solvent system to give the title compound. MS [M+H]$^+$=280.2

Step B: 2-chloro-N-(8-methyl-2-(4-methyl-5-oxo-2,5-dihydrofuran-3-yl)-1-oxo-2-azaspiro[4.5]-decan-8-yl)acetamide 8-Hydroxy-8-methyl-2-(4-methyl-5-oxo-2,5-dihydrofuran-3-yl)-2-azaspiro[4.5]decan-1-one (2.1 g, 7.52 mmol) was dissolved in chloroacetonitrile (20 ml). H$_2$SO$_4$ (2.0 ml, 37.5 mmol) was added to the mixture slowly at 0° C. The resulting mixture was stirred at room temperature for 1.5 hr, poured into ice containing solid K$_2$CO$_3$, and extracted with DCM (2 times). Combined organic layers were dried over anhydrous Na$_2$SO$_4$, filtered, and concentrated to get the crude title product, which was taken to the next step without purification. MS [M+H]$^+$=355.2.

Step C: (5r,8r)-8-amino-8-methyl-2-(4-methyl-5-oxo-2,5-dihydrofuran-3-yl)-2-azaspiro[4.5]-decan-1-one & (5s,8s)-8-amino-8-methyl-2-(4-methyl-5-oxo-2,5-dihydrofuran-3-yl)-2-azaspiro-[4.5]decan-1-one 2-Chloro-N-(8-methyl-2-(4-methyl-5-oxo-2,5-dihydrofuran-3-yl)-1-oxo-2-azaspiro[4.5]decan-8-yl)acetamide (420 mg, 1.184 mmol) and thiourea (901 mg, 11.84 mmol) were dissolved in ethanol (20 ml) and acetic acid (4.00 ml). The mixture was heated in an oil bath for 2.5 hr at 120° C., and evaporated to dryness. The residue was diluted with methanol. Precipitate formed was filtered, and the filtrate was passed through an ion exchange column eluting with 7N NH$_3$ in MeOH to get the crude product which was purified by preparative TLC using 5%7N NH$_3$ MeOH/DCM as mobile phase. The products, (5S,8S)-8-amino-8-methyl-2-(4-methyl-5-oxo-2,5-dihydrofuran-3-yl)-2-azaspiro[4.5]decan-1-one and (5r,8r)-8-amino-8-methyl-2-(4-methyl-5-oxo-2,5-dihydrofuran-3-yl)-2-azaspiro[4.5]decan-1-one were isolated. MS [M+H]$^+$=279.2

Intermediate 41

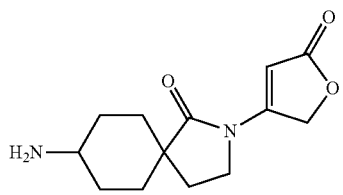 [SMILES: NC1CCC2(CC1)CCN(C1=CC(=O)OC1)C2=O]

8-amino-2-(5-oxo-2,5-dihydrofuran-3-yl)-2-azaspiro[4.5]decan-1-one

Int. 41 was prepared following procedure for Int. 36 and Int. 37 using 4-bromofuran-2(5H)-one (Boukouvalas, et al., *Tetrahedron Lett.* 2007, 48, 105-107).

Example 1

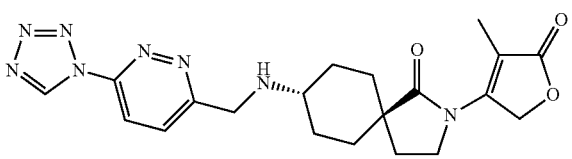 [SMILES: CC1=C(N2CC[C@]3(CC[C@@H](NCc4ccc(-n5cnnn5)nn4)CC3)C2=O)COC1=O]

(5r,8r)-2-(4-methyl-5-oxo-2,5-dihydrofuran-3-yl)-8-({[6-(1H-tetrazol-1-yl)pyridazin-3-yl]methyl}amino)-2-azaspiro[4.5]decan-1-one 6-(1H-tetrazol-1-yl)pyridazine-3-carbaldehyde (Intermediate 1, 4.0 g, 21.5 mmol) in 80 mL of MeOH and 80 mL of DCM was added (5r,8r)-8-amino-2-(4-methyl-5-oxo-2,5-dihydrofuran-3-yl)-2-azaspiro[4.5]decan-1-one (INTERMEDIATE 37A, 5.7 g, 21.5 mmol) and Ti(i-PrO)$_4$ (18 g, 64 mmol). The resulting mixture was stirred at room temperature for 2 hr, then NaBH₃CN (1.6 g, 26 mmol) was added. The resultant mixture was stirred for another 0.5 hr. Water (50 mL) was added and the mixture was filtered. The solid was washed with DCM and MeOH. The filtrate was concentrated. The residue was purified by flash chromatography (0-5% methanol in dichloromethane) to afford the title compound.

If the Ints. 37, 38A, 38B, 39A or 39B were used, the final single compounds were obtained by flash column separation and/or chiral column separation.

TABLE 4

Compounds prepared following the procedure for EXAMPLE 1

| Ex. # | Int-A | Int-B | Structure and Name | MS [M + H]⁺ |
|---|---|---|---|---|
| 2 | 30 | 37 | 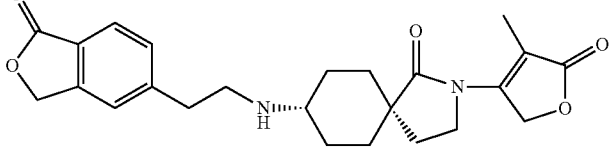<br>(5r,8r)-2-(4-methyl-5-oxo-2,5-dihydrofuran-3-yl)-<br>8-{[2-(1-oxo-1,3-dihydro-2-benzofuran-5-<br>yl)ethyl]amino}-2-azaspiro[4.5]decan-1-one | 425.2 |
| 3 | 30 | 37 | 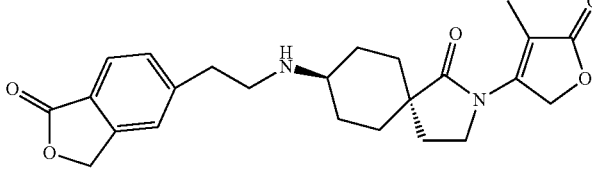<br>(5s,8s)-2-(4-methyl-5-oxo-2,5-dihydrofuran-3-yl)-<br>8-{[2-(1-oxo-1,3-dihydro-2-benzofuran-5-<br>yl)ethyl]amino}-2-azaspiro[4.5]decan-1-one | 425.2 |
| 4 | 14 | 37 | 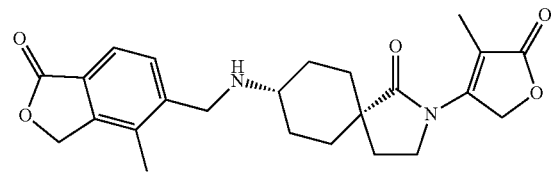 [SMILES: CC1=C(N2CC[C@]3(CC[C@H](NCc4ccc5c(c4C)COC5=O)CC3)C2=O)COC1=O]<br>(5s,8s)-8-(((4-methyl-1-oxo-1,3-dihydroisobenzofuran-<br>5-yl)methyl)amino)-2-(4-methyl-5-oxo-2,5-dihydrofuran-<br>3-yl)-2-azaspiro[4.5]decan-1-one | 425.3 |
| 5 | 2 | 37 | 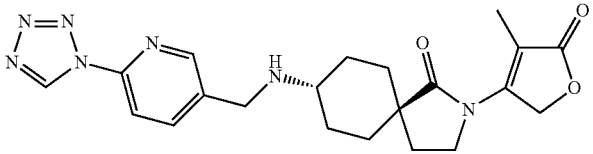 [SMILES: CC1=C(N2CC[C@]3(CC[C@@H](NCc4ccc(-n5cnnn5)nc4)CC3)C2=O)COC1=O]<br>(5r,8r)-2-(4-methyl-5-oxo-2,5-dihydrofuran-3-yl)-<br>8-({[6-(1H-tetrazol-1-yl)pyridin-3-<br>yl]methyl}amino)-2-azaspiro[4.5]decan-1-one | 424.2 |
| 6 | 2 | 37 | 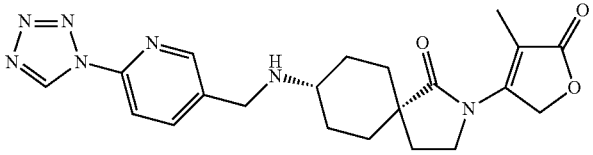 [SMILES: CC1=C(N2CC[C@]3(CC[C@H](NCc4ccc(-n5cnnn5)nc4)CC3)C2=O)COC1=O]<br>(5s,8s)-2-(4-methyl-5-oxo-2,5-dihydrofuran-3-yl)-<br>8-({[6-(1H-tetrazol-1-yl)pyridin-3-<br>yl]methyl}amino)-2-azaspiro[4.5]decan-1-one | 424.2 |

TABLE 4-continued

Compounds prepared following the procedure for EXAMPLE 1

| Ex. # | Int-A | Int-B | Structure and Name | MS [M + H]+ |
|---|---|---|---|---|
| 7A | 3 | 37 | 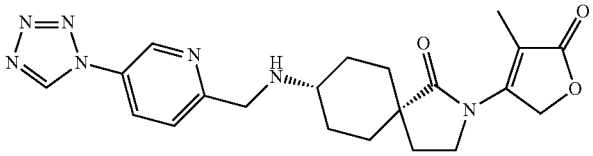 [SMILES: CC1=C(N2CC[C@]3(CC[C@H](NCc4ccc(-n5cnnn5)cn4)CC3)C2=O)COC1=O]<br>(5s,8s)-2-(4-methyl-5-oxo-2,5-dihydrofuran-3-yl)-<br>8-({[5-(1H-tetrazol-1-yl)pyridin-2-<br>yl]methyl}amino)-2-azaspiro[4.5]decan-1-one | 424.2 |
| 7B | 3 | 37 | 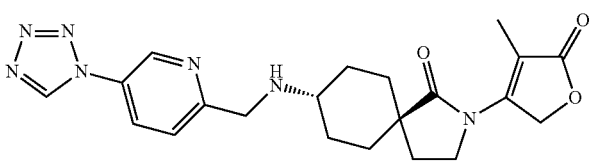 [SMILES: CC1=C(N2CC[C@]3(CC[C@@H](NCc4ccc(-n5cnnn5)cn4)CC3)C2=O)COC1=O]<br>(5r,8r)-2-(4-methyl-5-oxo-2,5-dihydrofuran-3-yl)-<br>8-({[5-(1H-tetrazol-1-yl)pyridin-2-<br>yl]methyl}amino)-2-azaspiro[4.5]decan-1-one | 424.2 |
| 9 | 25 | 37 | 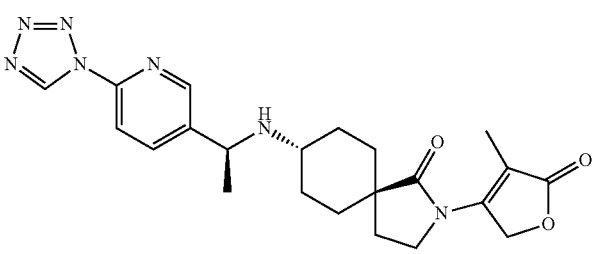 [SMILES: CC1=C(N2CC[C@]3(CC[C@@H](N[C@@H](C)c4ccc(-n5cnnn5)nc4)CC3)C2=O)COC1=O]<br>(5S,8r)-2-(4-methyl-5-oxo-2,5-dihydrofuran-3-<br>yl)-8-({(1S)-1-[6-(1H-tetrazol-1-yl)pyridin-3-<br>yl]ethyl}amino)-2-azaspiro[4.5]decan-1-one | 438.2 |
| 10 | 25 | 37 | 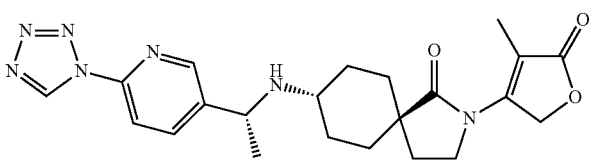 [SMILES: CC1=C(N2CC[C@]3(CC[C@@H](N[C@H](C)c4ccc(-n5cnnn5)nc4)CC3)C2=O)COC1=O]<br>(5R,8r)-8-(((R)-1-(6-(1H-tetrazol-1-yl)pyridin-3-<br>yl)ethyl)amino)-2-(4-methyl-5-oxo-2,5-<br>dihydrofuran-3-yl)-2-azaspiro[4.5]decan-1-oneSeparated | 438.2 |
| 11 | 10 | 37 | 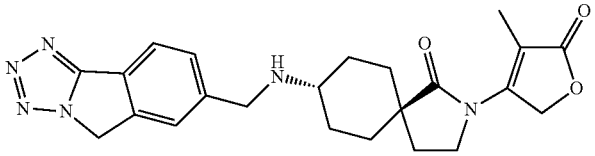 [SMILES: CC1=C(N2CC[C@]3(CC[C@@H](NCc4ccc5c(c4)Cn4nnnc4-5)CC3)C2=O)COC1=O]<br>(5r,8r)-2-(4-methyl-5-oxo-2,5-dihydrofuran-3-yl)-<br>8-[(5H-tetrazolo[5,1-a]isoindol-7-<br>ylmethyl)amino]-2-azaspiro[4.5]decan-1-one | 435.2 |

TABLE 4-continued

Compounds prepared following the procedure for EXAMPLE 1

| Ex. # | Int-A | Int-B | Structure and Name | MS [M + H]+ |
|---|---|---|---|---|
| 12 | 5 | 37 | 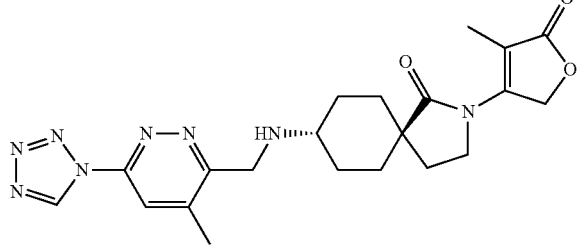<br>(5r,8r)-2-(4-methyl-5-oxo-2,5-dihydrofuran-3-yl)-<br>8-({[4-methyl-6-(1H-tetrazol-1-yl)pyridazin-3-<br>yl]methyl}amino)-2-azaspiro[4.5]decan-1-one | 411.2 |
| 13 | 4 | 37 | 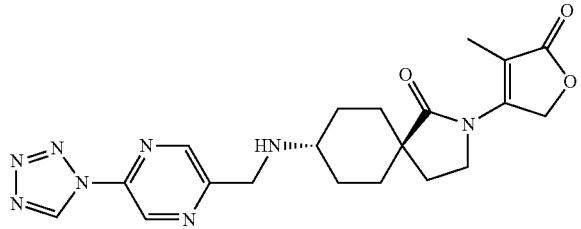 [SMILES: CC1=C(N2CC[C@]3(CC[C@@H](NCc4cnc(-n5cnnn5)cn4)CC3)C2=O)COC1=O]<br>(5s,8s)-2-(4-methyl-5-oxo-2,5-dihydrofuran-3-yl)-<br>8-({[5-(1H-tetrazol-1-yl)pyrazin-2-<br>yl]methyl}amino)-2-azaspiro[4.5]decan-1-one | 397.3 |
| 14 | 6 | 37 | 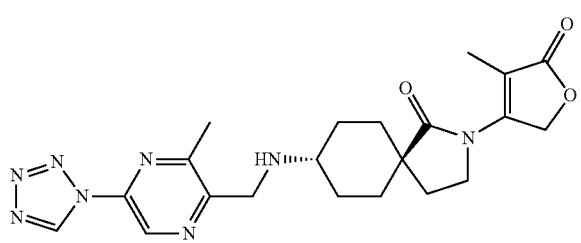<br>(5r,8r)-2-(4-methyl-5-oxo-2,5-dihydrofuran-3-yl)-<br>8-({[3-methyl-5-(1H-tetrazol-1-yl)pyrazin-2-<br>yl]methyl}amino)-2-azaspiro[4.5]decan-1-one | 411.2<br>([M + 1-28]+) |
| 15 | 21 | 37 | 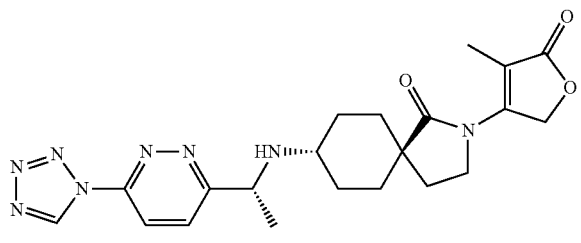<br>(5R,8r)-2-(4-methyl-5-oxo-2,5-dihydrofuran-3-yl)-<br>8-({(1R)-1-[6-(1H-tetrazol-1-yl)pyridazin-3-<br>yl]ethyl}amino)-2-azaspiro[4.5]decan-1-one | 411.2<br>([M + 1-28]+) |

TABLE 4-continued

Compounds prepared following the procedure for EXAMPLE 1

| Ex. # | Int-A | Int-B | Structure and Name | MS [M + H]+ |
|---|---|---|---|---|
| 16 | 21 | 37 | 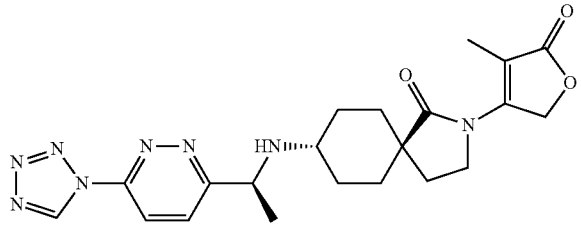<br>(5r,8r)-2-(4-methyl-5-oxo-2,5-dihydrofuran-3-yl)-<br>8-({1-[6-(1H-tetrazol-1-yl)pyridazin-3-<br>yl]ethyl}amino)-2-azaspiro[4.5]decan-1-one | 411.2<br>([M + 1-28]+) |
| 17 | 28 | 37 | 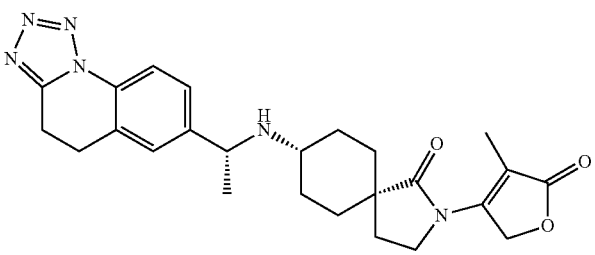 [SMILES: CC1=C(N2CC[C@]3(CC[C@H](N[C@H](C)c4ccc5c(c4)CCc4nnnn4-5)CC3)C2=O)COC1=O]<br>(5S,8s)-8-{[(1R)-1-(4,5-dihydrotetrazolo[1,5-<br>a]quinolin-7-yl)ethyl]amino}-2-(4-methyl-5-oxo-<br>2,5-dihydrofuran-3-yl)-2-azaspiro[4.5]decan-1-one | 463.2 |
| 18 | 28 | 37 | 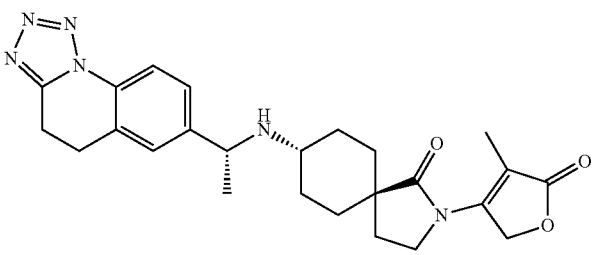 [SMILES: CC1=C(N2CC[C@]3(CC[C@@H](N[C@H](C)c4ccc5c(c4)CCc4nnnn4-5)CC3)C2=O)COC1=O]<br>(5R,8r)-8-{[(1R)-1-(4,5-dihydrotetrazolo[1,5-<br>a]quinolin-7-yl)ethyl]amino}-2-(4-methyl-5-oxo-<br>2,5-dihydrofuran-3-yl)-2-azaspiro[4.5]decan-1-one | 463.2 |
| 19 | 1 | 39B | 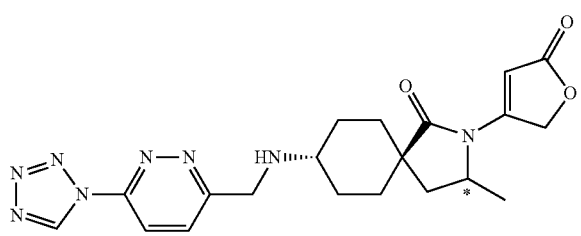<br>(5r,8r)-3-methyl-2-(5-oxo-2,5-dihydrofuran-3-yl)-<br>8-({[6-(1H-tetrazol-1-yl)pyridazin-3-<br>yl]methyl}amino)-2-azaspiro[4.5]decan-1-one | 397.2 |
| 20 | 22 | 37 | 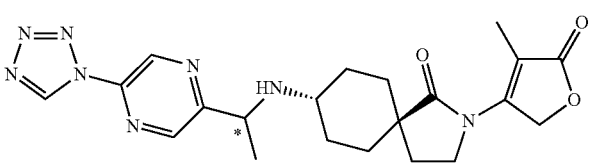<br>(5R,8r)-2-(4-methyl-5-oxo-2,5-dihydrofuran-3-yl)-<br>8-({(1R)-1-[5-(1H-tetrazol-1-yl)pyrazin-2-<br>yl]ethyl}amino)-2-azaspiro[4.5]decan-1-one | 411.2<br>([M + 1-28]+) |

TABLE 4-continued

Compounds prepared following the procedure for EXAMPLE 1

| Ex. # | Int-A | Int-B | Structure and Name | MS [M + H]+ |
|---|---|---|---|---|
| 21 | 28 | 37 | 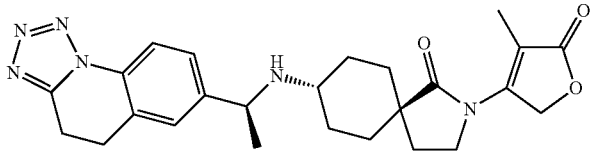 [SMILES: CC1=C(N2CC[C@]3(CC[C@@H](N[C@@H](C)c4ccc5c(c4)CCc4nnnn4-5)CC3)C2=O)COC1=O]<br>(5S,8r)-8-{[(1S)-1-(4,5-dihydrotetrazolo[1,5-a]quinolin-7-yl)ethyl]amino}-2-(4-methyl-5-oxo-2,5-dihydrofuran-3-yl)-2-azaspiro[4.5]decan-1-one | 463.2 |
| 22 | 2 | 39B | 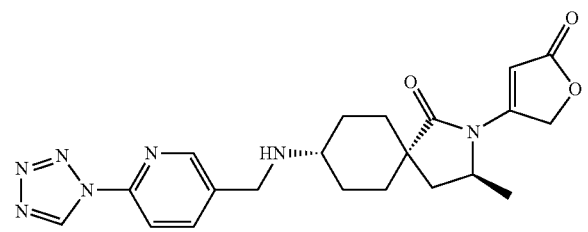 [SMILES: C[C@H]1C[C@]2(CC[C@H](NCc3ccc(-n4cnnn4)nc3)CC2)C(=O)N1C1=CC(=O)OC1]<br>(3S,5s,8R)-3-methyl-2-(5-oxo-2,5-dihydrofuran-3-yl)-8-({[6-(1H-tetrazol-1-yl)pyridin-3-yl]methyl}amino)-2-azaspiro[4.5]decan-1-one | 424.2 |
| 23 | 2 | 39A | 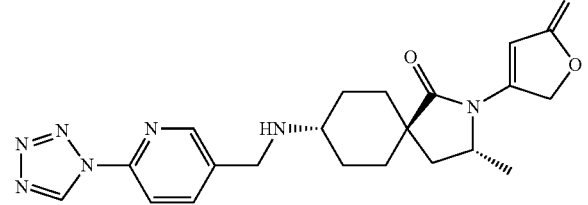<br>(3R,5r,8R)-3-methyl-2-(5-oxo-2,5-dihydrofuran-3-yl)-8-({[6-(1H-tetrazol-1-yl)pyridin-3-yl]methyl}amino)-2-azaspiro[4.5]decan-1-one | 424.2 |
| 24 | 22 | 37 | 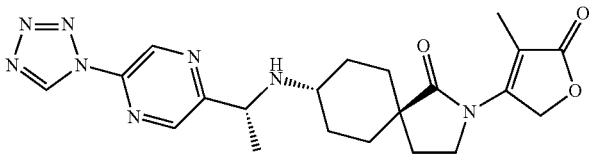<br>(5R,8r)-2-(4-methyl-5-oxo-2,5-dihydrofuran-3-yl)-8-({(1R)-1-[5-(1H-tetrazol-1-yl)pyrazin-2-yl]ethyl}amino)-2-azaspiro[4.5]decan-1-one | 411.2 ([M + 1-28]+) |
| 25 | 22 | 37 | 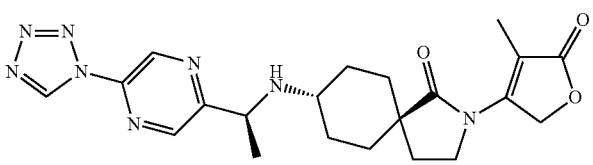 [SMILES: CC1=C(N2CC[C@]3(CC[C@@H](N[C@@H](C)c4cnc(-n5cnnn5)cn4)CC3)C2=O)COC1=O]<br>(5R,8r)-2-(4-methyl-5-oxo-2,5-dihydrofuran-3-yl)-8-({(1R)-1-[5-(1H-tetrazol-1-yl)pyrazin-2-yl]ethyl}amino)-2-azaspiro[4.5]decan-1-one | 411.2 |

TABLE 4-continued

Compounds prepared following the procedure for EXAMPLE 1

| Ex. # | Int-A | Int-B | Structure and Name | MS [M + H]+ |
|---|---|---|---|---|
| 26 | 4 | 39A | (3R,5s,8S)-3-methyl-2-(5-oxo-2,5-dihydrofuran-3-yl)-8-({[5-(1H-tetrazol-1-yl)pyrazin-2-yl]methyl}amino)-2-azaspiro[4.5]decan-1-one | 425.2 |
| 27 | 2 | 39A | (3R,5s,8S)-3-methyl-2-(5-oxo-2,5-dihydrofuran-3-yl)-8-({[6-(1H-tetrazol-1-yl)pyridin-3-yl]methyl}amino)-2-azaspiro[4.5]decan-1-one | 424.1 |
| 28 | 4 | 39B | (3S,5s,8R)-3-methyl-2-(5-oxo-2,5-dihydrofuran-3-yl)-8-({[5-(1H-tetrazol-1-yl)pyrazin-2-yl]methyl}amino)-2-azaspiro[4.5]decan-1-one | 425.2 |
| 29 | 23 | 37 | (5S,8r)-2-(4-methyl-5-oxo-2,5-dihydrofuran-3-yl)-8-({(1S)-1-[5-(1H-tetrazol-1-yl)pyridin-2-yl]ethyl}amino)-2-azaspiro[4.5]decan-1-one. | 438.2 |
| 30 | 24 | 37 | (5R,8r)-2-(4-methyl-5-oxo-2,5-dihydrofuran-3-yl)-8-{[(1R)-1-(5H-tetrazolo[5,1-a]isoindol-7-yl)ethyl]amino}-2-azaspiro[4.5]decan-1-one | 449.2 |

TABLE 4-continued

Compounds prepared following the procedure for EXAMPLE 1

| Ex. # | Int-A | Int-B | Structure and Name | MS [M + H]+ |
|---|---|---|---|---|
| 31 | 24 | 37 | 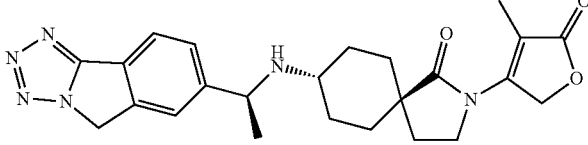(5S,8r)-2-(4-methyl-5-oxo-2,5-dihydrofuran-3-yl)-8-{[(1S)-1-(5H-tetrazolo[5,1-a]isoindol-7-yl)ethyl]amino}-2-azaspiro[4.5]decan-1-one | 449.2 |
| 32 | 23 | 37 | 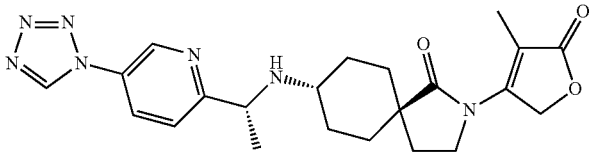 [SMILES: CC1=C(N2CC[C@]3(CC[C@@H](N[C@H](C)c4ccc(-n5cnnn5)cn4)CC3)C2=O)COC1=O]5R,8r)-2-(4-methyl-5-oxo-2,5-dihydrofuran-3-yl)-8-({(1R)-1-[5-(1H-tetrazol-1-yl)pyridin-2-yl]ethyl}amino)-2-azaspiro[4.5]decan-1-one | 438.2 |
| 33 | 4 | 39 | 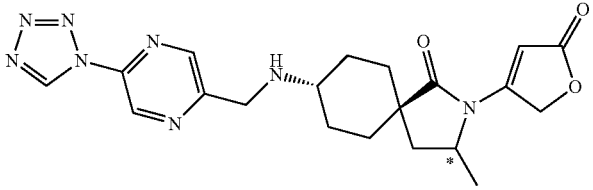(5r,8r)-3-methyl-2-(5-oxo-2,5-dihydrofuran-3-yl)-8-({[5-(1H-tetrazol-1-yl)pyrazin-2-yl]methyl}amino)-2-azaspiro[4.5]decan-1-one | 397.1 ([M + 1-28]+) |
| 34 | 7 | 37 | 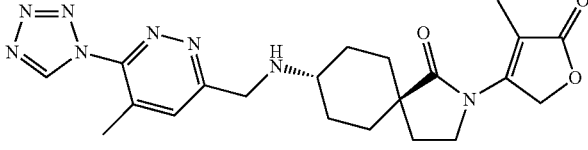(5r,8r)-2-(4-methyl-5-oxo-2,5-dihydrofuran-3-yl)-8-({[5-methyl-6-(1H-tetrazol-1-yl)pyridazin-3-yl]methyl}amino)-2-azaspiro[4.5]decan-1-one | 411.2 ([M + 1-28]+) |
| 35 | 1 | 39B | 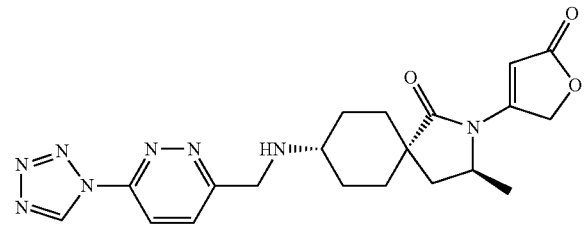(3S,5s,8R)-8-(((6-(1H-tetrazol-1-yl)pyridazin-3-yl)methyl)amino)-3-methyl-2-(5-oxo-2,5-dihydrofuran-3-yl)-2-azaspiro[4.5]decan-1-one | 397.2 ([M + 1-28]+) |

TABLE 4-continued

Compounds prepared following the procedure for EXAMPLE 1

| Ex. # | Int-A | Int-B | Structure and Name | MS [M + H]+ |
|---|---|---|---|---|
| 36 | 1 | 39A | 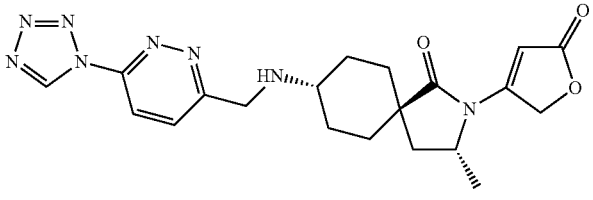<br>(3R,5r,8R)-3-methyl-2-(5-oxo-2,5-dihydrofuran-3-yl)-8-({[6-(1H-tetrazol-1-yl)pyridazin-3-yl]methyl}amino)-2-azaspiro[4.5]decan-1-one | 397.2 ([M + 1-28]+) |
| 37 | 1 | 39B | 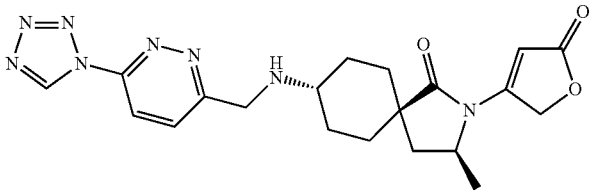<br>(3S,5r,8S)-8-(((6-(1H-tetrazol-1-yl)pyridazin-3-yl)methyl)amino)-3-methyl-2-(5-oxo-2,5-dihydrofuran-3-yl)-2-azaspiro[4.5]decan-1-one | 397.2 ([M + 1-28]+) |
| 38 | 1 | 38B | 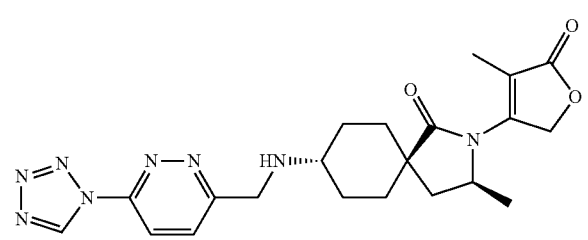<br>(3S,5r,8S)-8-(((6-(1H-tetrazol-1-yl)pyridazin-3-yl)methyl)amino)-3-methyl-2-(4-methyl-5-oxo-2,5-dihydrofuran-3-yl)-2-azaspiro[4.5]decan-1-one | 411.2 ([M + 1-28]+) |
| 39 | 1 | 38A | 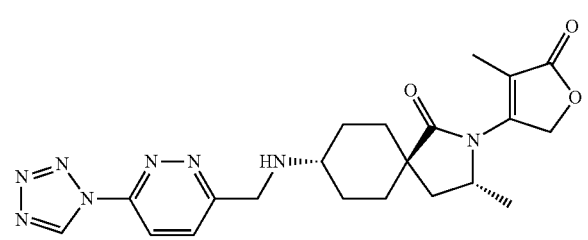<br>(3R,5r,8R)-8-(((6-(1H-tetrazol-1-yl)pyridazin-3-yl)methyl)amino)-3-methyl-2-(4-methyl-5-oxo-2,5-dihydrofuran-3-yl)-2-azaspiro[4.5]decan-1-one | 411.2 ([M + 1-28]+) |
| 40 | 33 | 37 | 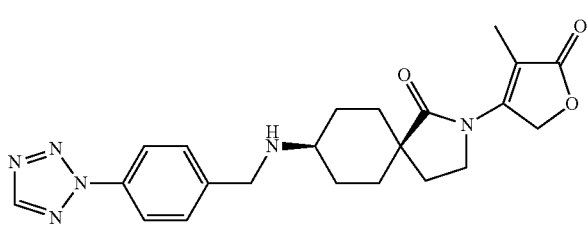 [SMILES: CC1=C(N2CC[C@]3(CC[C@H](NCc4ccc(-n5ncnn5)cc4)CC3)C2=O)COC1=O]<br>(5s,8s)-2-(4-methyl-5-oxo-2,5-dihydrofuran-3-yl)-8-{[4-(2H-tetrazol-2-yl)benzyl]amino}-2-azaspiro[4.5]decan-1-one | 423.6 |

TABLE 4-continued

Compounds prepared following the procedure for EXAMPLE 1

| Ex. # | Int-A | Int-B | Structure and Name | MS [M + H]+ |
|---|---|---|---|---|
| 41 | 33 | 37 | 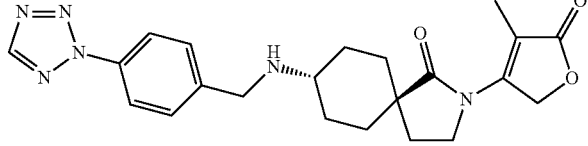<br>(5r,8r)-2-(4-methyl-5-oxo-2,5-dihydrofuran-3-yl)-8-{[4-(2H-tetrazol-2-yl)benzyl]amino}-2-azaspiro[4.5]decan-1-one | 423.6 |
| 42 | 1 | 40B | 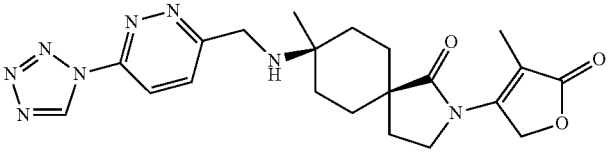 [SMILES: CC1=C(N2CC[C@]3(CC[C@](C)(NCc4ccc(-n5cnnn5)nn4)CC3)C2=O)COC1=O]<br>(5s,8s)-8-methyl-2-(4-methyl-5-oxo-2,5-dihydrofuran-3-yl)-8-({[6-(1H-tetrazol-1-yl)pyridazin-3-yl]methyl}amino)-2-azaspiro[4.5]decan-1-one | 439.7 |
| 43 | 8 | 37 | 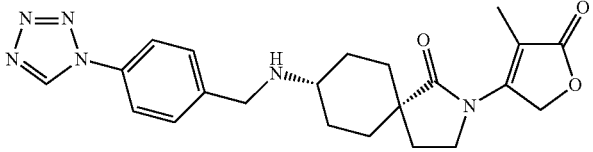 [SMILES: CC1=C(N2CC[C@]3(CC[C@H](NCc4ccc(-n5cnnn5)cc4)CC3)C2=O)COC1=O]<br>(5s,8s)-2-(4-methyl-5-oxo-2,5-dihydrofuran-3-yl)-8-{[4-(1H-tetrazol-1-yl)benzyl]amino}-2-azaspiro[4.5]decan-1-one | 423.2 |
| 44 | 8 | 37 | 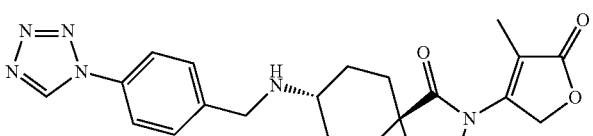<br>(5r,8r)-2-(4-methyl-5-oxo-2,5-dihydrofuran-3-yl)-8-{[4-(1H-tetrazol-1-yl)benzyl]amino}-2-azaspiro[4.5]decan-1-one | 423.2 |
| 45 | 11 | 37 | 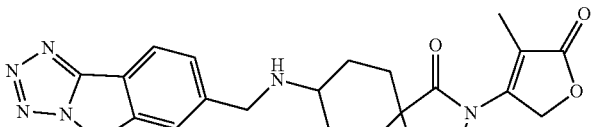<br>2-(4-methyl-5-oxo-2,5-dihydrofuran-3-yl)-8-{[(6-methyl-5H-tetrazolo[5,1-a]isoindol-7-yl)methyl]amino}-2-azaspiro[4.5]decan-1-one (a mixture of two isomers) | 471.1 |
| 46 | 26 | 37 | 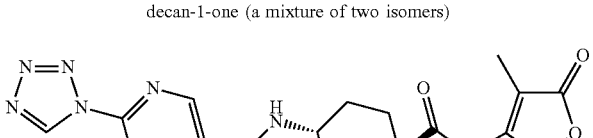<br>(5R,8r)-2-(4-methyl-5-oxo-2,5-dihydrofuran-3-yl)-8-(((R)-1-(4-methyl-6-(1H-tetrazol-1-yl)pyridazin-3-yl)ethyl)amino)-2-azaspiro[4.5]decan-1-one. | 425.2 |

TABLE 4-continued

Compounds prepared following the procedure for EXAMPLE 1

| Ex. # | Int-A | Int-B | Structure and Name | MS [M + H]+ |
|---|---|---|---|---|
| 47 | 15 | 37 | 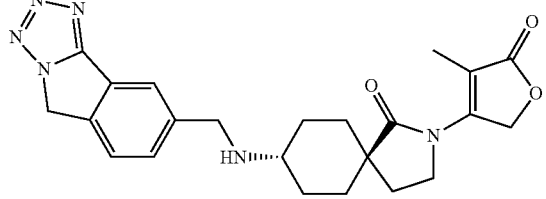<br>(5r,8r)-2-(4-methyl-5-oxo-2,5-dihydrofuran-3-yl)-8-[(5H-tetrazolo[5,1-a]isoindol-8-ylmethyl)amino]-2-azaspiro[4.5]decan-1-one | 435.2 |
| 48 | 1 | 39 | 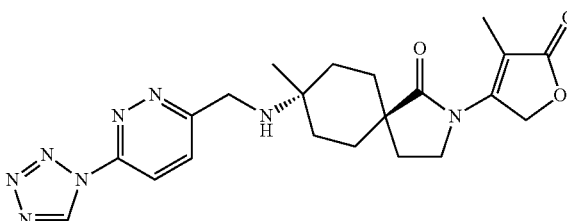<br>(5r,8r)-8-methyl-2-(4-methyl-5-oxo-2,5-dihydrofuran-3-yl)-8-({[6-(1H-tetrazol-1-yl)pyridazin-3-yl]methyl}amino)-2-azaspiro[4.5]decan-1-one | 439.5 |
| 49 | 4 | 39 | 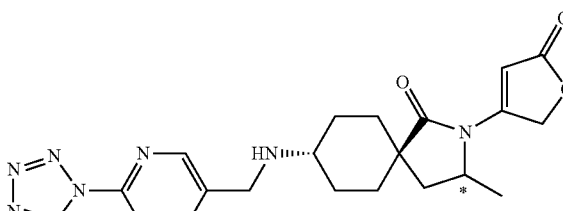<br>(5r,8r)-3-methyl-2-(5-oxo-2,5-dihydrofuran-3-yl)-8-({[5-(1H-tetrazol-1-yl)pyrazin-2-yl]methyl}amino)-2-azaspiro[4.5]decan-1-one | 425.7 |
| 50 | 4 | 40 | 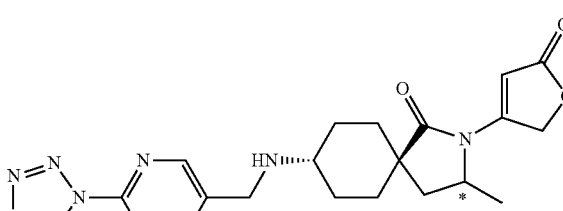<br>(5r,8r)-3-methyl-2-(5-oxo-2,5-dihydrofuran-3-yl)-8-({[5-(1H-tetrazol-1-yl)pyrazin-2-yl]methyl}amino)-2-azaspiro[4.5]decan-1-one | 425.7 |
| 51 | 16 | 37 | 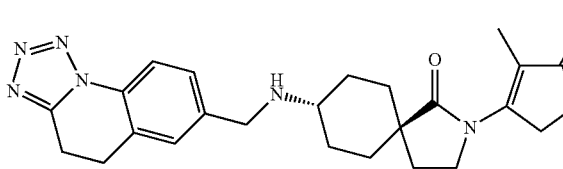<br>(5r,8r)-8-(((4,5-dihydrotetrazolo[1,5-a]quinolin-7-yl)methyl)amino)-2-(4-methyl-5-oxo-2,5-dihydrofuran-3-yl)-2-azaspiro[4.5]decan-1-one | 449.2 |

TABLE 4-continued

Compounds prepared following the procedure for EXAMPLE 1

| Ex. # | Int-A | Int-B | Structure and Name | MS [M + H]+ |
|---|---|---|---|---|
| 52 | 19 | 37 | 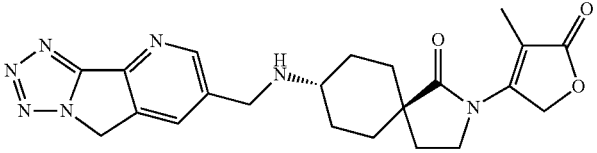 [SMILES: CC1=C(N2CC[C@]3(CC[C@@H](NCc4cnc5c(c4)Cn4nnnc4-5)CC3)C2=O)COC1=O]<br>(5r,8r)-8-(((8H-tetrazolo[1',5':1,2]pyrrolo[3,4-b]pyridin-6-yl)methyl)amino)-2-(4-methyl-5-oxo-2,5-dihydrofuran-3-yl)-2-azaspiro[4.5]decan-1-one | 436.1 |
| 53 | 18 | 37 | 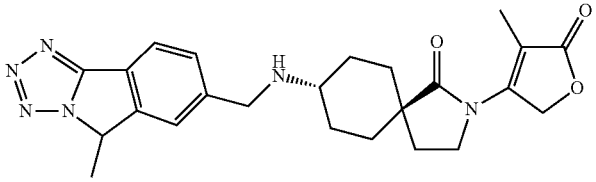 [SMILES: CC1=C(N2CC[C@]3(CC[C@@H](NCc4ccc5c(c4)C(C)n4nnnc4-5)CC3)C2=O)COC1=O]<br>(5r,8r)-2-(4-methyl-5-oxo-2,5-dihydrofuran-3-yl)-8-(((5-methyl-5H-tetrazolo[5,1-a]isoindol-7-yl)methyl)amino)-2-azaspiro[4.5]decan-1-one | 449.2 |
| 54 | 11 | 37 | 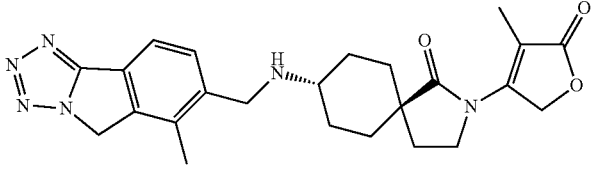 [SMILES: CC1=C(N2CC[C@]3(CC[C@@H](NCc4ccc5c(c4C)Cn4nnnc4-5)CC3)C2=O)COC1=O]<br>(5r,8r)-2-(4-methyl-5-oxo-2,5-dihydrofuran-3-yl)-8-(((6-methyl-5H-tetrazolo[5,1-a]isoindol-7-yl)methyl)amino)-2-azaspiro[4.5]decan-1-one | 449.2 |
| 55 | 10 | 38A | 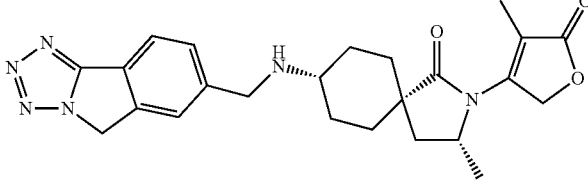<br>(3R,5s,8S)-8-(((5H-tetrazolo[5,1-a]isoindol-7-yl)methyl)amino)-3-methyl-2-(4-methyl-5-oxo-2,5-dihydrofuran-3-yl)-2-azaspiro[4.5]decan-1-one | 449.2 |
| 56 | 10 | 38B | 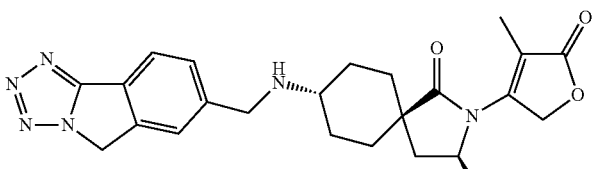<br>(3S,5r,8S)-8-(((5H-tetrazolo[5,1-a]isoindol-7-yl)methyl)amino)-3-methyl-2-(4-methyl-5-oxo-2,5-dihydrofuran-3-yl)-2-azaspiro[4.5]decan-1-one | 449.2 |

TABLE 4-continued

Compounds prepared following the procedure for EXAMPLE 1

| Ex. # | Int-A | Int-B | Structure and Name | MS [M + H]+ |
|---|---|---|---|---|
| 57 | 4 | 38B | 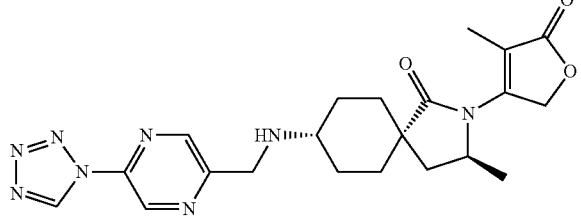<br>(3S,5s,8R)-8-(((5-(1H-tetrazol-1-yl)pyrazin-2-yl)methyl)amino)-3-methyl-2-(4-methyl-5-oxo-2,5-dihydrofuran-3-yl)-2-azaspiro[4.5]decan-1-one | 411.2 ([M + 1-28]+) |
| 58 | 10 | 38B | 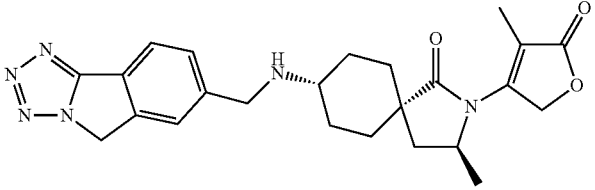 [SMILES: CC1=C(N2C(=O)[C@]3(CC[C@@H](NCc4ccc5c(c4)Cn4nnnc4-5)CC3)C[C@@H]2C)COC1=O]<br>(3S,5s,8R)-8-(((5H-tetrazolo[5,1-a]isoindol-7-yl)methyl)amino)-3-methyl-2-(4-methyl-5-oxo-2,5-dihydrofuran-3-yl)-2-azaspiro[4.5]decan-1-one. | 449.2 |
| 59 | 12 | 37 | 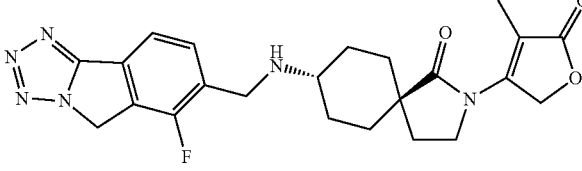<br>(5r,8r)-8-(((6-fluoro-5H-tetrazolo[5,1-a]isoindol-7-yl)methyl)amino)-2-(4-methyl-5-oxo-2,5-dihydrofuran-3-yl)-2-azaspiro[4.5]decan-1-one | 453.2 |
| 60 | 10 | 38A | 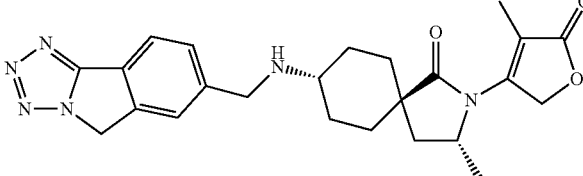<br>(3R,5r,8R)-8-(((5H-tetrazolo[5,1-a]isoindol-7-yl)methyl)amino)-3-methyl-2-(4-methyl-5-oxo-2,5-dihydrofuran-3-yl)-2-azaspiro[4.5]decan-1-one | 449.2 |
| 61 | 13 | 37 | 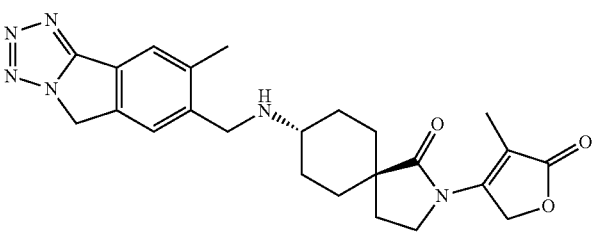 [SMILES: CC1=C(N2CC[C@]3(CC[C@@H](NCc4cc5c(cc4C)-c4nnnn4C5)CC3)C2=O)COC1=O]<br>(5r,8r)-2-(4-methyl-5-oxo-2,5-dihydrofuran-3-yl)-8-(((8-methyl-5H-tetrazolo[5,1-a]isoindol-7-yl)methyl)amino)-2-azaspiro[4.5]decan-1-one | 449.2 |

TABLE 4-continued

Compounds prepared following the procedure for EXAMPLE 1

| Ex. # | Int-A | Int-B | Structure and Name | MS [M + H]+ |
|---|---|---|---|---|
| 62 | 10 | 39B | 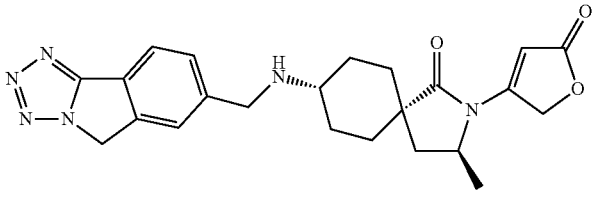 [SMILES: C[C@H]1C[C@]2(CC[C@H](NCc3ccc4c(c3)Cn3nnnc3-4)CC2)C(=O)N1C1=CC(=O)OC1]<br>(3S,5s,8R)-8-(((5H-tetrazolo[5,1-a]isoindol-7-yl)methyl)amino)-3-methyl-2-(5-oxo-2,5-dihydrofuran-3-yl)-2-azaspiro[4.5]decan-1-one | 435.2 |
| 63 | 10 | 39B | 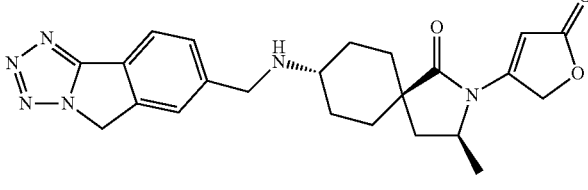<br>(3S,5r,8S)-8-(((5H-tetrazolo[5,1-a]isoindol-7-yl)methyl)amino)-3-methyl-2-(5-oxo-2,5-dihydrofuran-3-yl)-2-azaspiro[4.5]decan-1-one | 435.2 |
| 64 | 4 | 38A | 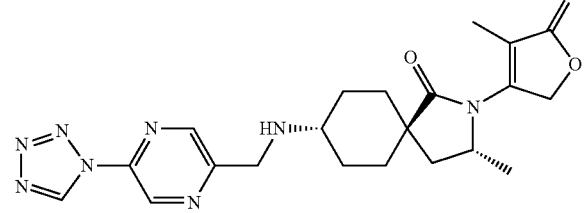<br>(3R,5r,8R)-8-(((5-(1H-tetrazol-1-yl)pyrazin-2-yl)methyl)amino)-3-methyl-2-(4-methyl-5-oxo-2,5-dihydrofuran-3-yl)-2-azaspiro[4.5]decan-1-one | 411.2 ([M + 1-28]+) |
| 65 | 10 | 39A | 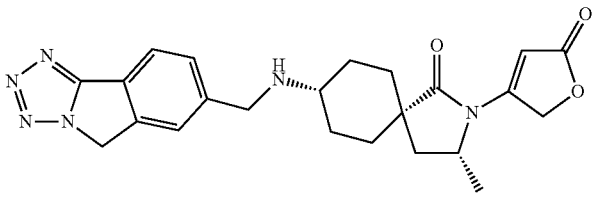 [SMILES: C[C@@H]1C[C@]2(CC[C@H](NCc3ccc4c(c3)Cn3nnnc3-4)CC2)C(=O)N1C1=CC(=O)OC1]<br>(3R,5s,8S)-8-(((5H-tetrazolo[5,1-a]isoindol-7-yl)methyl)amino)-3-methyl-2-(5-oxo-2,5-dihydrofuran-3-yl)-2-azaspiro[4.5]decan-1-one | 435.2 |
| 66 | 4 | 39B | 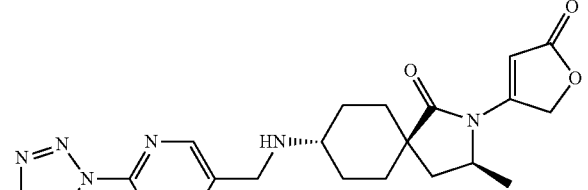<br>(3S,5r,8S)-8-(((5-(1H-tetrazol-1-yl)pyrazin-2-yl)methyl)amino)-3-methyl-2-(5-oxo-2,5-dihydrofuran-3-yl)-2-azaspiro[4.5]decan-1-one | 425.1 |

TABLE 4-continued

Compounds prepared following the procedure for EXAMPLE 1

| Ex. # | Int-A | Int-B | Structure and Name | MS [M + H]+ |
|---|---|---|---|---|
| 67 | 9 | 37 | 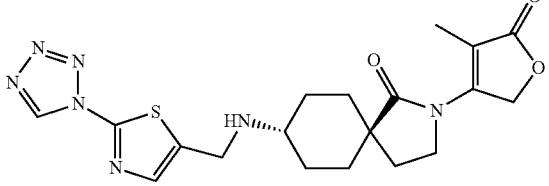<br>(5r,8r)-8-(((2-(1H-tetrazol-1-yl)thiazol-5-yl)methyl)amino)-2-(4-methyl-5-oxo-2,5-dihydrofuran-3-yl)-2-azaspiro[4.5]decan-1-one | 452.0 |
| 68 | 4 | 40B | 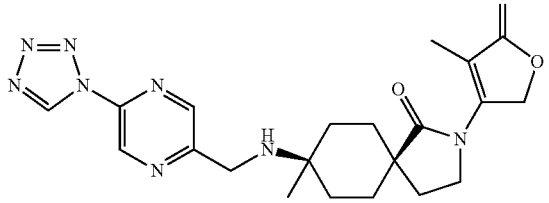<br>(5s,8s)-8-(((5-(1H-tetrazol-1-yl)pyrazin-2-yl)methyl)amino)-8-methyl-2-(4-methyl-5-oxo-2,5-dihydrofuran-3-yl)-2-azaspiro[4.5]decan-1-one | 439.4 |
| 69 | 4 | 40A | 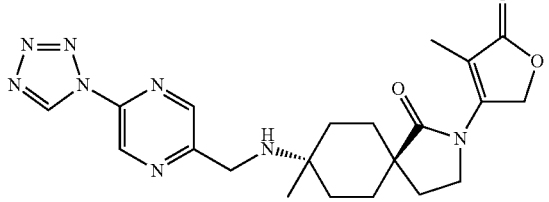<br>(5r,8r)-8-(((5-(1H-tetrazol-1-yl)pyrazin-2-yl)methyl)amino)-8-methyl-2-(4-methyl-5-oxo-2,5-dihydrofuran-3-yl)-2-azaspiro[4.5]decan-1-one | 439.4 |
| 70 | 9 | 39B | 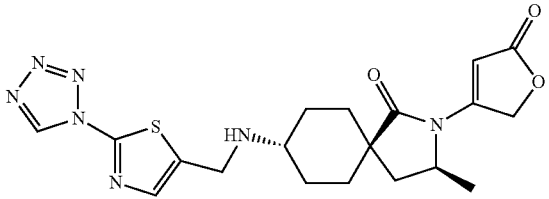 [SMILES: C[C@H]1C[C@]2(CC[C@@H](NCc3cnc(-n4cnnn4)s3)CC2)C(=O)N1C1=CC(=O)OC1]<br>(3S,5r,8S)-8-(((2-(1H-tetrazol-1-yl)thiazol-5-yl)methyl)amino)-3-methyl-2-(5-oxo-2,5-dihydrofuran-3-yl)-2-azaspiro[4.5]decan-1-one | 402.0 |
| 71 | 9 | 39A | 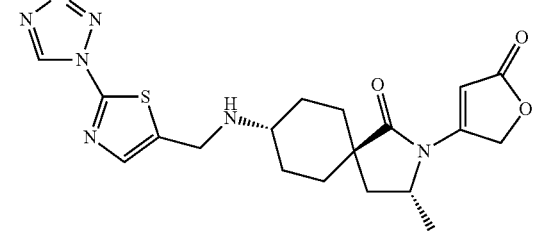<br>(3R,5r,8R)-8-(((2-(1H-tetrazol-1-yl)thiazol-5-yl)methyl)amino)-3-methyl-2-(5-oxo-2,5-dihydrofuran-3-yl)-2-azaspiro[4.5]decan-1-one | 402.0 |

TABLE 4-continued

Compounds prepared following the procedure for EXAMPLE 1

| Ex. # | Int-A | Int-B | Structure and Name | MS [M + H]+ |
|---|---|---|---|---|
| 72 | 4 | 41 | 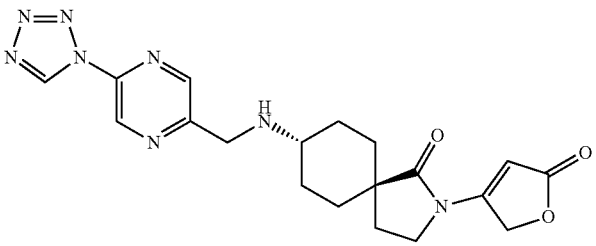 [SMILES: O=C1C=C(N2CC[C@]3(CC[C@@H](NCc4cnc(-n5cnnn5)cn4)CC3)C2=O)CO1]<br>(5r,8r)-8-(((5-(1H-tetrazol-1-yl)pyrazin-2-yl)methyl)amino)-2-(5-oxo-2,5-dihydrofuran-3-yl)-2-azaspiro[4.5]decan-1-one | 411.3 |
| 73 | 4 | 41 | 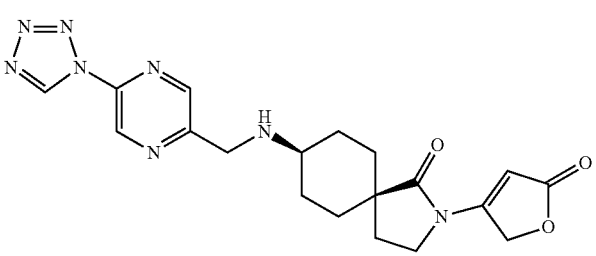 [SMILES: O=C1C=C(N2CC[C@]3(CC[C@H](NCc4cnc(-n5cnnn5)cn4)CC3)C2=O)CO1]<br>(5s,8s)-8-(((5-(1H-tetrazol-1-yl)pyrazin-2-yl)methyl)amino)-2-(5-oxo-2,5-dihydrofuran-3-yl)-2-azaspiro[4.5]decan-1-one | 411.3 |

Example 74

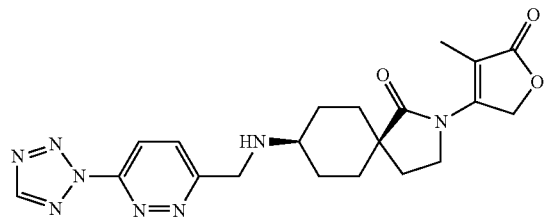 [SMILES: CC1=C(N2CC[C@]3(CC[C@H](NCc4ccc(-n5ncnn5)nn4)CC3)C2=O)COC1=O]

(5s,8s)-8-(((6-(2H-tetrazol-2-yl)pyridazin-3-yl)methyl)amino)-2-(4-methyl-5-oxo-2,5-dihydrofuran-3-yl)-2-azaspiro[4.5]decan-1-one

Example 75

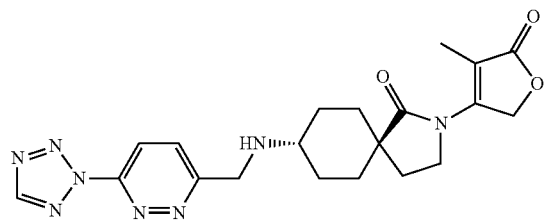 [SMILES: CC1=C(N2CC[C@]3(CC[C@@H](NCc4ccc(-n5ncnn5)nn4)CC3)C2=O)COC1=O]

(5r,8r)-8-(((6-(2H-tetrazol-2-yl)pyridazin-3-yl)methyl)amino)-2-(4-methyl-5-oxo-2,5-dihydrofuran-3-yl)-2-azaspiro[4.5]decan-1-one To the mixture of (6-(2H-tetrazol-2-yl)pyridazin-3-yl)methanamine (Intermediate 34, 100 mg, 0.564 mmol) and 2-(4-methyl-5-oxo-2,5-dihydrofuran-3-yl)-2-azaspiro[4.5]decane-1,8-dione (Intermediate 36, 149 mg, 0.564 mmol) in THF (12 ml) was added tetraethoxytitanium (155 mg, 0.677 mmol). The resulting mixture was stirred at rt overnight before addition of sodium cyanoborohydride (106 mg, 1.693 mmol). The resulting mixture was stirred at rt for 2 h before quenching by addition of water. After concentration, the residue was dissolved in 10% MeOH/DCM, and filtered. The filtrate was concentrated and the residue was purified by TLC (6×1000 MU) using 10% MeOH/DCM to give (5s,8s)-8-4(6-(2H-tetrazol-2-yl)pyridazin-3-yl)methyl)amino)-2-(4-methyl-5-oxo-2,5-dihydrofuran-3-yl)-2-azaspiro[4.5]decan-1-one (Less polar on TLC), MS: (M+23)+: 447.15. $^1$H-NMR (400 MHz, CDCl$_3$) δ 9.787 (s, 1H), 8.323-8.305 (d, J=9.0 Hz, 1H), 8.091-8.073 (d, J=9.0 Hz, 1H), 5.331 (s, 2H), 4.292 (s, 2H), 4.032-4.004 (t, J=7.0 Hz, 2H), 2.808-2.778 (m, 1H), 2.064 (s, 3H), 2.102-2.028 (m, 4H), 1.863-1.740 (m, 4H), 1.442-1.389 (m, 2H), and (5r,8r)-8-4(6-(2H-tetrazol-2-yl)pyridazin-3-yl)methyl)amino)-2-(4-methyl-5-oxo-2,5-dihydrofuran-3-yl)-2-azaspiro[4.5]decan-1-one (more polar on TLC), MS: (M+23)+: 447.22. $^1$H-NMR (400 MHz, CDCl$_3$) δ 9.784 (s, 1H), 8.318-8.301 (d, J=8.9 Hz, 1H), 7.981-7.962 (d, J=9.0 Hz, 1H), 5.322 (s, 2H), 4.304 (s, 2H), 4.034-4.005 (t, J=7.1 Hz, 2H), 2.698-2.654 (m, 2H), 2.170-2.141 (t, J=7.0 Hz, 2H), 2.062 (s, 3H), 2.082-2.049 (m, 2H), 1.811-1.619 (m, 4H), 1.296-1.268 (m, 2H).

TABLE 5

Compounds prepared following the procedure for Examples 74 and 75

| Ex. # | Int-A | Int-B | Compound and Name | MS [M + H]+ |
|---|---|---|---|---|
| 76 | 35 | 37 | 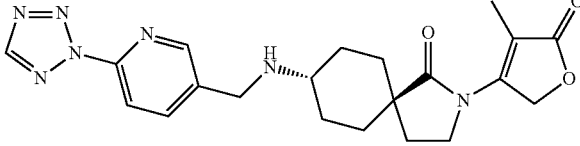<br>(5r,8r)-8-(((6-(2H-tetrazol-2-yl)pyridin-3-yl)methyl)amino)-2-(4-methyl-5-oxo-2,5-dihydrofuran-3-yl)-2-azaspiro[4.5]decan-1-one | 424.3 |
| 77 | 29A | 36 | 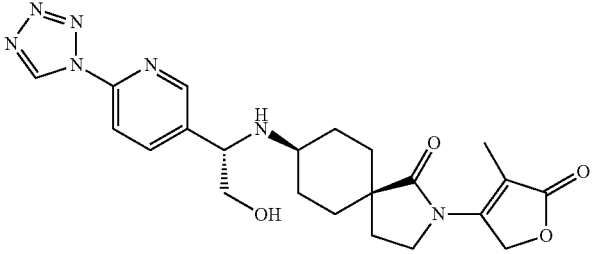<br>(5R,8S)-8-(((S)-1-(6-(1H-tetrazol-1-yl)pyridin-3-yl)-2-hydroxyethyl)amino)-2-(4-methyl-5-oxo-2,5-dihydrofuran-3-yl)-2-azaspiro[4.5]decan-1-one | 454.3 |

Example 78

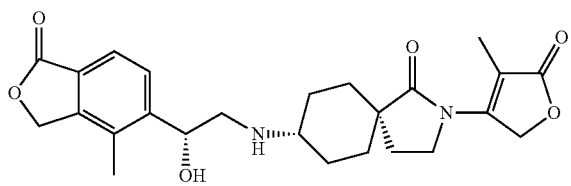 [SMILES: CC1=C(N2CC[C@]3(CC[C@@H](NC[C@H](O)c4ccc5c(c4C)COC5=O)CC3)C2=O)COC1=O]

(5r,8r)-8-(((R)-2-hydroxy-2-(4-methyl-1-oxo-1,3-dihydroisobenzofuran-5-yl)ethyl)amino)-2-(4-methyl-5-oxo-2,5-dihydrofuran-3-yl)-2-azaspiro[4.5]decan-1-one

Example 79

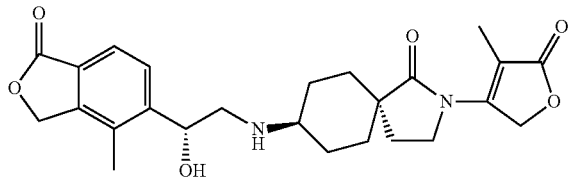 [SMILES: CC1=C(N2CC[C@]3(CC[C@H](NC[C@H](O)c4ccc5c(c4C)COC5=O)CC3)C2=O)COC1=O]

(5S,8s)-8-{[(2R)-2-hydroxy-2-(4-methyl-1-oxo-1,3-dihydro-2-benzo furan-5-yl)ethyl]amino}-2-(4-methyl-5-oxo-2,5-dihydrofuran-3-yl)-2-azaspiro[4.5]decan-1-one To a microwave tube charged with 8-amino-2-(4-methyl-5-oxo-2,5-dihydrofuran-3-yl)-2-azaspiro[4.5]decan-1-one (Intermediate 37A, 30 mg, 0.12 mmol) and (R)-4-methyl-5-(oxiran-2-yl)isobenzofuran-1(3H)-one (Intermediate 31A/31B, 33 mg, 0.18) and a stir bar was added EtOH (2 mL). The mixture was sealed and heated to 145° C. for 1.5 hr by microwave irradiation. The solvent was removed under vacuum, and the residue was separated by preparative TLC (20% methanol in ethyl acetate) to give both (5R,8r)-8-4 (R)-2-hydroxy-2-(4-methyl-1-oxo-1,3-dihydroisobenzo-furan-5-yl)ethyl)amino)-2-(4-methyl-5-oxo-2,5-dihydro-furan-3-yl)-2-azaspiro[4.5]decan-1-one and (5S,8s)-8-{[(2R)-2-hydroxy-2-(4-methyl-1-oxo-1,3-dihydro-2-benzo furan-5-yl)ethyl]amino}-2-(4-methyl-5-oxo-2,5-dihydro-furan-3-yl)-2-azaspiro[4.5]decan-1-one. MS: m/z 455.2 (M+H)+.

Example 80

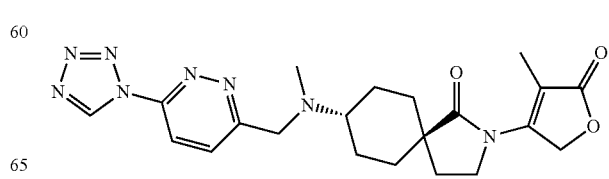

(5r,8r)-2-(4-methyl-5-oxo-2,5-dihydrofuran-3-yl)-8-(methyl{[6-(1H-tetrazol-1-yl)pyridazin-3-yl]methyl}amino)-2-azaspiro[4.5]decan-1-one

Step A: (5r,8r)-8-(((6-(1H-tetrazol-1-yl)pyridazin-3-yl)methyl)amino)-2-(4-methyl-5-oxo-2,5-dihydrofuran-3-yl)-2-azaspiro[4.5]decan-1-one To 6-(1H-tetrazol-1-yl)pyridazine-3-carbaldehyde (Intermediate 1, 4.0 g, 21.5 mmol) in 80 mL of MeOH and 80 mL of DCM was added (5r,8r)-8-amino-2-(4-methyl-5-oxo-2,5-dihydrofuran-3-yl)-2-azaspiro[4.5]decan-1-one (INTERMEDIATE 37A, 5.7 g, 21.5 mmol) and Ti(i-PrO)$_4$ (18 g, 64 mmol). The resulting mixture was stirred at room temperature for 2 hr, then NaBH$_3$CN (1.6 g, 26 mmol) was added. The resultant mixture was stirred for another 0.5 hr. Water (50 mL) was added and the mixture was filtered. The solid was washed with DCM and MeOH. The filtrate was concentrated. The residue was purified by flash chromatography (0-5% methanol in dichloromethane) to afford the title compound.

Step B: (5r,8r)-2-(4-methyl-5-oxo-2,5-dihydrofuran-3-yl)-8-(methyl{[6-(1H-tetrazol-1-yl)pyridazin-3-yl]methyl}amino)-2-azaspiro[4.5]decan-1-one To a solution of (5r,8r)-8-(((6-(1H-tetrazol-1-yl)pyridazin-3-yl)methyl)amino)-2-(4-methyl-5-oxo-2,5-dihydrofuran-3-yl)-2-azaspiro[4.5]decan-1-one (0.25 g, 0.58 mmol) in MeOH (3 mL) was added HCHO (37% aq. 1 mL). The mixture was stirred at room temperature for 18 hr. NaBH$_3$CN (40 mg) was added, and the mixture was stirred for another 1 hr. The reaction was evaporated to dryness, purified by pre-TLC (EtOAc: MeOH=5:1). The mixture of two isomers was separated by chiral SFC [eluting with 40% EtOH (0.05% DEA)/CO$_2$ on CHIRALPAK AS column], fast eluting to afford the title compound.

TABLE 6

| Ex. # | Int-A | Int-B | Compound and Name | MS [M + H]$^+$ |
|---|---|---|---|---|
| 81 | 14 | 37 | (5s,8s)-8-{methyl[(4-methyl-1-oxo-1,3-dihydro-2-benzofuran-5-yl)methyl]amino}-2-(4-methyl-5-oxo-2,5-dihydrofuran-3-yl)-2-azaspiro[4.5]decan-1-one | 439.2 |
| 82 | 14 | 37 | (5r,8r)-8-{methyl[(4-methyl-1-oxo-1,3-dihydro-2-benzofuran-5-yl)methyl]amino}-2-(4-methyl-5-oxo-2,5-dihydrofuran-3-yl)-2-azaspiro[4.5]decan-1-one | 439.2 |
| 83 | 2 | 37 | (5s,8s)-2-(4-methyl-5-oxo-2,5-dihydrofuran-3-yl)-8-(methyl{[6-(1H-tetrazol-1-yl)pyridin-3-yl]methyl}amino)-2-azaspiro[4.5]decan-1-one | 438.2 |

TABLE 6-continued

Compounds prepared following the procedure for EXAMPLE 80

| Ex. # | Int-A | Int-B | Compound and Name | MS [M + H]+ |
|---|---|---|---|---|
| 84 | 2 | 37 | 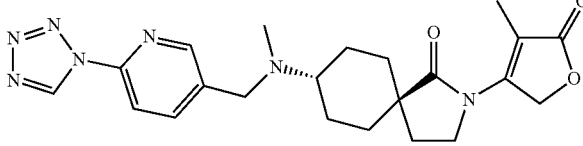(5r,8r)-2-(4-methyl-5-oxo-2,5-dihydrofuran-3-yl)-8-(methyl{[6-(1H-tetrazol-1-yl)pyridin-3-yl]methyl}amino)-2-azaspiro[4,5]decan-1-one | 438.2 |
| 85 | 29A | 37 | 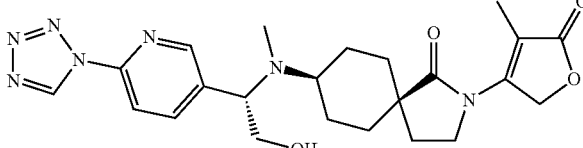(5R,8s)-8-[{(1S)-2-hydroxy-1-[6-(1H-tetrazol-1-yl)pyridin-3-yl]ethyl}(methyl)amino]-2-(4-methyl-5-oxo-2,5-dihydrofuran-3-yl)-2-azaspiro[4.5]decan-1-one | 468.2 |
| 86 | 29A | 37 | 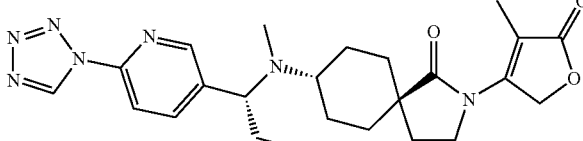5S,8r)-8-[{(1S)-2-hydroxy-1-[6-(1H-tetrazol-1-yl)pyridin-3-yl]ethyl}(methyl)amino]-2-(4-methyl-5-oxo-2,5-dihydrofuran-3-yl)-2-azaspiro[4.5]decan-1-one | 468.2 |
| 87 | 3 | 37 | 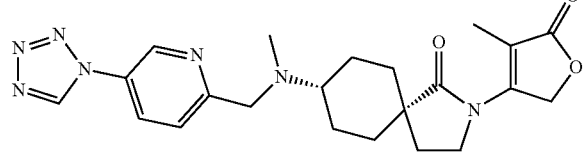(5s,8s)-2-(4-methyl-5-oxo-2,5-dihydrofuran-3-yl)-8-(methyl{[5-(1H-tetrazol-1-yl)pyridin-2-yl]methyl}amino)-2-azaspiro[4.5]decan-1- | 438.2 |
| 88 | 3 | 37 | 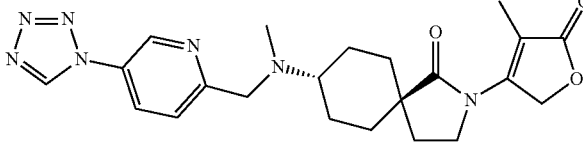(5r,8r)-2-(4-methyl-5-oxo-2,5-dihydrofuran-3-yl)-8-(methyl{[5-(1H-tetrazol-1-yl)pyridin-2-yl]methyl}amino)-2-azaspiro[4.5]decan-1-one | 438.2 |

TABLE 6-continued

Compounds prepared following the procedure for EXAMPLE 80

| Ex. # | Int-A | Int-B | Compound and Name | MS [M + H]+ |
|---|---|---|---|---|
| 89 | 10 | 37 | (5s,8s)-2-(4-methyl-5-oxo-2,5-dihydrofuran-3-yl)-8-[methyl(5H-tetrazolo[5,1-a]isoindol-7-ylmethyl)amino]-2-azaspiro[4.5]decan-1-one | 449.2 |
| 90 | 10 | 37 | (5r,8r)-2-(4-methyl-5-oxo-2,5-dihydrofuran-3-yl)-8-[methyl(5H-tetrazolo[5,1-a]isoindol-7-ylmethyl)amino]-2-azaspiro[4.5]decan-1-one | 449.2 |
| 91 | 4 | 37 | (5s,8s)-2-(4-methyl-5-oxo-2,5-dihydrofuran-3-yl)-8-(methyl{[5-(1H-tetrazol-1-yl)pyrazin-2-yl]methyl}amino)-2-azaspiro[4.5]decan-1-one | 439.1 |
| 92 | 4 | 37 | (5r,8r)-2-(4-methyl-5-oxo-2,5-dihydrofuran-3-yl)-8-(methyl{[5-(1H-tetrazol-1-yl)pyrazin-2-yl]methyl}amino)-2-azaspiro[4.5]decan-1-one | 439.1 |
| 93 | 25 | 37 | (5S,8s)-2-(4-methyl-5-oxo-2,5-dihydrofuran-3-yl)-8-(methyl{(1R)-1-[6-(1H-tetrazol-1-yl)pyridin-3-yl]ethyl}amino)-2-azaspiro[4.5]decan-1-one | 452.2 |
| 94 | 25 | 37 | (5R,8r)-2-(4-methyl-5-oxo-2,5-dihydrofuran-3-yl)-8-(methyl{(1R)-1-[6-(1H-tetrazol-1-yl)pyridin-3-yl]ethyl}amino)-2-azaspiro[4.5]decan-1-one | 452.2 |

TABLE 6-continued

Compounds prepared following the procedure for EXAMPLE 80

| Ex. # | Int-A | Int-B | Compound and Name | MS [M + H]+ |
|---|---|---|---|---|
| 95 | 25 | 37 | 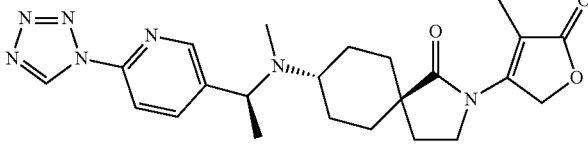<br>(5R,8r)-2-(4-methyl-5-oxo-2,5-dihydrofuran-3-yl)-8-(methyl{(1R)-1-[6-(1H-tetrazol-1-yl)pyridin-3-yl]ethyl}amino)-2-azaspiro[4.5]decan-1-one | 452.2 |
| 96 | 17 | 37 | 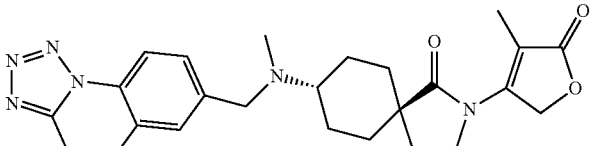<br>(5r,8r)-8-(methyl(tetrazolo[1,5-a]quinolin-7-ylmethyl)amino)-2-(4-methyl-5-oxo-2,5-dihydrofuran-3-yl)-2-azaspiro[4.5]decan-1-one | 461.2 |
| 97 | 11 | 37 | 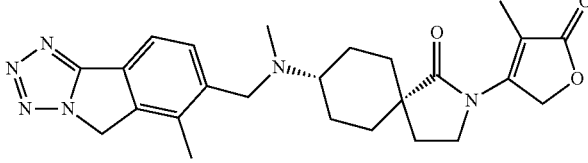<br>(5s,8s)-8-(methyl((6-methyl-5H-tetrazolo[5,1-a]isoindol-7-yl)methyl)amino)-2-(4-methyl-5-oxo-2,5-dihydrofuran-3-yl)-2-azaspiro[4.5]decan-1-one | 463.2 |
| 98 | 11 | 37 | 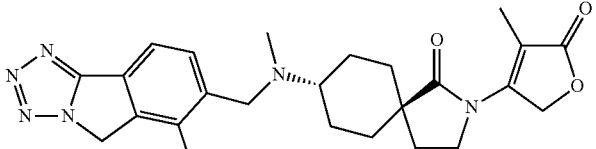<br>(5r,8r)-8-(methyl((6-methyl-5H-tetrazolo[5,1-a]isoindol-7-yl)methyl)amino)-2-(4-methyl-5-oxo-2,5-dihydrofuran-3-yl)-2-azaspiro[4.5]decan-1-one | 463.2 |
| 99 | 4 | 38B | 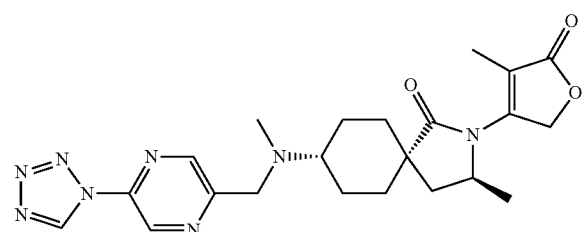<br>(3S,5s,8R)-8-(((5-(1H-tetrazol-1-yl)pyrazin-2-yl)methyl)(methyl)amino)-3-methyl-2-(4-methyl-5-oxo-2,5-dihydrofuran-3-yl)-2-azaspiro[4.5]decan-1-one | 425.2 |

TABLE 6-continued

Compounds prepared following the procedure for EXAMPLE 80

| Ex. # | Int-A | Int-B | Compound and Name | MS [M + H]+ |
|---|---|---|---|---|
| 100 | 4 | 38A | 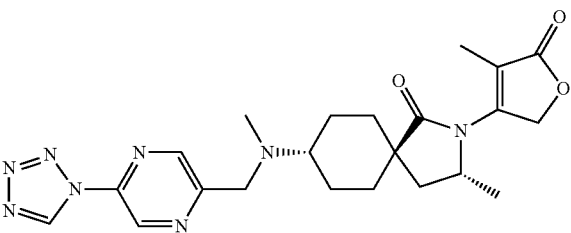(3R,5r,8R)-8-(((5-(1H-tetrazol-1-yl)pyrazin-2-yl)methyl)(methyl)amino)-3-methyl-2-(4-methyl-5-oxo-2,5-dihydrofuran-3-yl)-2-azaspiro[4.5]decan-1-one | 425.2 |
| 101 | 29B | 37 | 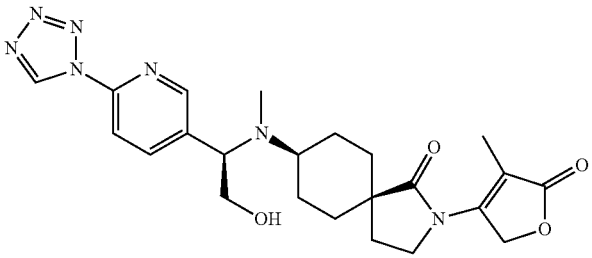(5S,8s)-8-[{(1R)-2-hydroxy-1-[6-(1H-tetrazol-1-yl)pyridin-3-yl]ethyl}(methyl)amino]-2-(4-methyl-5-oxo-2,5-dihydrofuran-3-yl)-2-azaspiro[4.5]decan-1-one | 468.2 |
| 102 | 29B | 37 | 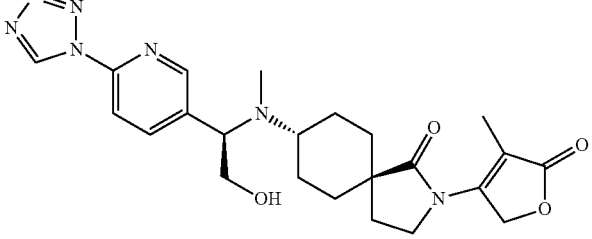(5R,8r)-8-[{(1R)-2-hydroxy-1-[6-(1H-tetrazol-1-yl)pyridin-3-yl]ethyl}(methyl)amino]-2-(4-methyl-5-oxo-2,5-dihydrofuran-3-yl)-2-azaspiro[4.5]decan-1-one | 468.2 |
| 103 | 1 | 41 | 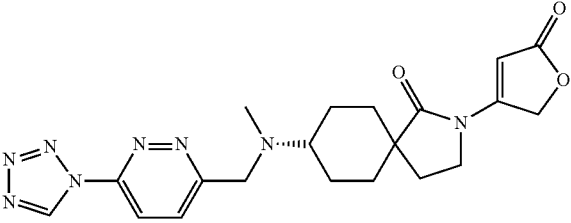8-(((6-(1H-tetrazol-1-yl)pyridazin-3-yl)methyl)(methyl)amino)-2-(5-oxo-2,5-dihydrofuran-3-yl)-2-azaspiro[4.5]decan-1-one | 425.6 |

Example 104

(3S,5r,8S)-8-(((6-(1H-tetrazol-1-yl)pyridazin-3-yl)methyl)(methyl)amino)-3-methyl-2-(5-oxo-2,5-dihydrofuran-3-yl)-2-azaspiro[4.5]decan-1-one

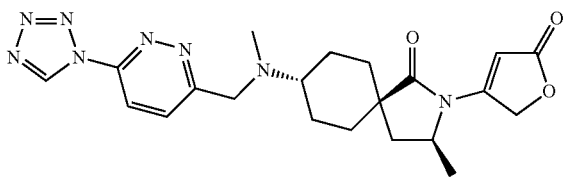 [SMILES: C[C@H]1C[C@]2(CC[C@@H](N(C)Cc3ccc(-n4cnnn4)nn3)CC2)C(=O)N1C1=CC(=O)OC1]

To a solution of (3S,5r,8S)-8-(((6-(1H-tetrazol-1-yl)pyridazin-3-yl)methyl)amino)-3-methyl-2-(5-oxo-2,5-dihydrofuran-3-yl)-2-azaspiro[4.5]decan-1-one (Intermediate 37, 0.25 g, 0.58 mmol) in MeOH (3 mL) was added HCHO (37% aq. 1 mL), the mixture was stirred at room temperature for 18 hr. Then NaBH$_3$CN (40 mg) was added, and the mixture was stirred for another 1 hour. The reaction was evaporated to dryness, purified by prep-TLC (EtOAc:MeOH=5:1) to afford the title compound.

TABLE 7

Compounds prepared following the procedure for Ex. 104

| Ex. # | SM Ex. # | Structure and Name | MS [M + H]$^+$ |
|---|---|---|---|
| 105 | 2 | (5s,8s)-8-{methyl[2-(1-oxo-1,3-dihydro-2-benzofuran-5-yl)ethyl]amino}-2-(4-methyl-5-oxo-2,5-dihydrofuran-3-yl)-2-azaspiro[4.5]decan-1-one | 439.5 |
| 106 | 11 | (5r,8r)-8-(((5H-tetrazolo[5,1-a]isoindol-7-yl)methyl)(methyl)amino)-2-(4-methyl-5-oxo-2,5-dihydrofuran-3-yl)-2-azaspiro[4.5]decan-1-one | 449.2 |
| 107 | 12 | (5r,8r)-8-(methyl((4-methyl-6-(1H-tetrazol-1-yl)pyridazin-3-yl)methyl)amino)-2-(4-methyl-5-oxo-2,5-dihydrofuran-3-yl)-2-azaspiro[4.5]decan-1-one | 453.4 |

TABLE 7-continued

Compounds prepared following the procedure for Ex. 104

| Ex. # | SM Ex. # | Structure and Name | MS [M + H]+ |
|---|---|---|---|
| 108 | 36 | 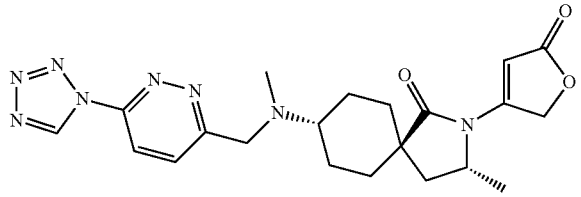<br>(3R,5r,8R)-8-(((6-(1H-tetrazol-1-yl)pyridazin-3-yl)methyl)amino)-3-methyl-2-(5-oxo-2,5-dihydrofuran-3-yl)-2-azaspiro[4.5]decan-1-one | 411.2 ([M + 1 − 28]+) |
| 109 | 41 | 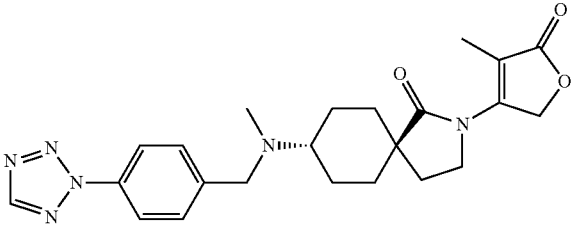<br>(5r,8r)-2-(4-methyl-5-oxo-2,5-dihydrofuran-3-yl)-8-{methyl[4-(2H-tetrazol-2-yl)benzyl]amino}-2-azaspiro[4.5]decan-1-one | 437.3 |
| 110 | 38 | 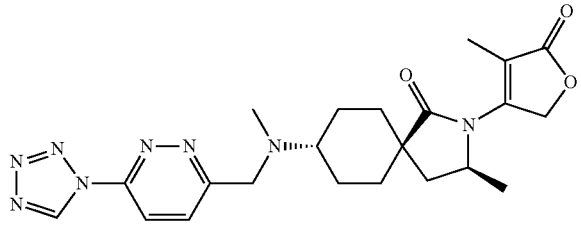<br>(3S,5r,8S)-8-(((6-(1H-tetrazol-1-yl)pyridazin-3-yl)methyl)(methyl)amino)-3-methyl-2-(4-methyl-5-oxo-2,5-dihydrofuran-3-yl)-2-azaspiro[4.5]decan-1-one | 425.2 |
| 111 | 40 | 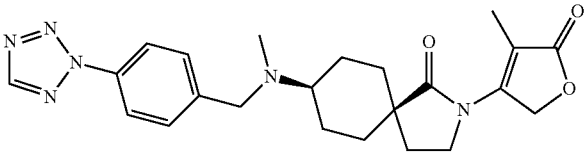<br>(5s,8s)-2-(4-methyl-5-oxo-2,5-dihydrofuran-3-yl)-8-{methyl[4-(2H-tetrazol-2-yl)benzyl]amino}-2-azaspiro[4.5]decan-1-one | 437.6 |
| 112 | 51 | 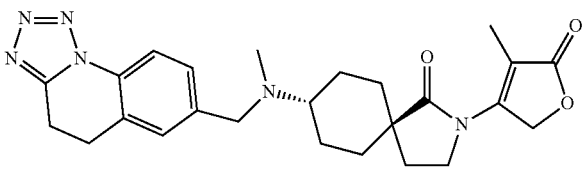<br>(5r,8r)-8-(((4,5-dihydrotetrazolo[1,5-a]quinolin-7-yl)methyl)(methyl)amino)-2-(4-methyl-5-oxo-2,5-dihydrofuran-3-yl)-2-azaspiro[4.5]decan-1-one | 463.2 |

TABLE 7-continued

Compounds prepared following the procedure for Ex. 104

| Ex. # | SM Ex. # | Structure and Name | MS [M + H]+ |
|---|---|---|---|
| 113 | 75 | 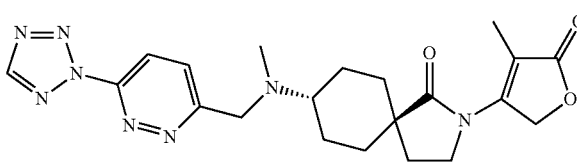<br>(5r,8r)-2-(4-methyl-5-oxo-2,5-dihydrofuran-3-yl)-8-(methyl{[6-(2H-tetrazol-2-yl)pyridazin-3-yl]methyl}amino)-2-azaspiro[4.5]decan-1-one | 439.6 |
| 114 | 74 | 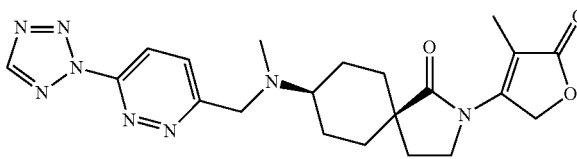<br>(5s,8s)-2-(4-methyl-5-oxo-2,5-dihydrofuran-3-yl)-8-(methyl{[6-(2H-tetrazol-2-yl)pyridazin-3-yl]methyl}amino)-2-azaspiro[4.5]decan-1-one | 439.6 |
| 115 | 42 | 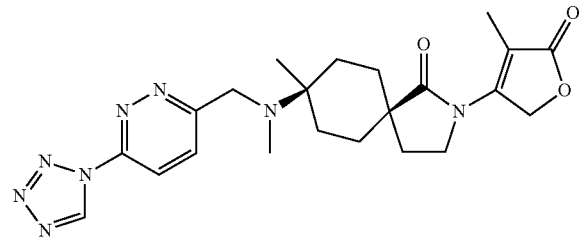<br>(5s,8s)-8-methyl-2-(4-methyl-5-oxo-2,5-dihydrofuran-3-yl)-8-(methyl{[6-(1H-tetrazol-1-yl)pyridazin-3-yl]methyl}amino)-2-azaspiro[4.5]decan-1-one | 453.6 |
| 116 | 48 | 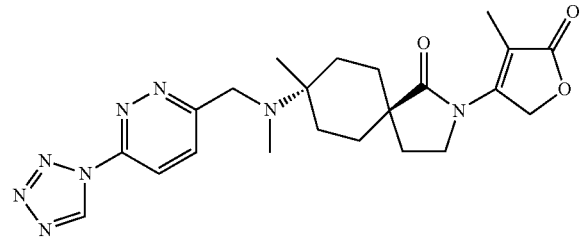<br>(5r,8r)-8-methyl-2-(4-methyl-5-oxo-2,5-dihydrofuran-3-yl)-8-(methyl{[6-(1H-tetrazol-1-yl)pyridazin-3-yl]methyl}amino)-2-azaspiro[4.5]decan-1-one | 453.6 |
| 117 | 76 | 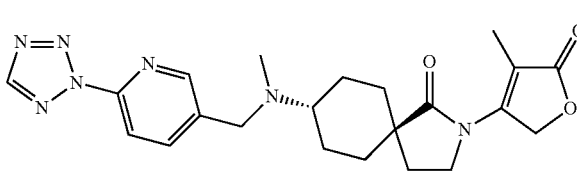<br>(5r,8r)-8-(((6-(2H-tetrazol-2-yl)pyridin-3-yl)methyl)(methyl)amino)-2-(4-methyl-5-oxo-2,5-dihydrofuran-3-yl)-2-azaspiro[4.5]decan-1-one | 437.6 |

US 9,718,808 B2

TABLE 7-continued

Compounds prepared following the procedure for Ex. 104

| Ex. # | SM Ex. # | Structure and Name | MS [M + H]+ |
|---|---|---|---|
| 118 | 39 | 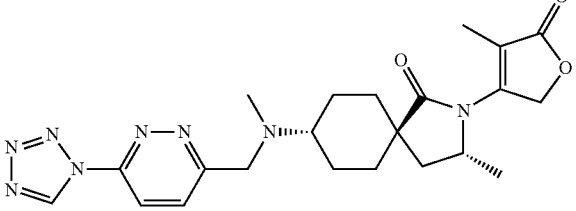<br>(3R,5r,8R)-8-(((6-(1H-tetrazol-1-yl)pyridazin-3-yl)methyl)(methyl)amino)-3-methyl-2-(4-methyl-5-oxo-2,5-dihydrofuran-3-yl)-2-azaspiro[4.5]decan-1-one | 425.2 |
| 119 | 55 | 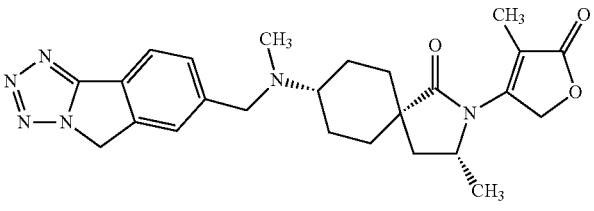<br>(3R,5s,8S)-8-(((5H-tetrazolo[5,1-a]isoindol-7-yl)methyl)(methyl)amino)-3-methyl-2-(4-methyl-5-oxo-2,5-dihydrofuran-3-yl)-2-azaspiro[4.5]decan-1-one | 439.6 |
| 120 | 56 | 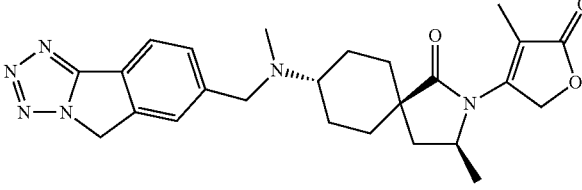<br>(3S,5r,8S)-8-(((5H-tetrazolo[5,1-a]isoindol-7-yl)methyl)(methyl)amino)-3-methyl-2-(4-methyl-5-oxo-2,5-dihydrofuran-3-yl)-2-azaspiro[4.5]decan-1-one | 463.2 |
| 121 | 59 | 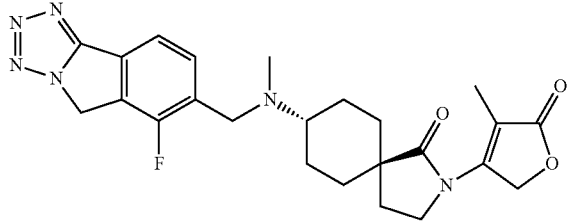<br>(5r,8r)-8-(((6-fluoro-5H-tetrazolo[5,1-a]isoindol-7-yl)methyl)(methyl)amino)-2-(4-methyl-5-oxo-2,5-dihydrofuran-3-yl)-2-azaspiro[4.5]decan-1-one | 467.4 |
| 122 | 61 | 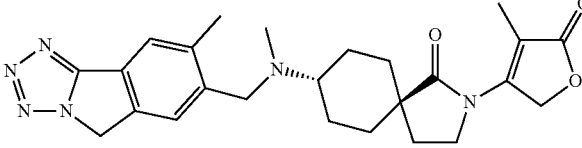<br>(5r,8r)-8-(methyl((8-methyl-5H-tetrazolo[5,1-a]isoindol-7-yl)methyl)amino)-2-(4-methyl-5-oxo-2,5-dihydrofuran-3-yl)-2-azaspiro[4.5]decan-1-one | 463.2 |

TABLE 7-continued

Compounds prepared following the procedure for Ex. 104

| Ex. # | SM Ex. # | Structure and Name | MS [M + H]+ |
|---|---|---|---|
| 123 | 79 | (5S,8s)-8-{[(2R)-2-hydroxy-2-(4-methyl-1-oxo-1,3-dihydro-2-benzofuran-5-yl)ethyl](methyl)amino}-2-(4-methyl-5-oxo-2,5-dihydrofuran-3-yl)-2-azaspiro[4.5]decan-1-one | 469.5 |
| 124 | 78 | 8-{[(2R)-2-hydroxy-2-(4-methyl-1-oxo-1,3-dihydro-2-benzofuran-5-yl)ethyl](methyl)amino}-2-(4-methyl-5-oxo-2,5-dihydrofuran-3-yl)-2-azaspiro[4.5]decan-1-one | 469.4 |
| 125 | 14 | (5r,8r)-8-(methyl((3-methyl-5-(1H-tetrazol-1-yl)pyrazin-2-yl)methyl)amino)-2-(4-methyl-5-oxo-2,5-dihydrofuran-3-yl)-2-azaspiro[4.5]decan-1-one | 453.4 |
| 126 | 67 | (5r,8r)-8-(((2-(1H-tetrazol-1-yl)thiazol-5-yl)methyl)(methyl)amino)-2-(4-methyl-5-oxo-2,5-dihydrofuran-3-yl)-2-azaspiro[4.5]decan-1-one | 416.2 |
| 127 | 68 | (5s,8s)-8-(((5-(1H-tetrazol-1-yl)pyrazin-2-yl)methyl)(methyl)amino)-8-methyl-2-(4-methyl-5-oxo-2,5-dihydrofuran-3-yl)-2-azaspiro[4.5]decan-1-one | 453.3 |

TABLE 7-continued

Compounds prepared following the procedure for Ex. 104

| Ex. # | SM Ex. # | Structure and Name | MS [M + H]+ |
|---|---|---|---|
| 128 | 72 | 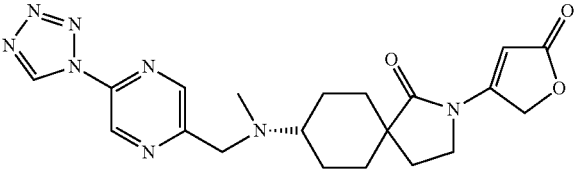<br>8-(((5-(1H-tetrazol-1-yl)pyrazin-2-yl)methyl)(methyl)amino)-2-(5-oxo-2,5-dihydrofuran-3-yl)-2-azaspiro[4.5]decan-1-one | 425.2 |
| 129 | 69 | 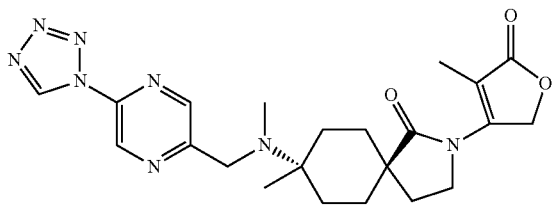<br>(5r,8r)-8-(((5-(1H-tetrazol-1-yl)pyrazin-2-yl)methyl)(methyl)amino)-8-methyl-2-(4-methyl-5-oxo-2,5-dihydrofuran-3-yl)-2-azaspiro[4.5]decan-1-one | 453.2 |

Method A

Example 130

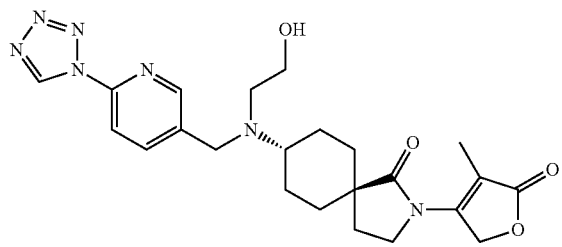 [SMILES: CC1=C(N2CC[C@]3(CC[C@@H](N(CCO)Cc4ccc(-n5cnnn5)nc4)CC3)C2=O)COC1=O]

(5r,8r)-8-(((6-(1H-tetrazol-1-yl)pyridin-3-yl)methyl)(2-hydroxyethyl)amino)-2-(4-methyl-5-oxo-2,5-dihydrofuran-3-yl)-2-azaspiro[4.5]decan-1-one

Example 131

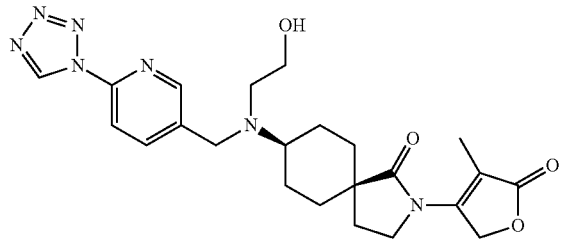 [SMILES: CC1=C(N2CC[C@]3(CC[C@H](N(CCO)Cc4ccc(-n5cnnn5)nc4)CC3)C2=O)COC1=O]

(5s,8s)-8-[(2-hydroxyethyl){[6-(1H-tetrazol-1-yl)pyridin-3-yl]methyl}amino]-2-(4-methyl-5-oxo-2,5-dihydrofuran-3-yl)-2-azaspiro[4.5]decan-1-one To a solution of 8-(((6-(1H-tetrazol-1-yl)pyridin-3-yl)methyl)amino)-2-(4-methyl-5-oxo-2,5-dihydrofuran-3-yl)-2-azaspiro[4.5]decan-1-one (Example 5, a mixture of two isomers, 250 mg, 0.60 mmol) in CH$_3$CN (20 mL) was added a base (t-BuOK for this example, 200 mg, 1.77 mmol) and 2-bromoethanol (222 mg, 1.77 mmol). The mixture was stirred at 70° C. for 16 hr, and quenched with 1 N hydrochloric acid. The aqueous layer was extracted with CH$_2$Cl$_2$ (40 mL×3). The combined organic layers were washed with brine, dried over MgSO$_4$, and concentrated. The residue was purified by prep TLC (10% methanol in dichloromethane) followed by chiral SFC [eluting with 40% MeOH (0.05% DEA)/CO$_2$ on CHIRALPAK AS-H column] to afford the title compounds (5r,8r)-8-(((6-(1H-tetrazol-1-yl)pyridin-3-yl)methyl)(2-hydroxyethyl)amino)-2-(4-methyl-5-oxo-2,5-dihydrofuran-3-yl)-2-azaspiro[4.5]decan-1-one (fast eluting) and (5s,8s)-8-[(2-hydroxyethyl){[6-(1H-tetrazol-1-yl)pyridin-3-yl]methyl}amino]-2-(4-methyl-5-oxo-2,5-dihydrofuran-3-yl)-2-azaspiro[4.5]decan-1-one (slow eluting). MS (ESI, m/z): 468 [M+H]+.

119
Method B

Example 132

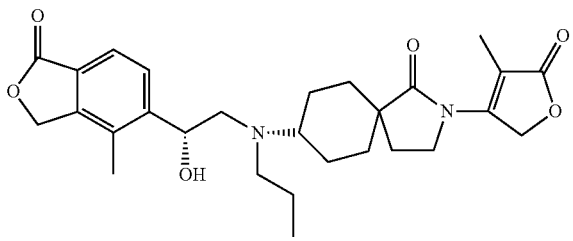

120

8-{[(2R)-2-hydroxy-2-(4-methyl-1-oxo-1,3-dihydro-2-benzofuran-5-yl)ethyl](propyl)amino}-2-(4-methyl-5-oxo-2,5-dihydrofuran-3-yl)-2-azaspiro[4.5]decan-1-one To a solution of (5r,8r)-8-(((R)-2-hydroxy-2-(4-methyl-1-oxo-1,3-dihydroisobenzofuran-5-yl)ethyl)amino)-2-(4-methyl-5-oxo-2,5-dihydrofuran-3-yl)-2-azaspiro[4.5]decan-1-one (Example 78, 100 mg, 0.220 mmol) and propionaldehyde (0.032 ml, 0.440 mmol) in DCM (15 ml) was added sodium triacetoxyhydroborate (140 mg, 0.660 mmol) and a few drops of AcOH at rt. The mixture was stirred at the same temperature for 60 min, quenched with NaHCO₃ aqueous. The organic layer was separated and the aqueous was extracted with DCM (20 ml). The combined organic layers were dried (MgSO₄) and concentrated. The residue was purified by prep-TLC (20% MeOH in EtOAc). MS [M+H]⁺=496.97.

TABLE 8

| | | Compounds prepared following the procedure for EXAMPLE 132 | | |
|---|---|---|---|---|
| Ex. # | SM-A | SM-B | Structure and Name | MS [M + H]⁺ |
| 133 | CHO | Ex. 11 | (5r,8r)-8-(((5H-tetrazolo[5,1-a]isoindol-7-yl)methyl)(ethyl)amino)-2-(4-methyl-5-oxo-2,5-dihydrofuran-3-yl)-2-azaspiro[4.5]decan-1-one | 463.2 |
| 134 | CHO | Ex. 5 | (5s,8s)-8-(ethyl{[6-(1H-tetrazol-1-yl)pyridin-3-yl]methyl}amino)-2-(4-methyl-5-oxo-2,5-dihydrofuran-3-yl)-2-azaspiro[4.5]decan-1-one | 452.2 |
| 135 | CHO (oxazole) | Ex. 1 | (5r,8r)-8-(((6-(1H-tetrazol-1-yl)pyridazin-3-yl)methyl)(oxazol-2-ylmethyl)amino)-2-(4-methyl-5-oxo-2,5-dihydrofuran-3-yl)-2-azaspiro[4.5]decan-1-one | 478.2 ([M + 1 − 28]⁺) |

TABLE 8-continued

Compounds prepared following the procedure for EXAMPLE 132

| Ex. # | SM-A | SM-B | Structure and Name | MS [M + H]+ |
|---|---|---|---|---|
| 136 | OH–CH2CH2–Br | Ex. 7 5S Isomer | (5s,8s)-8-[(2-hydroxyethyl){[5-(1H-tetrazol-1-yl)pyridin-2-yl]methyl}amino]-2-(4-methyl-5-oxo-2,5-dihydrofuran-3-yl)-2-azaspiro[4.5]decan-1-one | 468.2 |
| 137 | OH–CH2CH2–Br | Ex. 1 | (5r,8r)-8-[(2-hydroxyethyl){[6-(1H-tetrazol-1-yl)pyridazin-3-yl]methyl}amino]-2-(4-methyl-5-oxo-2,5-dihydrofuran-3-yl)-2-azaspiro[4.5]decan-1-one | 468.2 |
| 138 | CH3CHO | Ex. 7 5s, 8s isomer | (5s,8s)-8-(ethyl{[5-(1H-tetrazol-1-yl)pyridin-2-yl]methyl}amino)-2-(4-methyl-5-oxo-2,5-dihydrofuran-3-yl)-2-azaspiro[4.5]decan-1-one | 452.2 |
| 139 | Me2N–C(O)–CH2–Cl | Ex. 6 5s, 8s isomer | N,N-dimethyl-N~2~-[(5s,8s)-2-(4-methyl-5-oxo-2,5-dihydrofuran-3-yl)-1-oxo-2-azaspiro[4.5]dec-8-yl]-N~2~-{[6-(1H-tetrazol-1-yl)pyridin-3-yl]methyl}glycinamide | 509.2 |

TABLE 8-continued

Compounds prepared following the procedure for EXAMPLE 132

| Ex. # | SM-A | SM-B | Structure and Name | MS [M + H]+ |
|---|---|---|---|---|
| 140 | NH2-CO-CH2-Cl | Ex. 6 5s, 8s isomer | N~2~-[(5s,8s)-2-(4-methyl-5-oxo-2,5-dihydrofuran-3-yl)-1-oxo-2-azaspiro[4.5]dec-8-yl]-N~2~-{[6-(1H-tetrazol-1-yl)pyridin-3-yl]methyl}glycinamide | 481.2 |
| 141 | NH2-CO-CH2-Cl | Ex. 5 | N~2~-[(5r,8r)-2-(4-methyl-5-oxo-2,5-dihydrofuran-3-yl)-1-oxo-2-azaspiro[4.5]dec-8-yl]-N~2~-{[6-(1H-tetrazol-1-yl)pyridin-3-yl]methyl}glycinamide | 481.2 |
| 142 | CHO | Ex. 3 | 8-{ethyl[(4-methyl-1-oxo-1,3-dihydro-2-benzofuran-5-yl)methyl]amino}-2-(4-methyl-5-oxo-2,5-dihydrofuran-3-yl)-2-azaspiro[4.5]decan-1-one | 453.2 |

Thallium Flux Assay

A Thallium Flux Assay was performed on each of the final product compounds of the Examples. This assay has been described previously; see, e.g., PCT Published Application WO 2013/062900.

Data collected for compounds in the Examples of the present invention using the Thallium Flux Assay are shown in Table 10 below. All of the tested final product compounds in the Examples (diastereomeric mixtures and individual diastereomers) had $IC_{50}$ potencies less than 1 µM in the Thallium Flux Assay.

TABLE 10

| Ex. No. | Thallium Flux IC50 (µM) |
|---|---|
| 1 | 0.01 |
| 2 | 0.044 |
| 3 | 0.20 |
| 4 | 0.35 |
| 5 | 0.016 |
| 6 | 0.45 |
| 7 | 0.024 |
| 8 | 0.71 |
| 9 | 0.034 |

TABLE 10-continued

| Ex. No. | Thallium Flux IC50 (μM) |
|---|---|
| 10 | 0.018 |
| 11 | 0.11 |
| 12 | 0.0083 |
| 13 | 0.032 |
| 14 | 0.030 |
| 15 | 0.092 |
| 16 | 0.32 |
| 17 | 0.34 |
| 18 | 0.33 |
| 19 | 0.028 |
| 20 | 0.17 |
| 21 | 0.044 |
| 22 | 0.13 |
| 23 | 0.72 |
| 24 | 0.12 |
| 25 | 0.26 |
| 26 | 0.19 |
| 27 | 0.038 |
| 28 | 0.25 |
| 29 | 0.020 |
| 30 | 0.15 |
| 31 | 0.26 |
| 32 | 0.11 |
| 33 | 0.046 |
| 34 | 0.0084 |
| 35 | 0.0084 |
| 36 | 0.11 |
| 37 | 0.030 |
| 38 | 0.040 |
| 39 | 0.023 |
| 40 | 0.11 |
| 41 | 0.0033 |
| 42 | 0.070 |
| 43 | 0.049 |
| 44 | 0.0031 |
| 45 | 0.019 |
| 46 | 0.18 |
| 47 | 0.55 |
| 48 | 0.0077 |
| 49 | 0.24 |
| 50 | 0.039 |
| 51 | 0.0043 |
| 52 | 0.16 |
| 53 | 0.019 |
| 54 | 0.032 |
| 55 | 0.015 |
| 56 | 0.52 |
| 57 | 0.42 |
| 58 | 0.18 |
| 59 | 0.0060 |
| 60 | 0.65 |
| 61 | 0.023 |
| 62 | 0.020 |
| 63 | 0.023 |
| 64 | 0.065 |
| 65 | 0.019 |
| 66 | 0.0070 |
| 67 | 0.092 |
| 68 | 0.14 |
| 69 | 0.015 |
| 70 | 0.024 |
| 71 | 0.19 |
| 72 | 0.34 |
| 73 | 2 |
| 74 | 0.21 |
| 75 | 0.0093 |
| 76 | 0.18 |
| 77 | 0.36 |
| 78 | 0.21 |
| 79 | 0.28 |
| 80 | 0.019 |
| 81 | 1.18 0.69 |
| 82 | 0.13 0.054 |
| 83 | 0.028 |
| 84 | 0.74 |
| 85 | 0.19 |
| 86 | 0.48 |
| 87 | 0.55 |
| 88 | 0.007 |
| 89 | 0.95 |
| 90 | 0.022 |
| 91 | 0.69 |
| 92 | 0.029 |
| 93 | 0.51 |
| 94 | 0.011 |
| 95 | 0.024 |
| 96 | 0.021 |
| 97 | 0.17 |
| 98 | 0.0097 |
| 99 | 0.31 |
| 100 | 0.20 |
| 101 | 0.29 |
| 102 | 0.30 |
| 103 | 0.087 |
| 104 | 0.041 |
| 105 | 0.15 |
| 106 | 0.0088 |
| 107 | 0.022 |
| 108 | 0.27 |
| 109 | 0.0034 |
| 110 | 0.20 |
| 111 | 0.30 |
| 112 | 0.032 |
| 113 | 0.036 |
| 114 | 0.43 |
| 115 | 0.015 |
| 116 | 0.024 |
| 117 | 0.64 |
| 118 | 0.20 |
| 119 | 0.018 |
| 120 | 0.043 |
| 121 | 0.023 |
| 122 | 0.026 |
| 123 | 0.077 |
| 124 | 0.064 |
| 125 | 0.022 |
| 126 | 0.030 |
| 127 | 0.091 |
| 128 | 0.093 |
| 129 | 0.045 |
| 130 | 0.030 |
| 131 | 0.16 |
| 132 | 0.10 |
| 133 | 0.036 |
| 134 | 0.47 |
| 135 | 0.21 |
| 136 | 0.16 |
| 137 | 0.15 |
| 138 | 0.034 |
| 139 | 0.12 |
| 140 | 0.11 |
| 141 | 0.68 |
| 142 | 0.49 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I

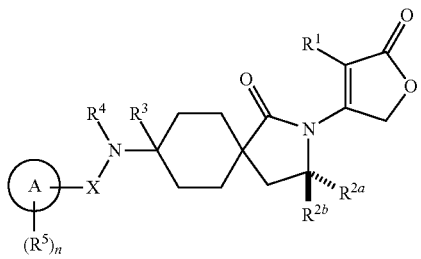

or a pharmaceutically acceptable salt thereof wherein:
ring A is
- (1) aryl, wherein the aryl ring is unsubstituted or substituted by $R^6$
- (2) 5- or 6-membered heteroaryl, containing 1-3 heteroatoms independently selected from the group consisting of N, O, and S, wherein the heteroaryl ring is substituted by $R^6$, or
- (3) fused tricyclic heteroaryl, containing 2-6 N heteroatoms;

$R^1$ is
- (1) hydrogen, or
- (2) $(C_{1-3})$alkyl;

$R^{2a}$ and $R^{2b}$ are independently
- (1) hydrogen, or
- (2) $(C_{1-3})$alkyl;

$R^3$ is
- (1) hydrogen, or
- (2) $(C_{1-3})$alkyl;

$R^4$ is
- (1) hydrogen,
- (2) $(C_{1-6})$alkyl,
- (3) hydroxy$(C_{1-6})$alkyl,
- (4) $(C_{1-3})$alkylC(O)N$(R^7)_2$, or
- (5) $(C_{1-3})$alkyl-heteroaryl, wherein heteroaryl is a 5- or 6-membered monocyclic ring and contains 1-3 heteroatoms independently selected from the group consisting of N, O, and S;

each $R^5$ is
- (1) oxo
- (2) $(C_{1-3})$alkyl, or
- (3) halo;

$R^6$ is a five-membered heteroaryl containing 1-4 heteroatoms independently selected from the group consisting of N, O, and S;

each $R^7$ is
- (1) hydrogen, or
- (2) $(C_{1-3})$alkyl;

X is —$(C_{1-3})$alkyl-, optionally substituted by hydroxy; and n is 0, 1, 2, or 3.

2. The compound of claim 1 or a pharmaceutically acceptable salt thereof, wherein:
X is

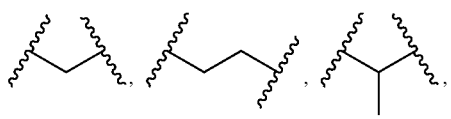

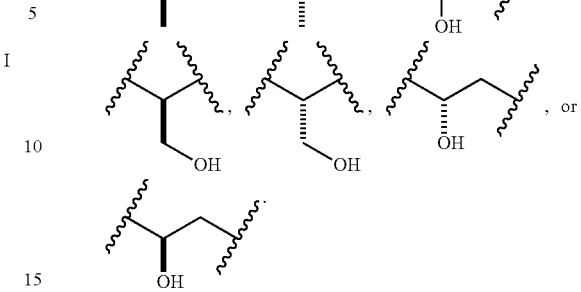

3. The compound of claim 1 or a pharmaceutically acceptable salt thereof, wherein $R^1$ is hydrogen or methyl.

4. The compound of claim 1 or a pharmaceutically acceptable salt thereof wherein ring A is phenyl, wherein the aryl ring is substituted by $R^6$.

5. The compound of claim 1 or a pharmaceutically acceptable salt thereof wherein ring A is 5- or 6-membered heteroaryl, containing 1-3 heteroatoms independently selected from the group consisting of N, O, and S, wherein the heteroaryl ring is substituted by $R^6$.

6. The compound of claim 5 or a pharmaceutically acceptable salt thereof, wherein ring A is pyridinyl, pyrazinyl, pyridazinyl, or thiazolyl, wherein each ring is substituted by $R^6$.

7. The compound of claim 4 or a pharmaceutically acceptable salt thereof, wherein $R^6$ is tetrazolyl.

8. The compound of claim 1 or a pharmaceutically acceptable salt thereof, wherein ring A is 1,3-dihydroisobenzofuran.

9. The compound of claim 1 or a pharmaceutically acceptable salt thereof, wherein ring A is 5H-tetrazolo[5,1-a]isoindole, 4,5-dihydrotetrazolo[1,5-a]quinolone, 8H-tetrazolo[1',5':1,2]pyrrolo[3,4-b]pyridine, or tetrazolo[1,5-a]quinoline.

10. The compound having structural Formula I-d

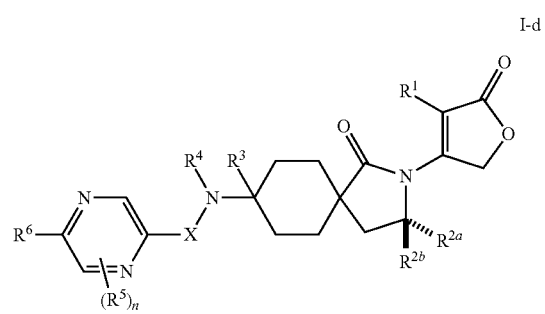

or a pharmaceutically acceptable salt thereof, wherein:
$R^1$ is hydrogen or methyl;
$R^{2a}$ and $R^{2b}$ are independently hydrogen, or methyl;
$R^3$ is hydrogen or methyl;
$R^4$ is hydrogen or methyl;
$R^5$ is methyl;
$R^6$ is tetrazolyl;

X is
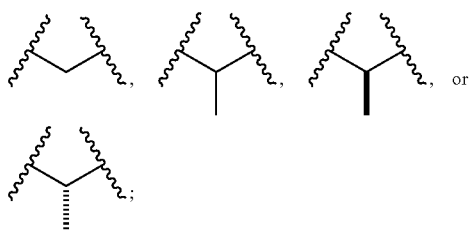
and
n is 0, 1, or 2.
11. The compound of claim 1 which is:
1
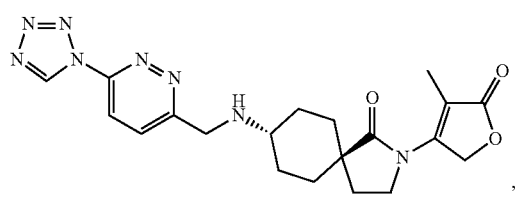
2
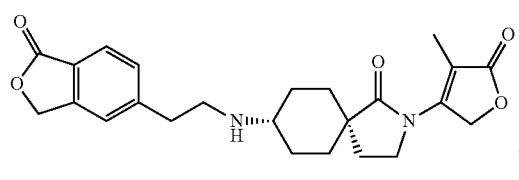
3
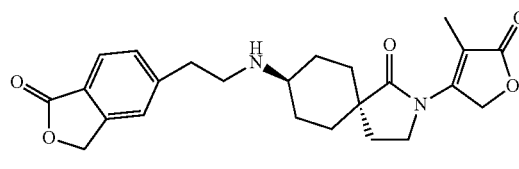
4
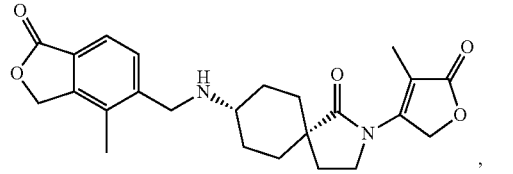
5
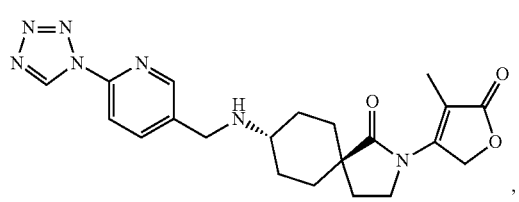
6
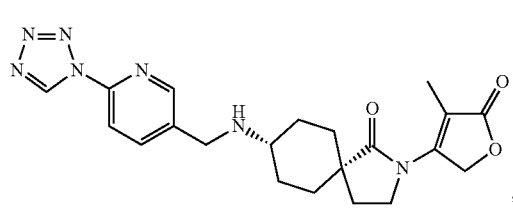
7
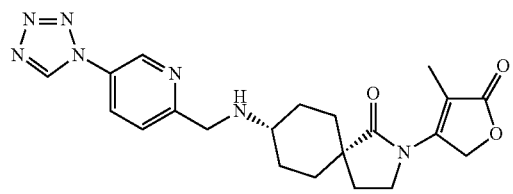
8
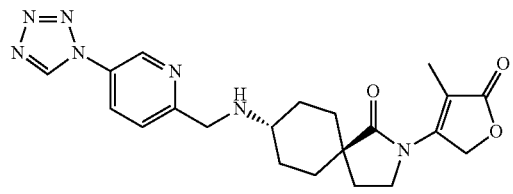
9
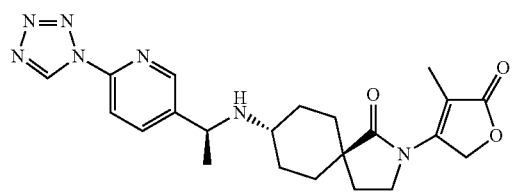
10
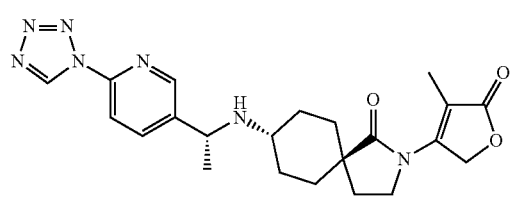
11
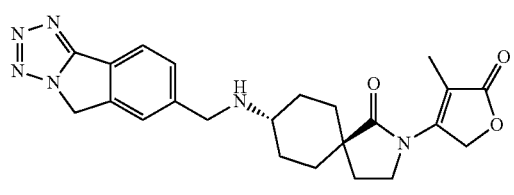
12
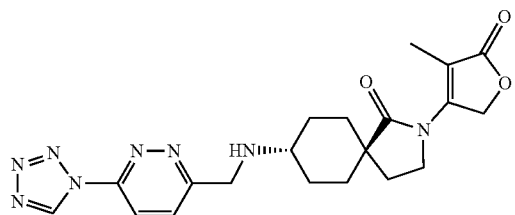
13
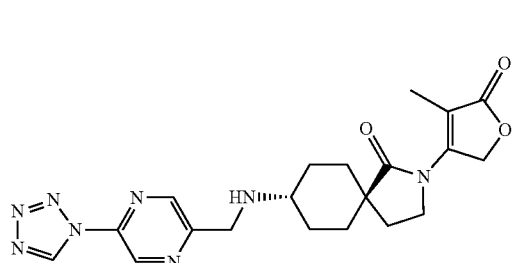

14
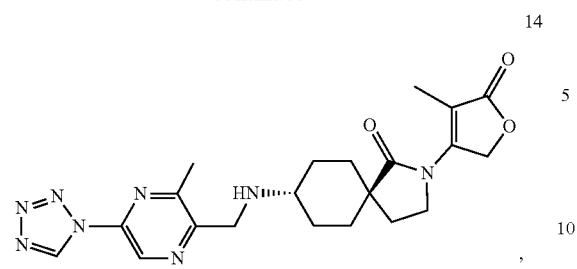
15
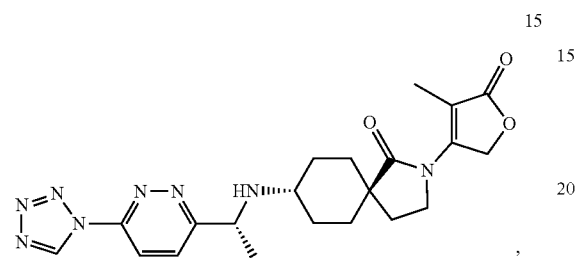
16
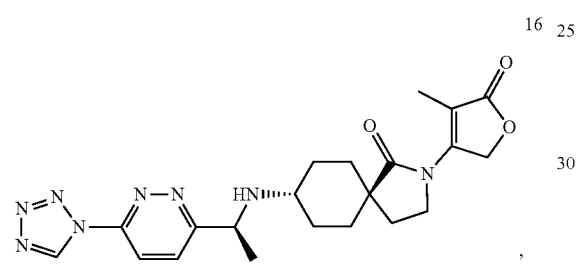
17
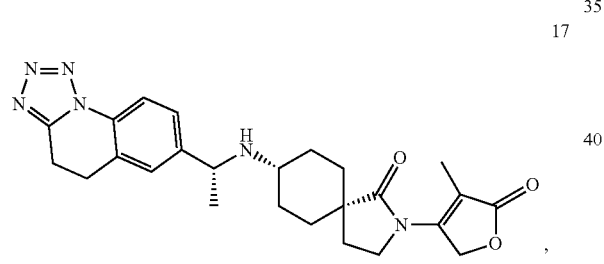
18
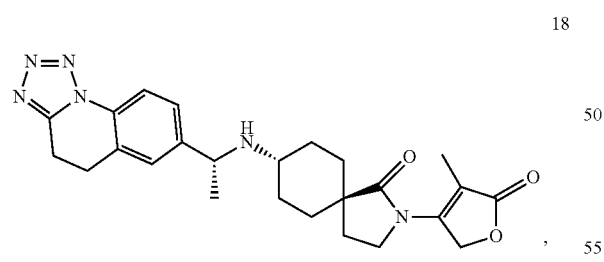
19
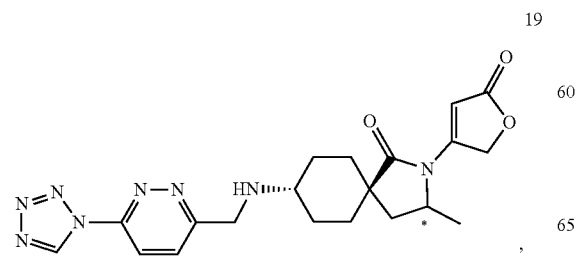
20
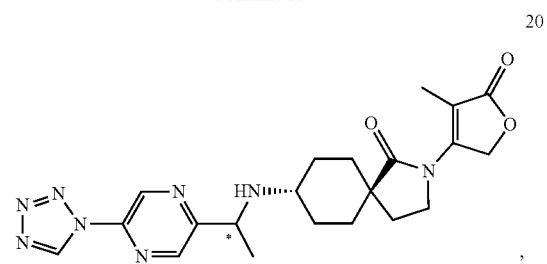
21
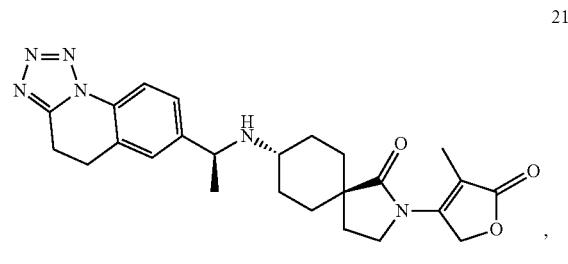
22
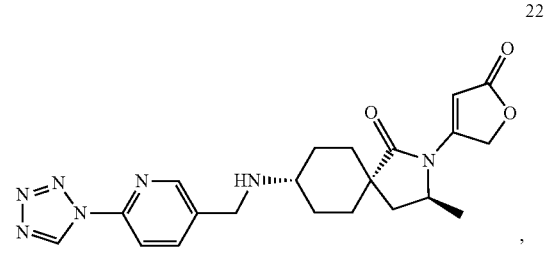
23
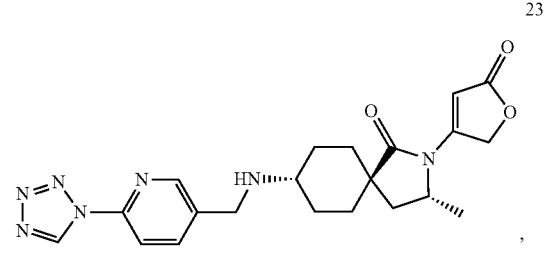
24
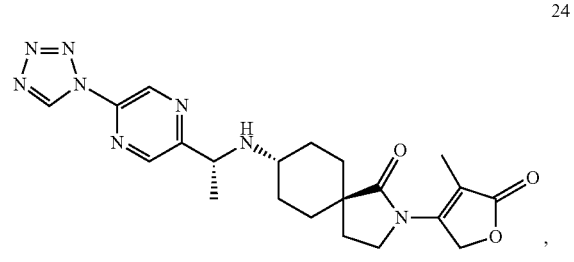
25
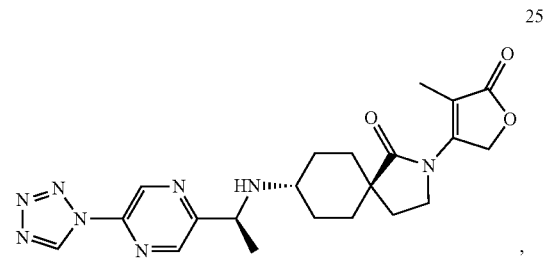

26
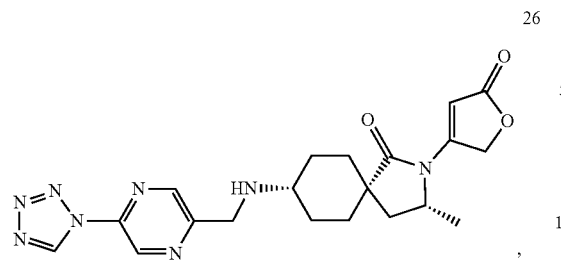
27
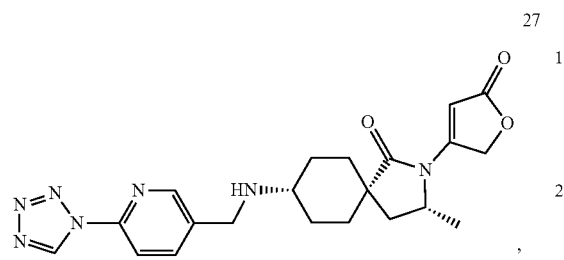
28
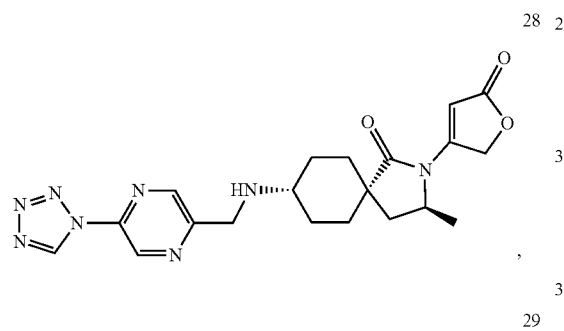
29
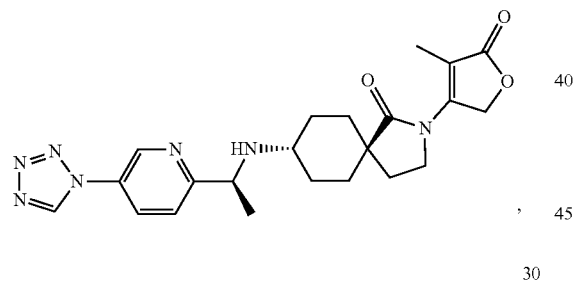
30
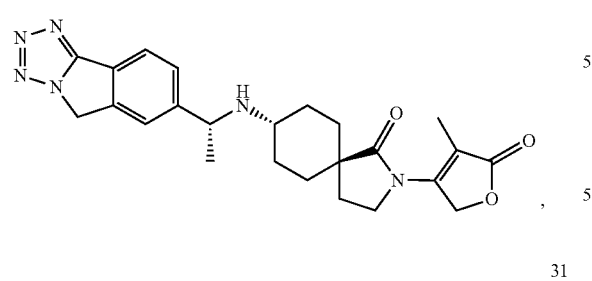
31
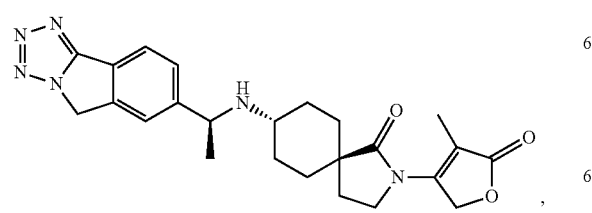
32
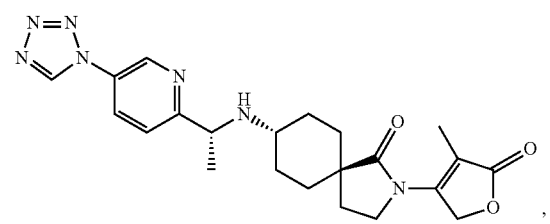
33
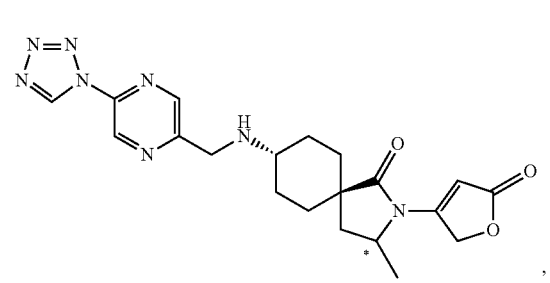
34
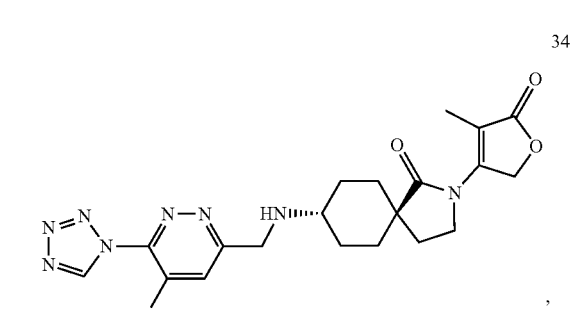
35
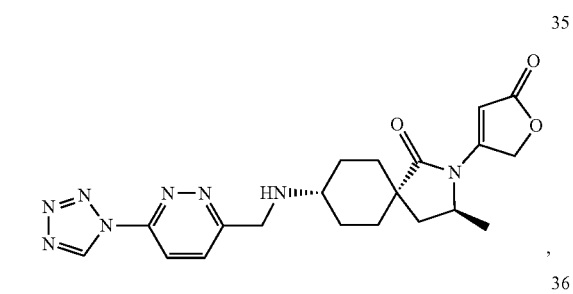
36
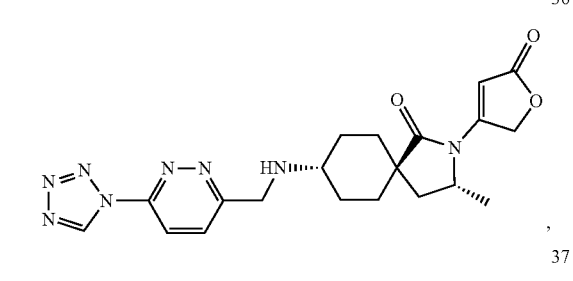
37
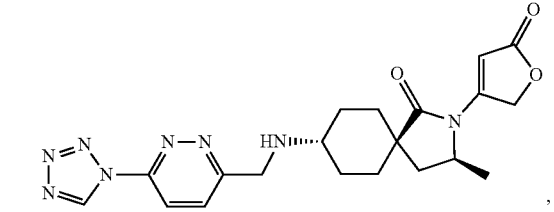

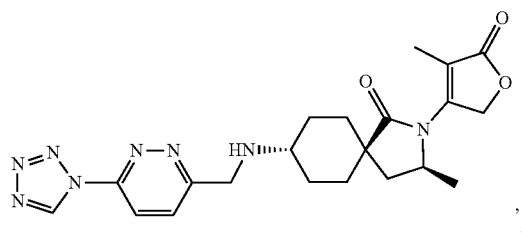
38
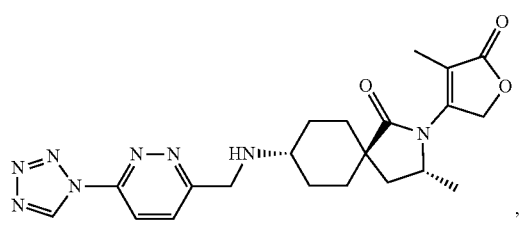
39
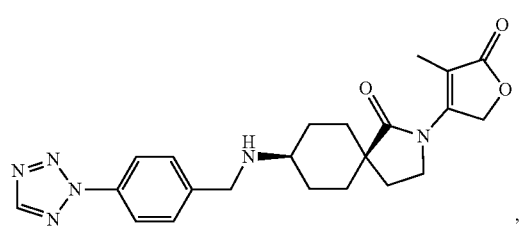
40
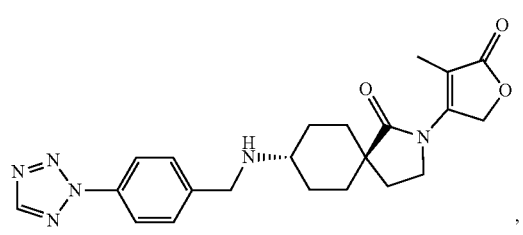
41
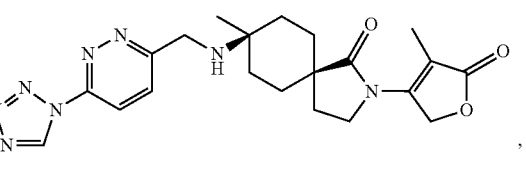
42
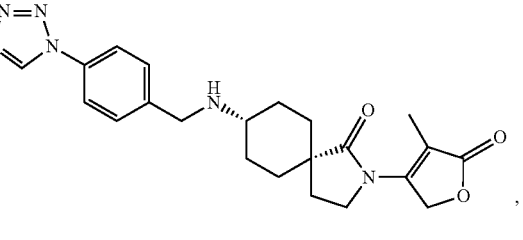
43
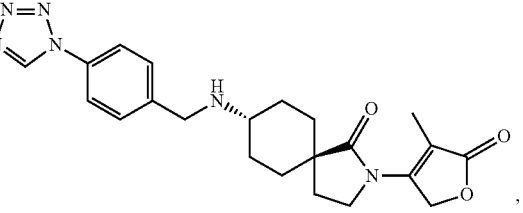
44
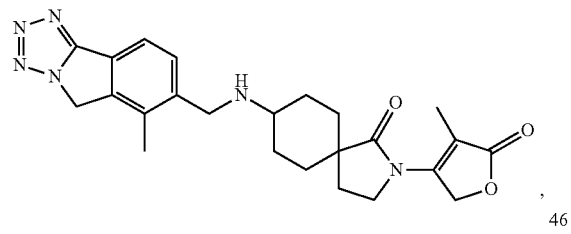
45
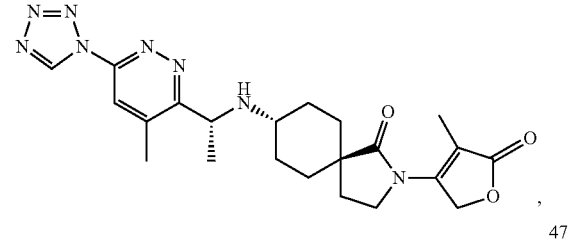
46
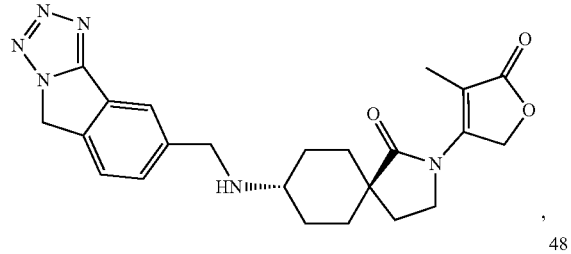
47
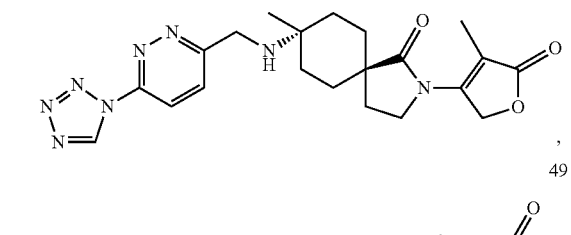
48
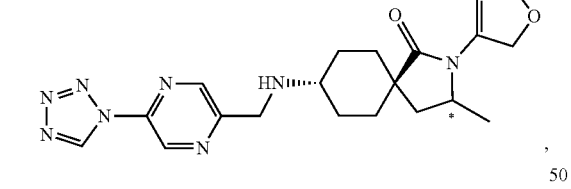
49
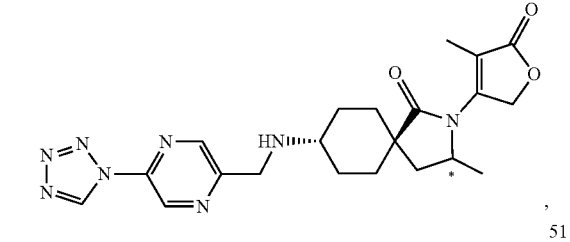
50
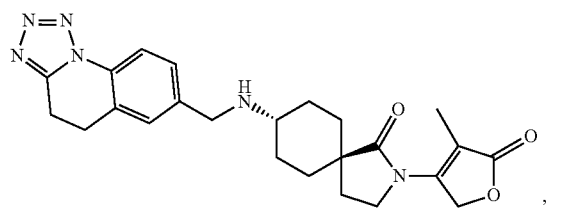
51

52
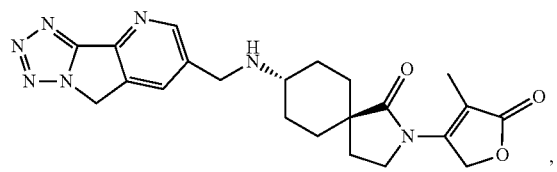
53
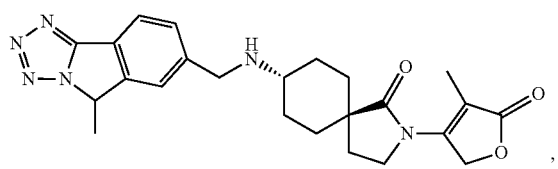
54
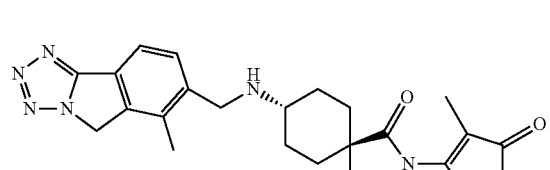
55
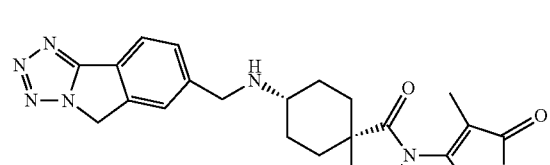
56
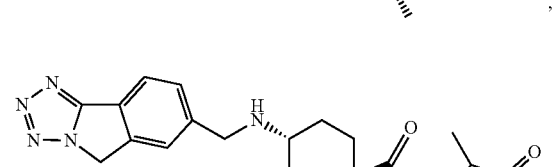
57
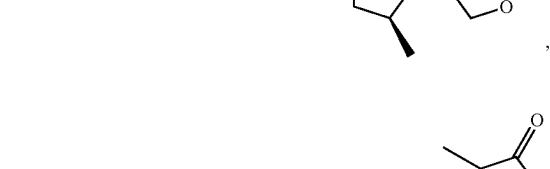
58
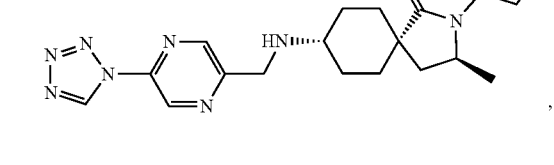
,
59
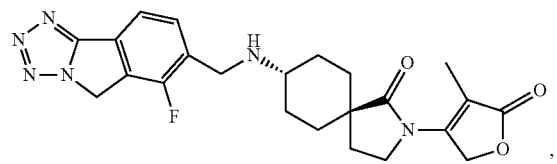
60
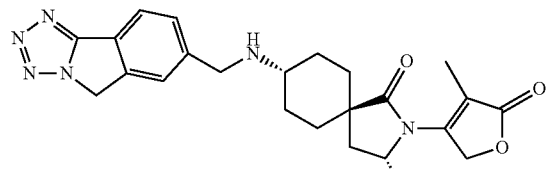
61
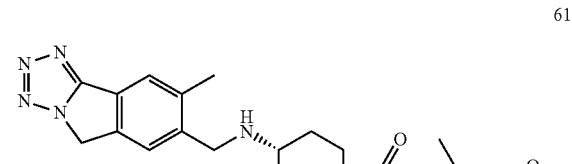
62
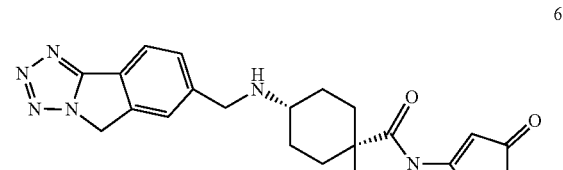
63
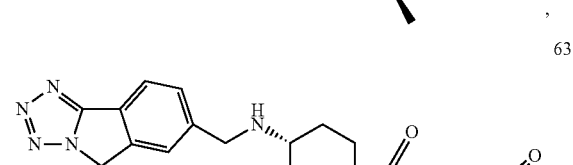
64
65
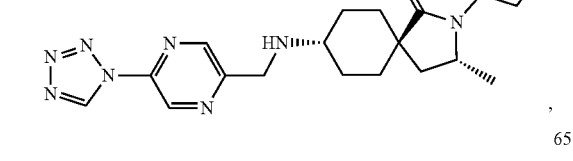
,

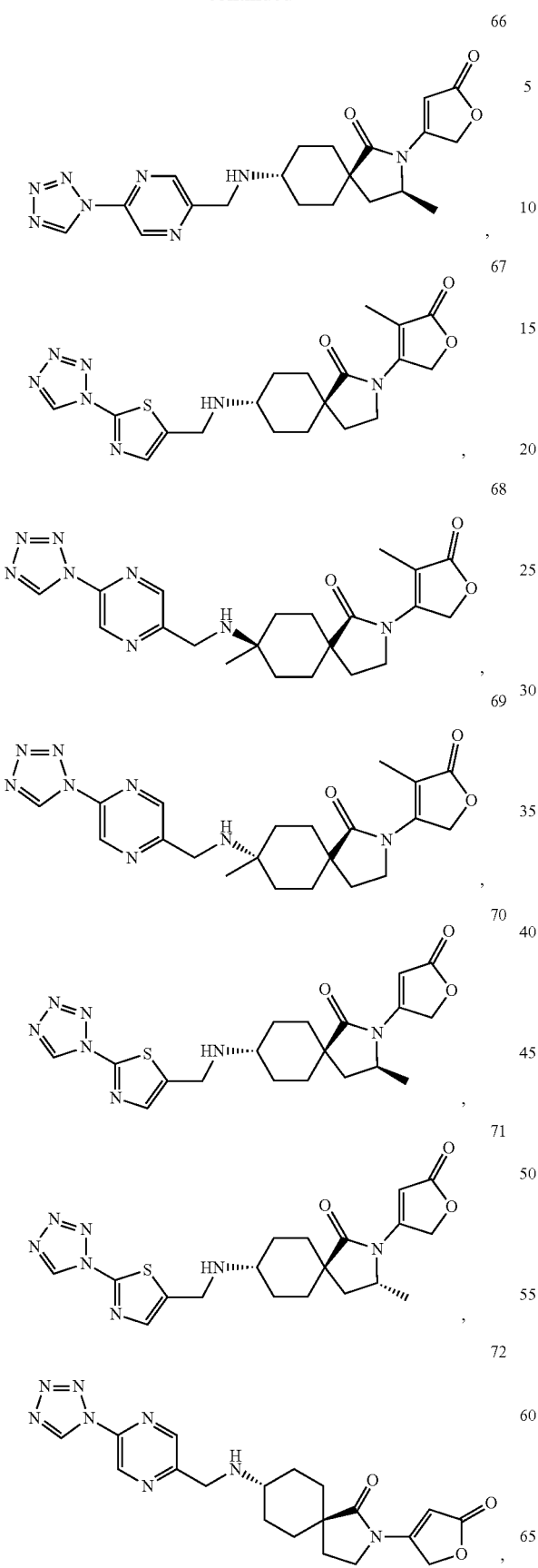
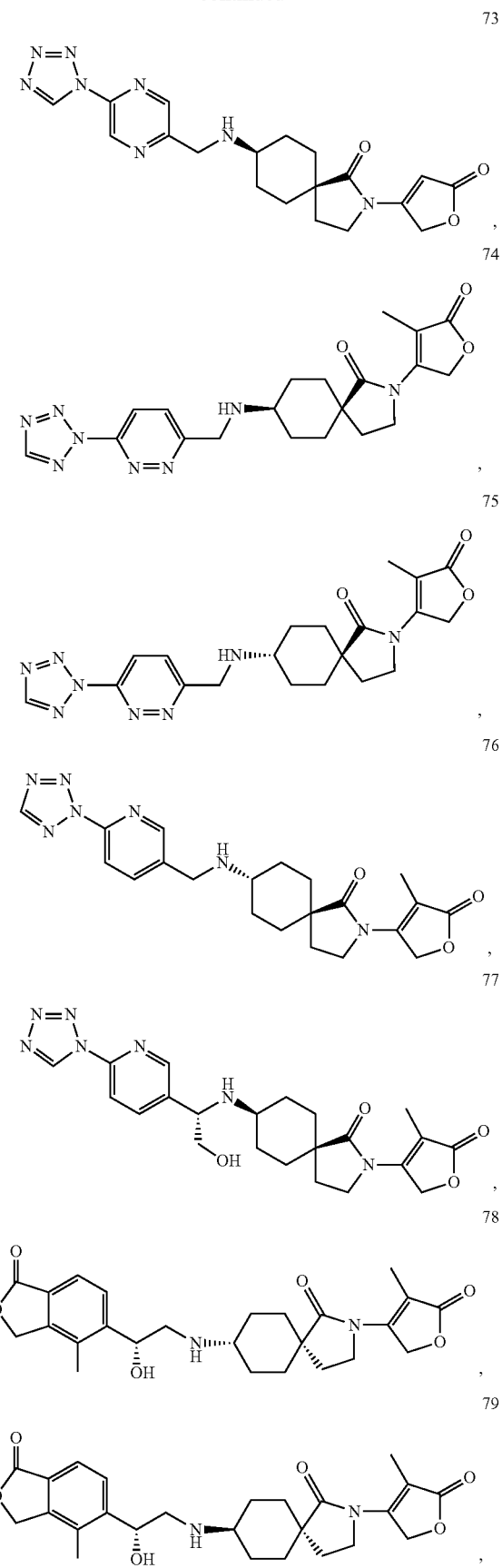

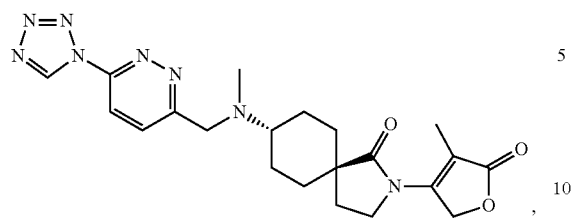
80,
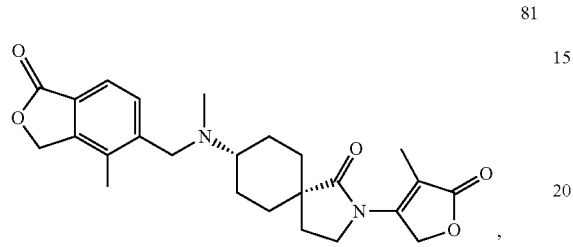
81,
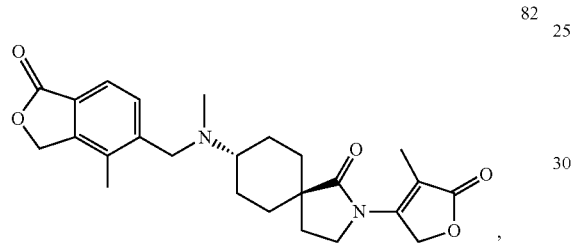
82,
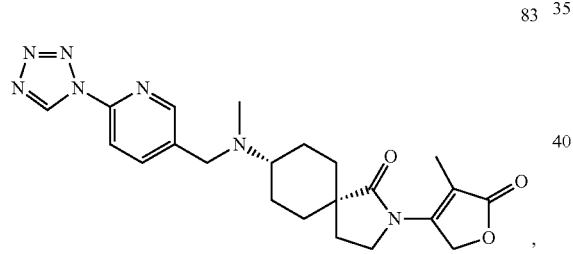
83,
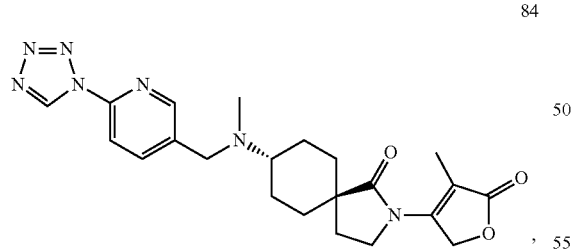
84,
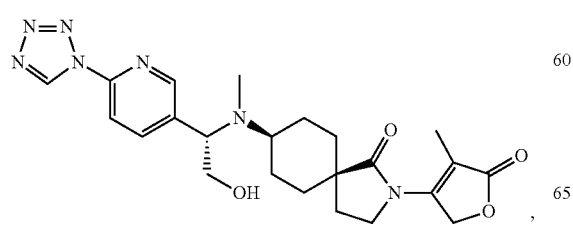
85,
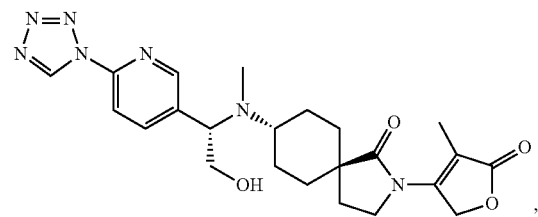
86,
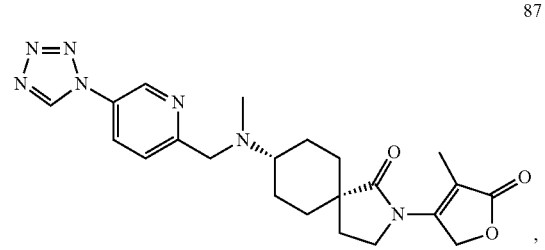
87,
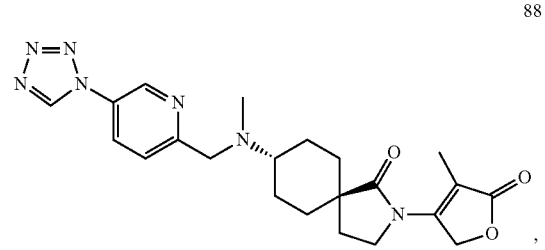
88,
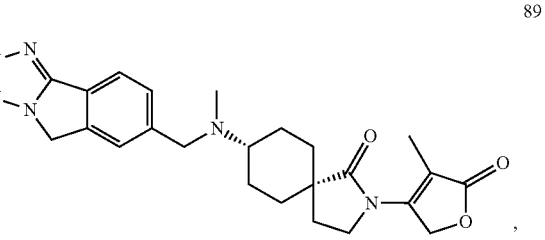
89,
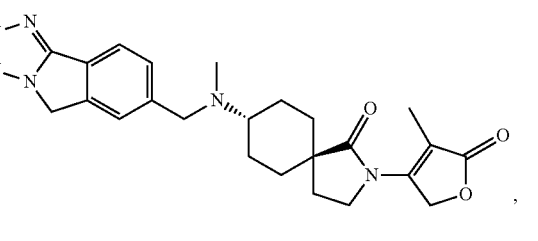
90,
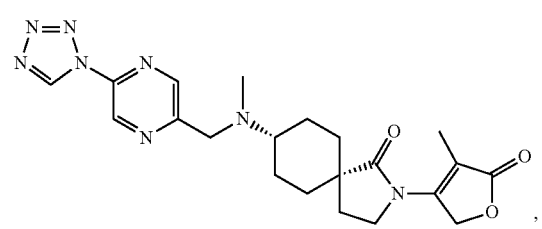
91,

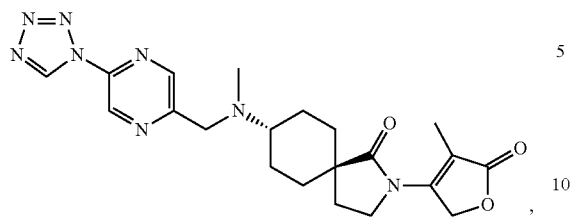
92,
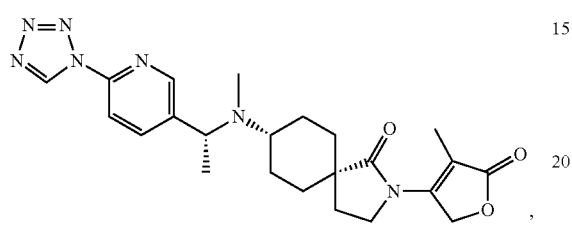
93,
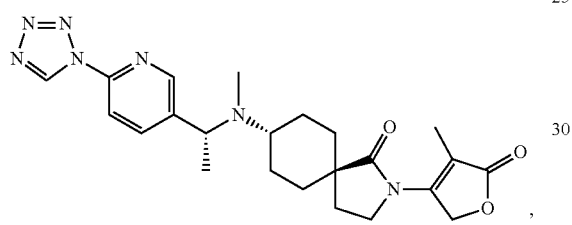
94,
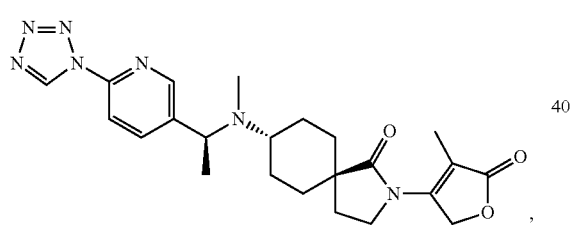
95,
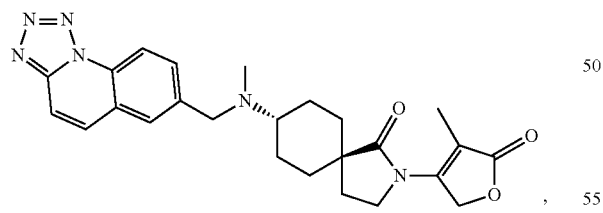
96,
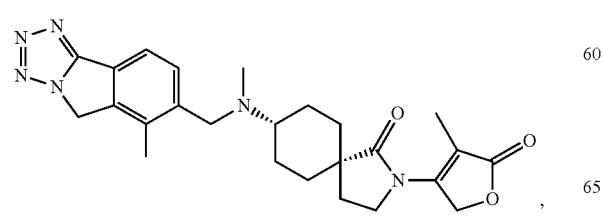
97,
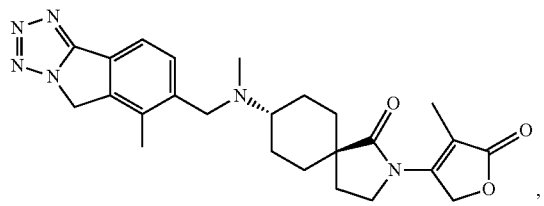
98,
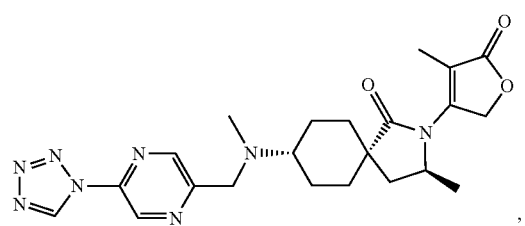
99,
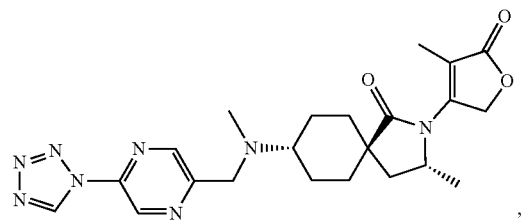
100,
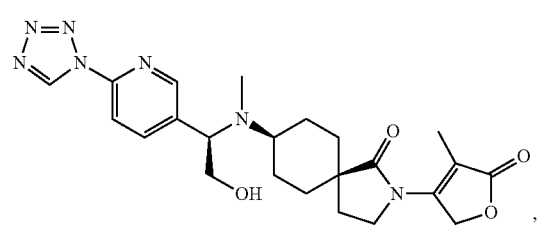
101,
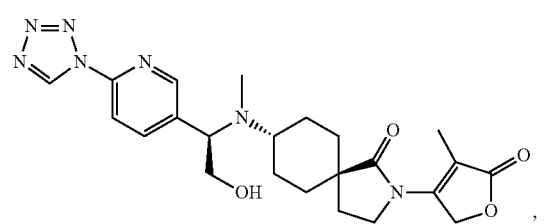
102,
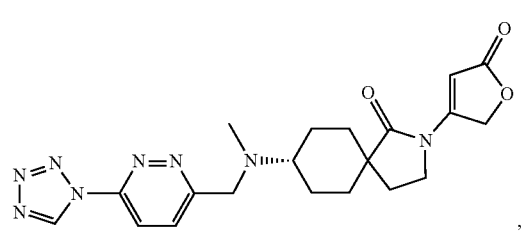
103, 104
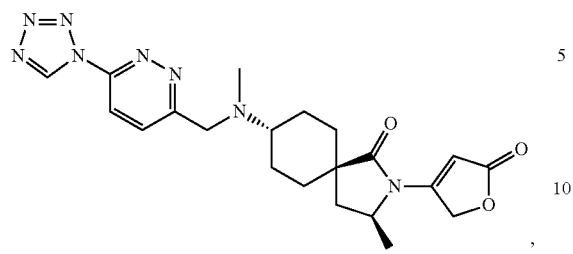
105
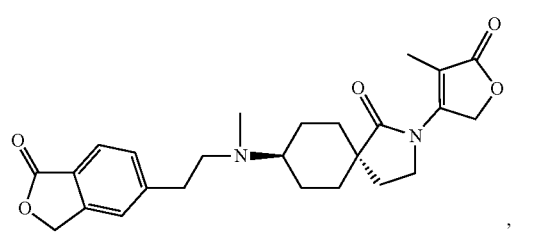
106
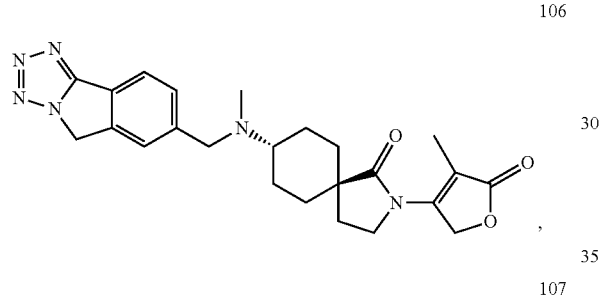
107
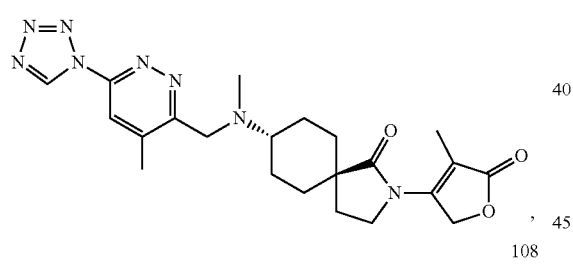
108
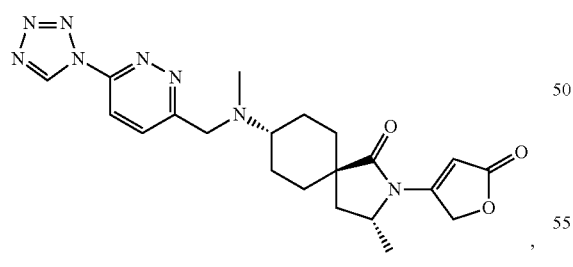
109
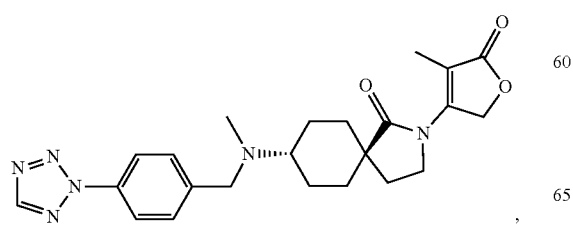
110
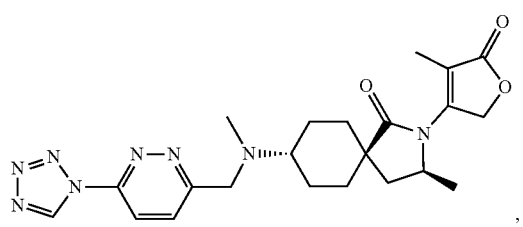
111
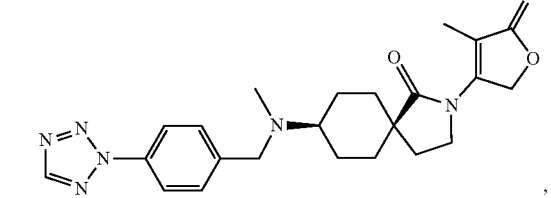
112
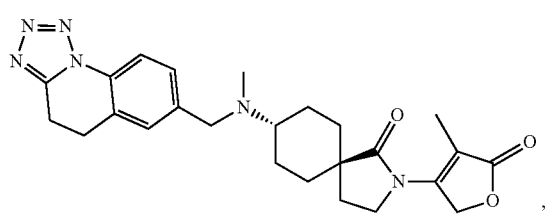
113
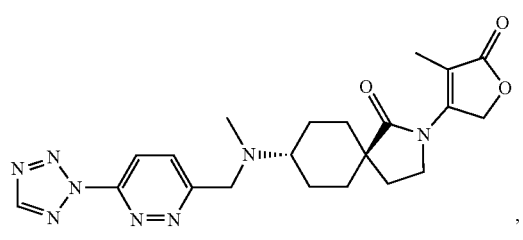
114
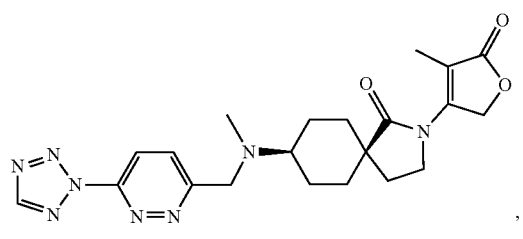
115
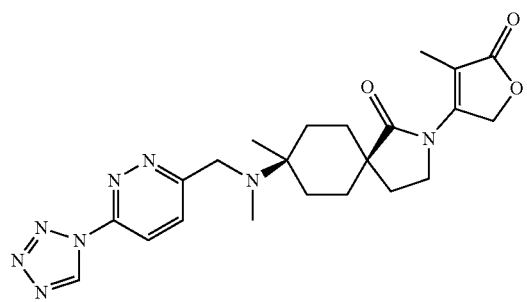

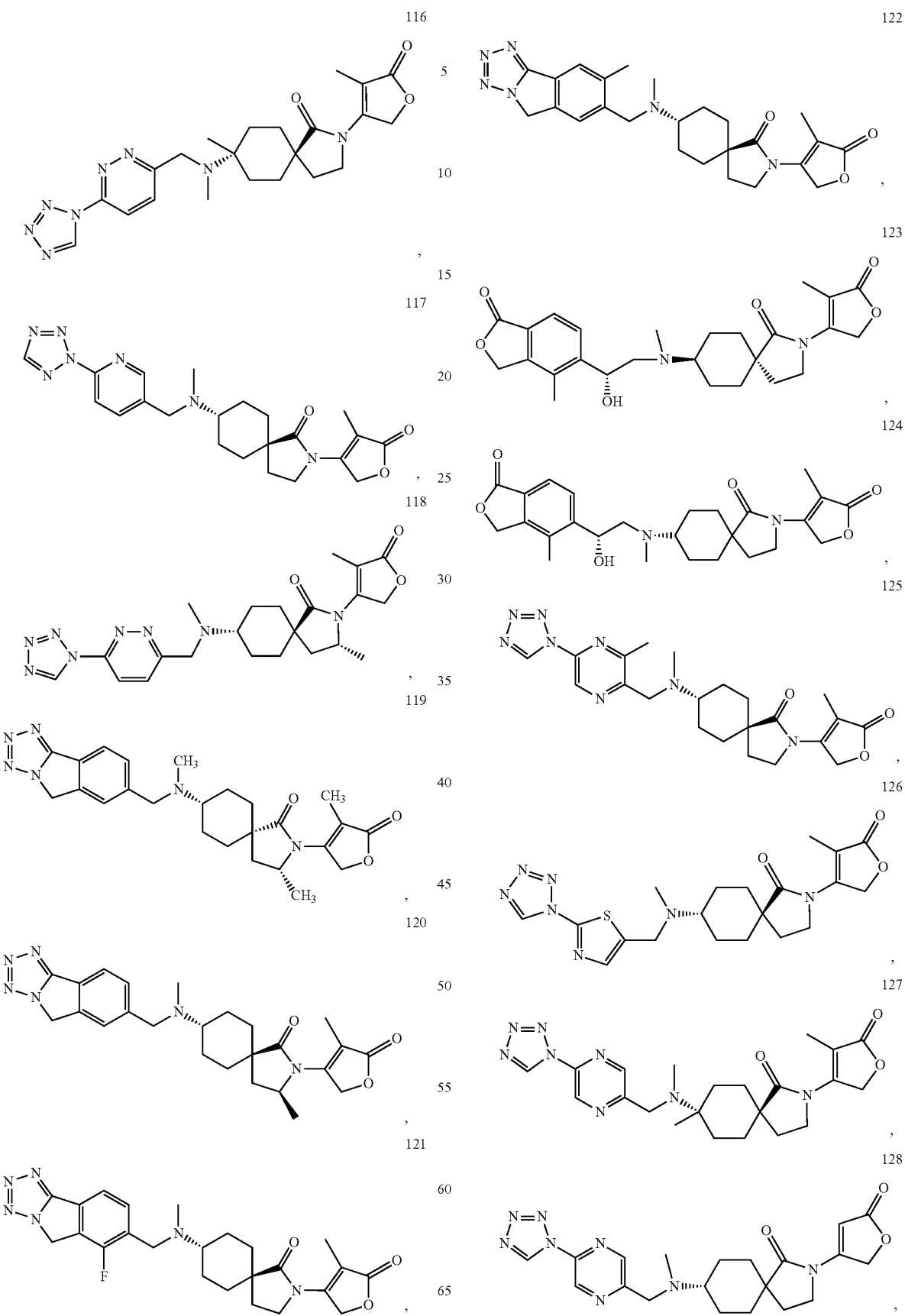

129
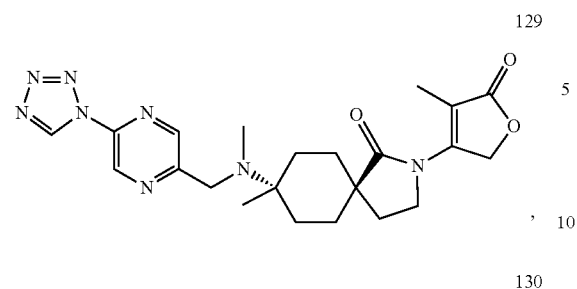
130
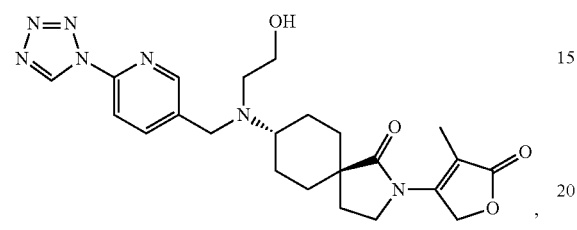
131
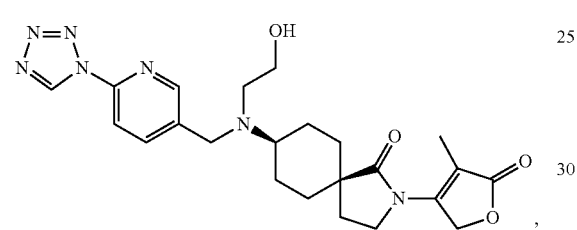
132
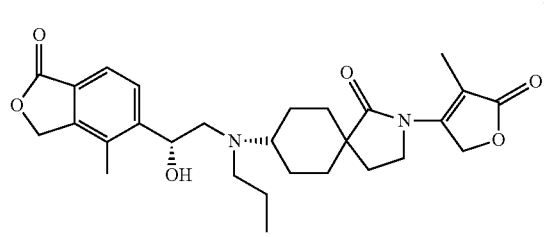
133
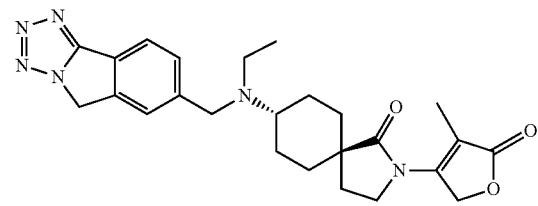
134
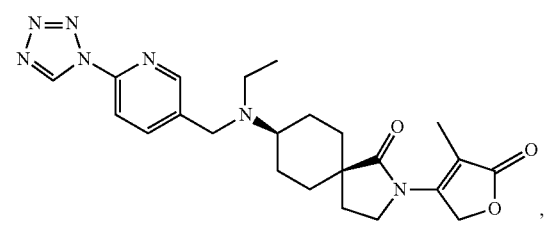
135
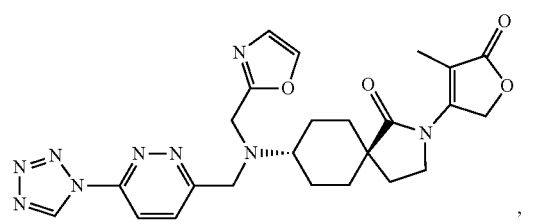
136
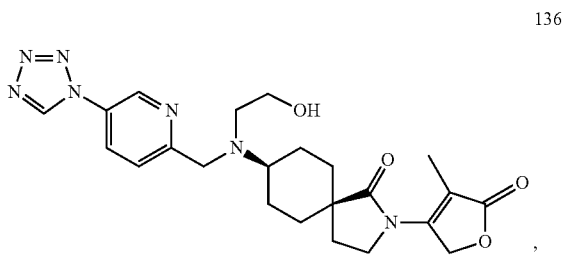
137
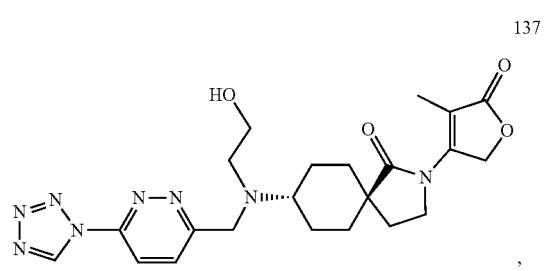
138
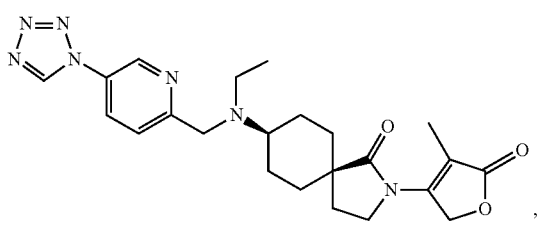
139
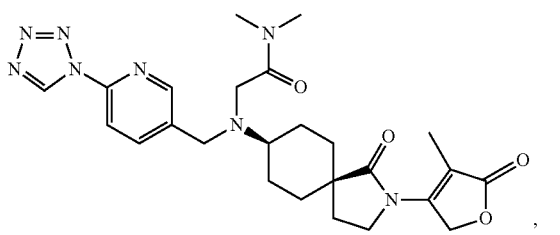
140
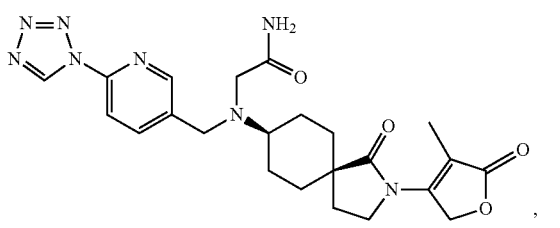

-continued

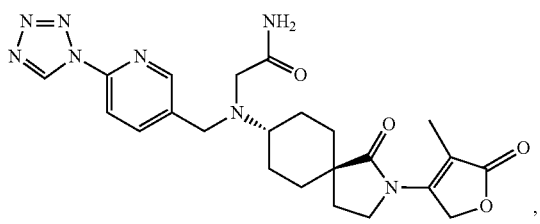
141

, or

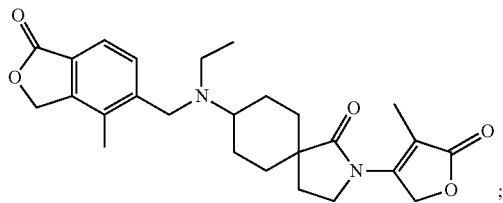
142 or a pharmaceutically acceptable salt thereof.

12. A pharmaceutical composition comprised of a compound of claim 1 or a pharmaceutically acceptable salt thereof and a pharmaceutically acceptable carrier.

13. The pharmaceutical composition of claim 12 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, amiloride, spironolactone, epleranone, triamterene, a pro-drug, or a pharmaceutically acceptable salt of any of the foregoing.

14. A method for inhibiting ROMK comprising administering a compound of claim 1 or a pharmaceutically acceptable salt thereof in a ROMK-inhibitory effective amount to a patient in need thereof.

15. A method for causing diueresis, natriuresis or both, comprising administering a compound of claim 1 or a pharmaceutically acceptable salt thereof in a therapeutically effective amount to a patient in need thereof.

16. A method for the treatment of one or more disorders selected from hypertension, acute heart failure, chronic heart failure, pulmonary arterial hypertension, cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute kidney insufficiency, chronic kidney disease, hypercalcemia, Dent's disease, Meniere's disease, or edematous states comprising administering a compound of claim 1 or a pharmaceutically acceptable salt thereof in a therapeutically effective amount to a patient in need thereof.

* * * * *

UNITED STATES PATENT AND TRADEMARK OFFICE
CERTIFICATE OF CORRECTION

PATENT NO. : 9,718,808 B2  
APPLICATION NO. : 15/106847  
DATED : August 1, 2017  
INVENTOR(S) : Dipshikha Biswas et al.

Page 1 of 1

It is certified that error appears in the above-identified patent and that said Letters Patent is hereby corrected as shown below:

In the Claims

Column 136, In Claim 11, compounds 49 and 50 are as shown below with R1 as methyl (arrows added):

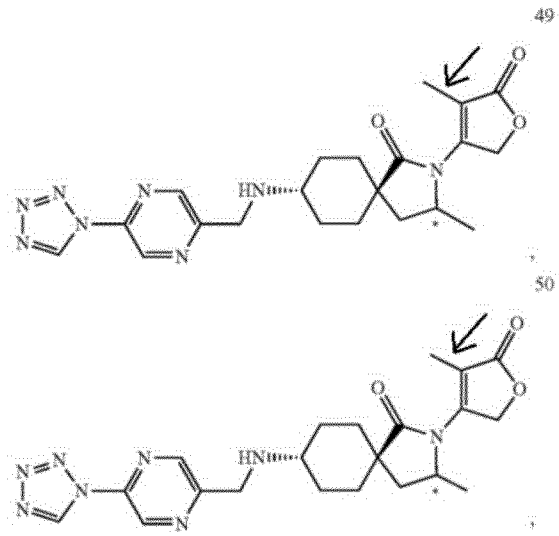

However, compounds 49 and 50 should be (as shown):

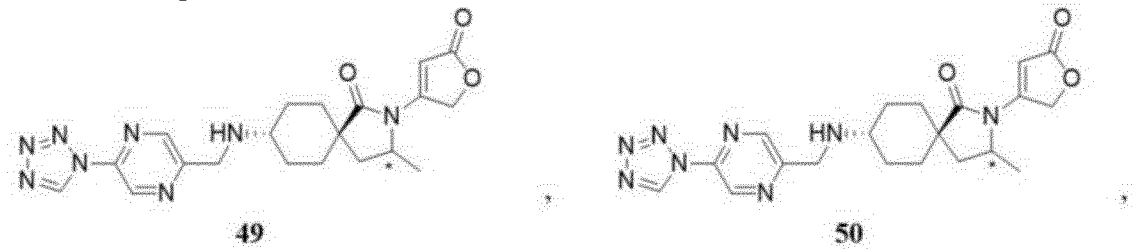

Signed and Sealed this  
Sixteenth Day of July, 2019

Andrei Iancu  
*Director of the United States Patent and Trademark Office*